(12) United States Patent
Hertel et al.

(10) Patent No.: US 6,436,964 B1
(45) Date of Patent: Aug. 20, 2002

(54) PIPERIDINE DERIVATIVES HAVING EFFECTS ON SEROTONIN RELATED SYSTEMS

(75) Inventors: Larry Wayne Hertel, Indianapolis; Daniel Timothy Kohlman, Camby; Sidney Xi Liang, Fishers; David Taiwai Wong, Indianapolis; Yao-Chang Xu, Fishers, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/701,406

(22) PCT Filed: Jun. 29, 1999

(86) PCT No.: PCT/US99/14732

§ 371 (c)(1),
(2), (4) Date: Nov. 28, 2000

(87) PCT Pub. No.: WO00/00198

PCT Pub. Date: Jan. 6, 2000

Related U.S. Application Data

(60) Provisional application No. 60/091,241, filed on Jun. 30, 1998.

(51) Int. Cl.⁷ .................... C07D 405/06; A61K 31/444
(52) U.S. Cl. ....................... 514/333; 546/256
(58) Field of Search ................... 546/256; 514/333

(56) References Cited

U.S. PATENT DOCUMENTS 4,259,338 A    3/1981  Paioni et al.
5,585,374 A  * 12/1996 Cliffe et al. ............... 514/212
5,753,661 A    5/1998  Moltzen et al.

FOREIGN PATENT DOCUMENTS

| GB | 2 056 435 | 6/1979 |
| WO | WO 94/13659 | 12/1993 |
| WO | WO 94/15919 | 12/1993 |
| WO | WO 99/05140 | 7/1998 |

* cited by examiner

*Primary Examiner*—Jane Fan
(74) *Attorney, Agent, or Firm*—Charles T. Joyner; Nelsen L. Lentz

(57) ABSTRACT

The present invention provides the compounds of the following formula:

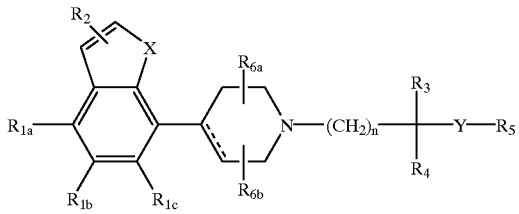

Wherein the variables are as defined in the specification and a method for inhibiting the reuptake of serotonin, antagonizing the 5-$HT_{1A}$ receptor and antagonizing the 5-$HT_{2A}$ receptor which comprises administering to a subject in need of such treatment an effective amount of the compound of above formula.

25 Claims, No Drawings

PIPERIDINE DERIVATIVES HAVING EFFECTS ON SEROTONIN RELATED SYSTEMS

This application is a 371 of PCT/US99/14732 Jun. 29, 1999 which claims benefit of Ser. No. 60/091,241 Jun. 30, 1998.

Pharmaceutical researchers have discovered in recent years that the neurons of the brain which contain monoamines are of extreme importance in a great many physiological processes which very strongly affect many psychological and personality-affecting processes as well. In particular, serotonin (5-hydroxytryptamine; 5-HT) has been found to be a key to a very large number of processes which affect both physiological and psychological functions. Drugs which influence the function of serotonin in the brain are accordingly of great importance and are now used for a surprisingly large number of different therapies.

The early generations of serotonin-affecting drugs tended to have a variety of different physiological functions, considered from both the mechanistic and therapeutic points of view. For example, many of the tricyclic antidepressant drugs are now known to be active as inhibitors of serotonin and norepinephrine reuptake, and also to have anticholinergic, antihistaminic or anti-a-adrenergic activity. More recently, it has become possible to study the function of drugs at individual receptors in vitro or ex vivo, and it has also been realized that therapeutic agents free of extraneous mechanisms of action are advantageous to the patient. Accordingly, the objective of research now is to discover agents which affect only functions of serotonin.

The present invention provides compounds which have selective activity as antagonists and partial agonists of the serotonin-$1_A$ receptor and the serotonin-$2_A$ receptor, and activity as inhibitors of serotonin reuptake. The best-known pharmaceutical with the latter efficacy is fluoxetine, and the importance of its use in the treatment of depression and other conditions is extremely well documented and publicized. Recent scientific articles, for example, Artigas, TIPS, 14, 262 (1993), have suggested that the efficacy of a reuptake inhibitor may be decreased by the activation of serotonin-$1_A$ receptors with the resultant reduction in the firing rate of serotonin neurons. Accordingly, present research in the central nervous system is focusing on the effect of combining reuptake inhibitors with compounds which affect the 5-HT$_{1A}$ receptor. In addition, it has been suggested that a 5-HT$_{2A}$ receptor antagonist would provide treatment of depression with fewer side effects than a typical serotonin reuptake inhibitor.

Compounds exhibiting both serotonin reuptake inhibition activity and 5-HT$_{1A}$ antagonist activity have been described, for example in U.S. Pat. No. 5,576,321, issued Nov. 19, 1996. It has been found that the compounds of the present invention are potent serotonin reuptake inhibitors, antagonists of the 5-HT$_{1A}$ receptor and antagonists of the 5-HT$_{2A}$ receptor.

The present invention provides compounds of formula I:

formula I

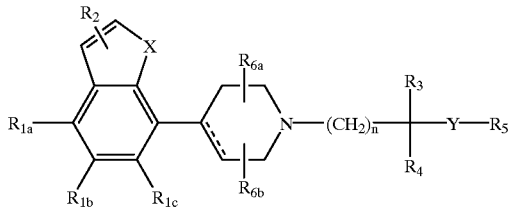

wherein:

X is O, S, NR, S(=O), or S(=O)$_2$;

Y is —C(=O)—, —CH(OH)—, —CH$_2$—, —C(=NOR), CHNR$_7$R, S, SO, or SO$_2$;

------- represents a single or a double bond;

n is 1, 2, 3 or 4;

R is H or C$_1$–C$_6$ alkyl;

R$_{1a}$, R$_{1b}$, R$_{1c}$ and R$_2$ are each independently H, F, Cl, Br, I, OH, C$_1$–C$_6$ alkyl, C$_1$–C$_6$ alkoxy, halo(C$_1$–C$_6$)alkyl, (C$_1$–C$_6$)alkylthio, phenyl, NO$_2$, —NR$_7$R$_8$, —C(=O)NR$_7$R$_8$, —NR7C(=O)R$_8$, CN or phenyl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, (C$_1$–C$_6$)alkylthio, phenyl, NO$_2$, NH$_2$, or CN;

R$_3$ is H, OH, hydroxy(C$_1$–C$_6$)alkyl, C$_1$–C$_6$ alkyl, C$_1$–C$_6$ alkoxy, or (C$_1$–C$_6$)alkylthio;

R$_4$ is aryl, heterocycle, C$_3$–C$_8$ cycloalkyl, aryl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, (C$_1$–C$_6$)alkylthio, phenyl, NO$_2$, NH$_2$, or CN; or heterocycle substituted with from 1 to 3 substituents selected from the group consisting of F, Cl, Br, I, OH, C$_1$–C$_6$ alkyl, C$_1$–C$_6$ alkoxy, halo (C$_1$–C$_6$)alkyl, (C$_1$–C$_6$)alkylthio, phenyl, NO$_2$, NH$_2$, or CN;

R$_5$ is aryl, heterocycle, C$_3$–C$_8$ cycloalkyl, aryl substituted with from 1 to 3 substituents selected from the group consisting of F, Cl, Br, I, OH, C$_1$–C$_6$ alkyl, C$_1$–C$_6$ alkoxy, hydroxy(C$_1$–C$_6$)alkyl, halo(C$_1$–C$_6$)alkyl, (C$_1$–C$_6$)alkylthio, phenyl, NO$_2$, NH$_2$, or CN; or heterocycle substituted with from 1 to 3 substituents selected from the group consisting of F, Cl, Br, I, OH, C$_1$–C$_6$ alkyl, C$_1$–C$_6$ alkoxy, hydroxy(C$_1$–C$_6$)alkyl, halo (C$_1$–C$_6$)alkyl, (C$_1$–C$_6$)alkylthio, phenyl, NO$_2$, NH$_2$, or CN;

R$_{6a}$ and R$_{6b}$ are each independently H or C$_1$–C$_3$ alkyl;

R$_7$ and R$_8$ are each independently H, C$_1$–C$_6$ alkyl, aryl or aryl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, (C$_1$–C$_6$) alkylthio, phenyl, NO$_2$, NH$_2$, or CN;

and the pharmaceutically acceptable salts thereof.

The present invention further provides a method of inhibiting the reuptake of serotonin and antagonizing the 5-HT$_{1A}$ receptor which comprises administering to a subject in need of such treatment an effective amount of a compound of formula I.

In addition, the present invention provides a method of inhibiting the reuptake of serotonin, antagonizing the 5-HT$_{1A}$ receptor, and antagonizing the 5-HT$_{2A}$ receptor, which comprises administering to a subject in need of such treatment an effective amount of a compound of formula I.

More particularly, the present invention provides a method for alleviating the symptoms caused by withdrawal or partial withdrawal from the use of tobacco or of nicotine; a method of treating anxiety; and a method of treating a condition chosen from the group consisting of depression, hypertension, cognitive disorders, psychosis, sleep disorders, gastric motility disorders, sexual dysfunction, brain trauma, memory loss, eating disorders and obesity, substance abuse, obsessive-compulsive disease, panic disorder and migraine; which methods comprise administering to a subject in need of such treatment an effective amount of a compound of formula I.

In addition, the present invention provides a method of potentiating the action of a serotonin reuptake inhibitor comprising administering to a subject in need of such treatment a compound of formula I in combination with a serotonin reuptake inhibitor.

In addition, the invention provides pharmaceutical compositions of compounds of formula I, including the hydrates thereof, comprising, as an active ingredient, a compound of formula I in combination with a pharmaceutically acceptable carrier, diluent or excipient. This invention also encompasses novel intermediates, and processes for the synthesis of the compounds of formula I.

The invention further provides intermediates of the formula:

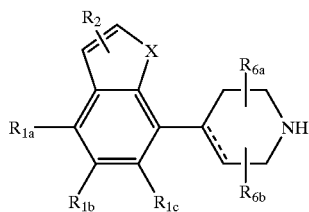

wherein:
X is O, S, NR, S(=O), or S(=O)$_2$;
------ represents a single or a double bond;
R is H or $C_1$–$C_6$ alkyl;
$R_{1a}$, $R_{1b}$, $R_{1c}$ and $R_2$ are each independently H, F, Cl, Br, I, OH, $C_1$–$C_6$ alkyl, $C_1$–$C_6$ alkoxy, halo($C_1$–$C_6$)alkyl, ($C_1$–$C_6$)alkylthio, phenyl, NO$_2$, —NR$_7$R$_8$, —C(=O)NR$_7$R$_8$, —NR$_7$C(=O)R$_8$, CN or phenyl substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, ($C_1$–$C_6$)alkylthio, phenyl, NO$_2$, NH$_2$, or CN;
$R_{6a}$, and $R_{6b}$ are each independently H or $C_1$–$C_3$ alkyl;
$R_7$ and $R_8$ are each independently H, $C_1$–$C_6$ alkyl, aryl or aryl substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, ($C_1$–$C_6$) alkylthio, phenyl, NO$_2$, NH$_2$, or CN.

In addition, the invention further provides intermediates of the formula:

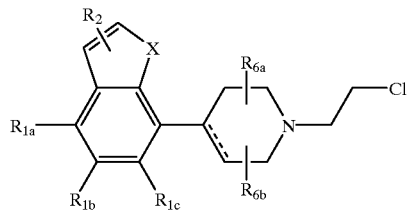

wherein:
X is O, S, NR, S(=O), or S(=O)$_2$;
------ represents a single or a double bond;
R is H or $C_1$–$C_6$ alkyl;
$R_{1a}$, $R_{1b}$, $R_{1c}$ and $R_2$ are each independently H, F, Cl, Br, I, OH, $C_1$–$C_6$ alkyl, $C_1$–$C_6$ alkoxy, halo($C_1$–$C_6$)alkyl, ($C_1$–$C_6$)alkylthio, phenyl, NO$_2$, —NR$_7$R$_8$, —C(=O)NR$_7$R$_8$, —NR$_7$C(=O)R$_8$, CN or phenyl substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, ($C_1$–$C_6$)alkylthio, phenyl, NO$_2$, NH$_2$, or CN;
$R_{6a}$ and $R_{6b}$ are each independently H or $C_1$–$C_3$ alkyl;

$R_7$ and $R_8$ are each independently H, $C_1$–$C_6$ alkyl, aryl or aryl substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, ($C_1$–$C_6$) alkylthio, phenyl, NO$_2$, NH$_2$, or CN.

According to another aspect, the present invention provides the use of a compound of formula I for the manufacture of a medicament for inhibiting the reuptake of serotonin, antagonizing the 5-HT$_{1A}$ receptor, and antagonizing the 5-HT$_{2A}$ receptor.

In addition, the present invention provides the use of a compound of formula I for inhibiting the reuptake of serotonin, antagonizing the 5-HT$_{1A}$ receptor, and antagonizing the 5-HT$_{2A}$ receptor.

As used herein, an acyclic or cyclic acetal or ketal is represented by the following:

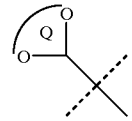

and corresponds for example, to the following groups:

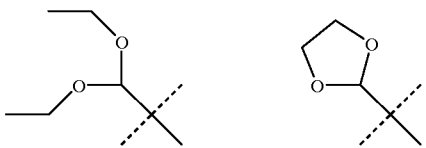

As used herein the term "Pg" refers to a protecting group on the amine which are commonly employed to block or protect the amine while reacting other functional groups on the compound. Examples of protecting groups (Pg) used to protect the amino group and their preparation are disclosed by T. W. Greene, "Protective Groups in Organic Synthesis," John Wiley & Sons, 1981, pages 218–287. Choice of the protecting group used will depend upon the substituent to be protected and the conditions that will be employed in subsequent reaction steps wherein protection is required, and is well within the knowledge of one of ordinary skill in the art. Preferred protecting groups are t-butoxycarbonyl also known as a BOC protecting group, and benzyloxycarbonyl.

As used herein, the terms "Halo", "Halide" or "Hal" refers to a chlorine, bromine, iodine or fluorine atom, unless otherwise specified herein.

As used herein, the term "Me" refers to a methyl group, the term "Et" refers to an ethyl group, the term "Pr" refers to a propyl group, the term "iPr" refers to an isopropyl group, "Bu" refers to a butyl group, and the term "Ph" refers to a phenyl group.

As used herein the term "serotonin" is equivalent to and interchangeable with the terms "5-HT" or "5-hydroxytryptamine".

As used herein the term "$C_1$–$C_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "$C_1$–$C_6$ alkyl" includes within its definition the term "$C_1$–$C_4$ alkyl".

As used herein the term "halo($C_1$–$C_6$)alkyl" refers to a straight or branched alkyl chain having from one to six carbon atoms with 1, 2 or 3 halogen atoms attached to it. Typical halo($C_1$–$C_6$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl and the like. The term "halo($C_1$–$C_6$)alkyl" includes within its definition the term "halo($C_1$–$C_4$)alkyl".

As used herein the term "hydroxy($C_1$–$C_6$)alkyl" refers to a straight or branched alkyl chain having from one to six carbon atoms with a hydroxy group attached to it, such as —$CH_2OH$, —$CH_2CH_2OH$, —$CH_2CH_2CH_2OH$, and the like. The term "hydroxy($C_1$–$C_6$)alkyl" includes within its definition the term "hydroxy($C_1$–$C_4$)alkyl".

As used herein the term "($C_1$–$C_6$)alkylthio" refers to a straight or branched alkyl chain having from one to six carbon atoms attached to a sulfur atom. Typical ($C_1$–$C_6$) alkylthio groups include —$SCH_3$, —$SCH_2CH_3$, —$S(CH_2)_2CH_3$, —$S(CH_2)_3CH_3$, —$S(CH_2)_4CH_3$, —$S(CH_2)_5CH_3$, and the like. The term "($C_1$–$C_6$)alkylthio" includes within its definition the term "($C_1$–$C_4$)alkylthio".

As used herein the term "$C_1$–$C_6$ alkoxy" refers to a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_4$ alkoxy".

As used herein the term "hydroxy($C_1$–$C_6$)alkyl" refers to a straight or branched alkyl chain having from one to six carbon atoms with a hydroxy group attached to it. Typical hydroxy($C_1$–$C_6$)alkyl groups include hydroxymethyl, 2-hydroxyethyl, 1-hydroxyisopropyl, 2-hydroxypropyl, 2-hydroxybutyl, 3-hydroxyisobutyl, hydroxy-t-butyl, 1-hydroxypentyl, 1-hydroxyhexyl and the like. The term "hydroxy($C_1$–$C_6$)alkyl" includes within its definition the term "hydroxy($C_1$–$C_4$)alkyl".

As used herein the term "$C_3$–$C_8$ cycloalkyl" refers to a saturated hydrocarbon ring structure containing from three to eight carbon atoms. Typical $C_3$–$C_8$ cycloalkyl groups include cyclopropyl, cyclobutyl, cyclopentyl, cyclohexyl, cycloheptyl, cyclooctyl, and the like.

As used herein the term "aryl" refers to a phenyl or naphthyl group.

As used herein the term "heterocycle" refers to a stable 5- to 7-membered monocyclic or 7- to 10-membered bicyclic heterocyclic ring which is saturated or unsaturated, and consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure.

Examples of such heterocycles include piperidinyl, piperazinyl, azepinyl, pyrrolyl, pyrrolidinyl, pyrazolyl, pyrazolidinyl, imidazolyl, imidazolinyl, imidazolidinyl, pyridyl, pyridyl N-oxide, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinyl-sulfoxide, thiamorpholinylsulfone, oxadiazolyl, triazolyl, tetrahydroquinolinyl, tetrahydrisoquinolinyl, and the like.

As used herein, the following numbering system applies to the bicyclic portion of formula I as follows:

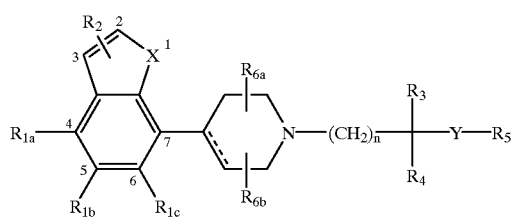

formula I

In addition, it is appreciated by one of ordinary skill in the art that formula I encompasses the following structures:

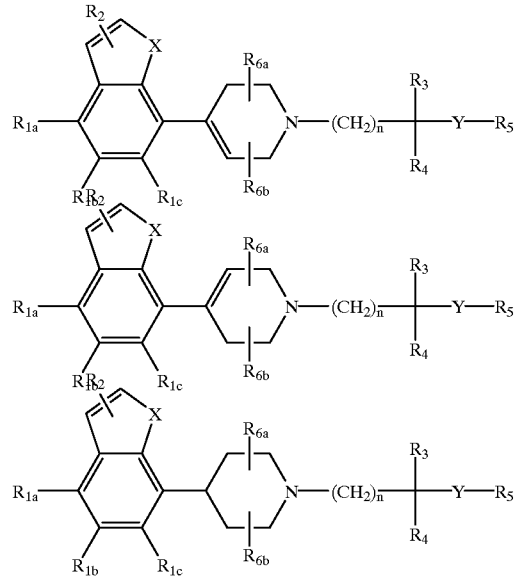

This invention includes the hydrates and the pharmaceutically acceptable salts of the compounds of formula I. A compound of this invention can possess a sufficiently basic functional group which can react with any of a number of inorganic and organic acids, to form a pharmaceutically acceptable salt.

The term "pharmaceutically acceptable salt" as used herein, refers to salts of the compounds of formula I which are substantially non-toxic to living organisms. Typical pharmaceutically acceptable salts include those salts prepared by reaction of the compounds of the present invention with a pharmaceutically acceptable mineral or organic acid. Such salts are also known as acid addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, g-hydroxybutyrate, glycolate, tartrate, methanesulfonate, propanesulfonate, naphthalene-1- sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid, oxalic acid and methanesulfonic acid.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that such salts may exist as a hydrate.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of formulas I or Ia can be resolved by one of ordinary skill in the art using standard techniques well known in the art, such as those described by J. Jacques, et al., "Enantiomers, Racemates, and Resolutions", John Wiley and Sons, Inc., 1981. Examples of resolutions include recrystallization techniques or chiral chromatography.

Some of the compounds of the present invention have one or more chiral centers and may exist in a variety of stereoismeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

As used herein, the term "SRI" refers to serotonin reuptake inhibitor.

The compounds of formula I can be prepared by techniques and procedures readily available to one of ordinary skill in the art, for example by following the procedures as set forth in the following Schemes. These schemes are not intended to limit the scope of the invention in any way. All substituents, unless otherwise indicated, are previously defined. The reagents and starting materials are readily available to one of ordinary skill in the art. Scheme I provides a synthesis of compounds of structure (8).

Scheme I

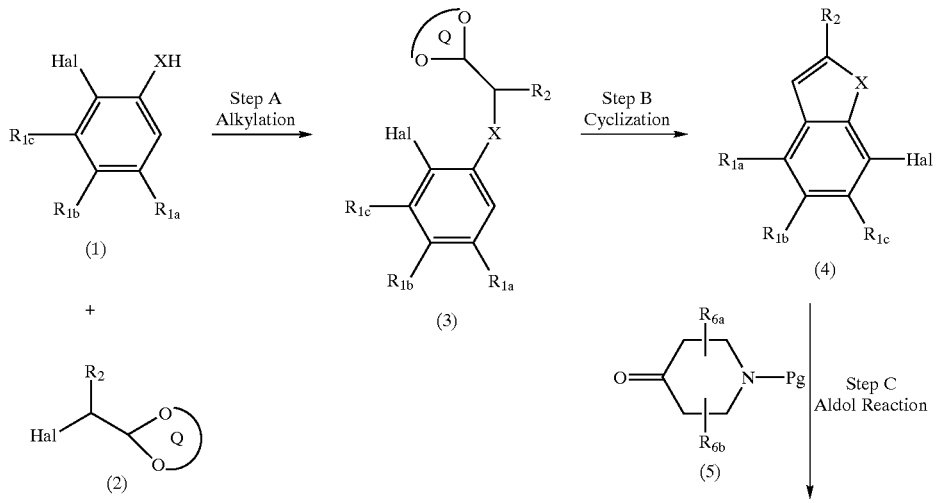

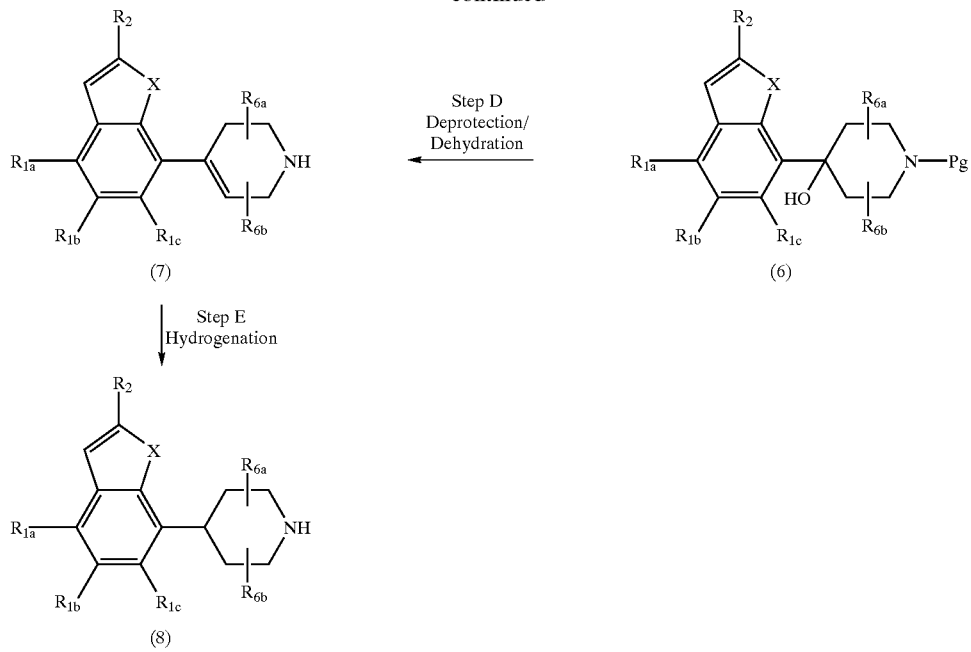

(7)

Step D
Deprotection/
Dehydration (6)

Step E
Hydrogenation (8)

Q is an acyclic or cyclic acetal
Pg is a protecting group

In Scheme I, step A, the compound of structure (1) is alkylated with a compound of structure (2) under conditions well known in the art. For example, compound (1) is dissolved in a suitable organic solvent, such as dimethylformamide (DMF) or tetrahydrofuran (THF). Examples of compound (1) include 2-bromothiophenol, 2-bromophenol, 2-bromo-3-fluorophenol, 2-bromo-4-fluorophenol, 2-bromo-5-fluorophenol, 2-chloro-4-(1,1-dimethylethyl)phenol, 2-bromo-5-chlorophenol, 3-bromo-4-hydroxybenzonitrile, 2-chloro-4-(tert-phenyl)phenol, 2-chloro-5-(trifluoromethyl)phenol, 3-chloro-4-hydroxybenzotrifluoride, 2-chloro-4-nitrophenol, 3-chloro-4-biphenylol, 3-bromo-4-hydroxybiphenyl, 2-chloro-4-fluorothiophenol, 2-chloro-4-methylphenol, 2-chloro-4-methoxyphenol, 2-chloro-5-methoxyphenol, 2-bromo-4-methylphenol, 2-chloro-5-methylphenol, 4-bromoresorcinol, 4-chlororesorcinol, 2-bromo-4-chlorophenol, and the like. As used in Scheme I, Hal represents Cl, Br or I only, and X represents S, O or NR. The solution is treated with a slight excess of a suitable base, such as potassium carbonate or sodium hydride followed by addition of about 1.05 to about 1.20 equivalents of compound (2). Examples of compound (2) include bromoacetaldehyde diethyl acetal, 2-bromomethyl-1,3-dioxolane and the like. The reaction mixture is then stirred at room temperature to reflux for about 1 to 7 hours. The product is then isolated and purified by extraction techniques and chromatography. For example, the reaction is diluted with water and extracted with a suitable organic solvent, such as ethyl acetate. The organic extracts are combined, dried over anhydrous sodium sulfate, filtered and concentrated under vacuum. The residue is then purified by flash chromatography on silica gel with a suitable eluent, such as ethyl acetate/hexane to provide compound (3).

In Scheme I, step B, compound (3) is cyclized to the compound of structure (4) under acidic conditions. For example, compound (3) is dissolved in a suitable organic solvent, such as chlorobenzene and the solution is added dropwise to a refluxing mixture of polyphosphoric acid and chlorobenzene. The reaction mixture is heated at reflux for about 2 to 5 hours and then cooled to room temperature. The compound (4) is then isolated and purified by techniques well known in the art. For example, the reaction mixture is made slightly basic with 1N sodium hydroxide and then extracted with a suitable organic solvent, such as ethyl acetate. The organic extracts are combined, dried over anhydrous sodium sulfate, filtered and concentrated under vacuum. The residue is then purified by flash chromatography on silica gel with a suitable eluent, such as hexane or ethyl acetate/hexane to provide the compound (4).

In Scheme I, step C, compound (4) undergoes an aldol reaction with the piperidone of structure (5) under standard conditions well known in the art, such as Grignard Type conditions (See for example J. March, "Advanced Organic Chemistry: Reactions, Mechanisms, and Structure," $2^{nd}$ Edition, McGraw-Hill, 1977, 836–841), to provide the alcohol of structure (6). For example, compound (4) is dissolved in a suitable organic solvent, such as diethyl ether and the solution is added dropwise to a mixture of about 2 equivalents of magnesium suspended in diethyl ether. If necessary, about 1 equivalent of dibromoethane is then added and the reaction is heated to reflux for about 1 to 5 hours. The reaction is then cooled to room temperature and about 1 equivalent of the piperidone (5) is added to the prepared Grignard reagent. The reaction is then allowed to stir at room temperature for about 5 to 18 hours. The reaction is quenched by addition of water and the alcohol (6) is isolated and purified by techniques well known in the art. For example, the quenched reaction is extracted with a suitable organic solvent, such as diethyl ether, the organic extracts are combined, dried over anhydrous sodium sulfate, filtered and concentrated under vacuum. The residue is then purified by flash chromatography on silica gel with a suitable eluent, such as ethyl acetate/hexane to provide alcohol (6).

In Scheme I, step D, alcohol (6) is deprotected and dehydrated under standard conditions well known in the art to provide to provide the 1,2,3,6-tetrahydropyridine of structure (7). One of ordinary skill in the art would readily appreciate that deprotection and dehydration can be carried out in a stepwise fashion, in any order, or concomitantly. For example, step D is carried out concomitantly by dissolving the alcohol (6) in a suitable organic solvent, such as toluene and treating the solution with an excess of a suitable acid, such as p-toluenesulfonic acid. The reaction is heated at reflux for about 1 to 4 hours, then cooled and the solution is made basic with a suitable base, such as 1N sodium hydroxide. The 1,2,3,6-tetrahydropyridine (7) is then isolated and purified by techniques well known in the art. For example, the solution is extracted with a suitable organic solvent, such as ethyl acetate, the organic extracts are combined, dried over anhydrous sodium sulfate, filtered and concentrated under vacuum. The residue can then be purified if necessary by flash chromatography on silica gel with a suitable eluent, such as ethyl acetate/hexane to provide 1,2,3,6-tetrahydropyridine (7).

In Scheme I, step E, 1,2,3,6-tetrahydropyridine (7) can be hydrogenated under conditions well known in the art to provide the piperidine of structure (8). For example, the 1,2,3,6-tetrahydropyridine (7) is dissolved in a suitable organic solvent, such as absolute ethanol, and treated with a suitable hydrogenation catalyst, such as 10% palladium on carbon. The reaction mixture is then treated with an excess of ammonium formate and the reaction is heated at reflux for about 2 to 4 hours. The reaction mixture is then cooled, filtered to remove the catalyst and the filtrate is concentrated under vacuum to provide piperidine (8). The piperidine (8) can be purified by flash chromatography on silica gel with a suitable eluent, such as ethyl acetate/hexane. Alternatively, the residue can be converted to a pharmaceutically acceptable salt, such as the oxalate salt by dissolving the residue in methanol, treating with 1 equivalent of oxalic acid and then concentrating the solution under vacuum. The solid can then be purified by recrystallization from a suitable organic solvent, such as diethyl ether to provide the purified oxalate salt of piperidine (8).

Scheme IA provides an alternative synthesis for the preparation of compound (4).

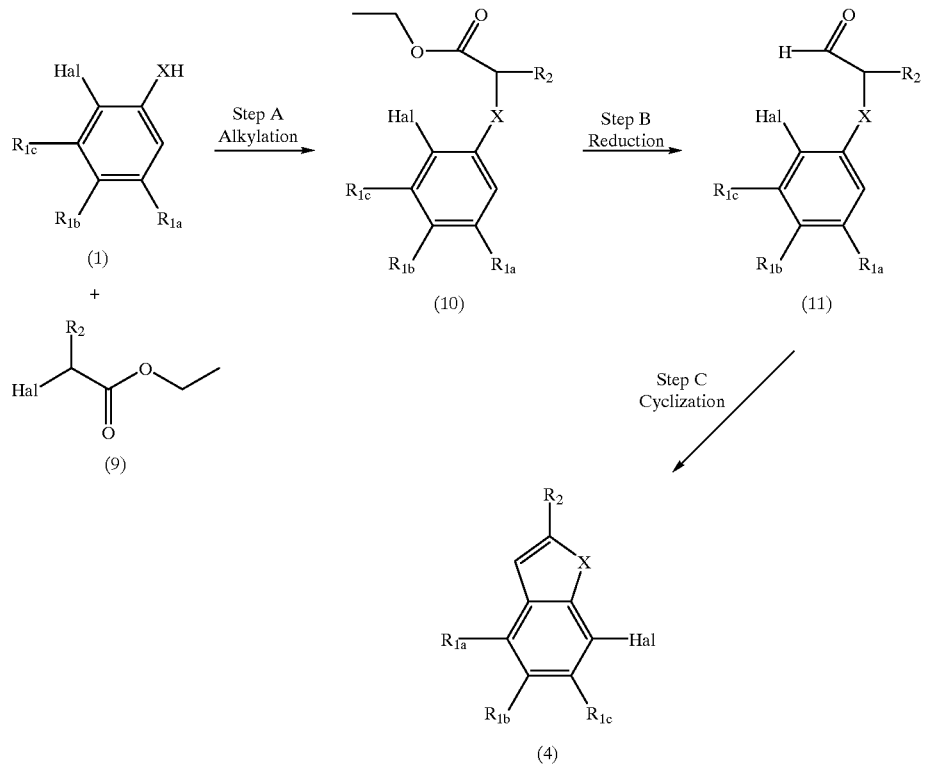

Scheme IA

In Scheme IA, step A, compound (1) is alkylated with a compound of structure (9) in a manner analogous to the procedure described above in Scheme I, step A to provide the alkylated compound of structure (10). As used in Scheme IA, Hal represents Cl, Br or I only, and X represents S, O or NR. For example, compound (1) is dissolved in a suitable organic solvent, such as tetrahydrofuran and a slight excess of a suitable base, such as potassium carbonate. The mixture is then treated with about 1.05 to 1.2 equivalents of compound (9), such as ethyl 2-bromopropionate, and a catalytic amount of potassium iodide, and the reaction is heated at reflux for about 2 to 5 hours. The reaction is then cooled, diluted with water and extracted with a suitable organic solvent, such as ethyl acetate. The organic extracts are combined, dried over anhydrous sodium sulfate, filtered and concentrated under vacuum. The residue is purified by flash chromatography on silica gel with a suitable eluent, such as ethyl acetate/hexane to provide alkylated compound (10).

In Scheme IA, step B, alkylated compound (10) is reduced to the aldehyde of structure (11) under conditions well known in the art. For example, the alkylated compound (10) is dissolved in a suitable organic solvent, such as toluene and cooled to about −78° C. The cooled solution is then treated dropwise with about 1.00 –1.05 equivalents of a suitable reducing agent, such as diisobutylaluminum hydride in toluene. The reaction is then stirred for about 20 to 60 minutes at −78° C. and then quenched with methanol. After warming to room temperature, the reaction is treated with saturated sodium tartrate solution and stirred for about 30 minutes. The mixture is then extracted with a suitable organic solvent, such ethyl acetate. The organic extracts are combined, dried over anhydrous sodium sulfate, filtered and concentrated under vacuum to provide aldehyde (11).

In Scheme IA, step C the aldehyde (11) is cyclized to the compound of structure (4) in a manner analogous to the procedure described above in Scheme I, step B.

Scheme II provides an alternative synthesis of compound (7).

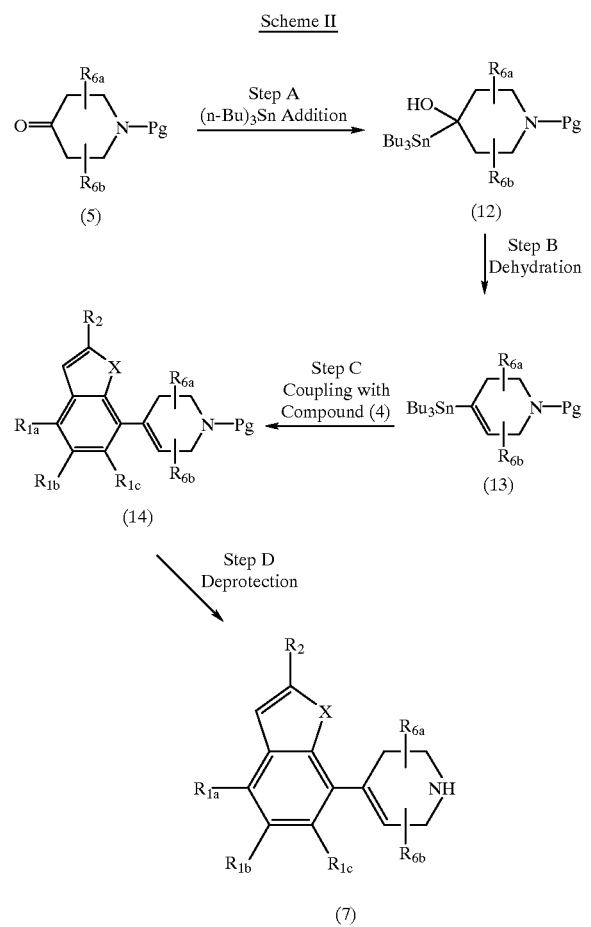

In Scheme II, step A, protected piperidone (5) is converted to the tin derivative (12) under conditions well known in the art. For example, diisopropylamine is dissolved in a suitable organic solvent, such as tetrahydrofuran and the solution is cooled to about 0° C. An equivalent of n-butyllithium is added and the reaction is stirred for about 15 minutes to one hour. Then one equivalent of tri-n-butyltinhydride is added dropwise to the solution, the reaction mixture is stirred for about one hour and then cooled to about −78° C. To this reaction mixture is added dropwise about 0.85 equivalents of the protected piperidone (5) dissolved in tetrahydrofuran. The reaction is then stirred for about 1 to 5 hours at −78° C. and then quenched with buffer (pH 6). The reaction mixture is extracted with a suitable organic solvent, such as ethyl acetate, the organic extracts are combined, dried over anhydrous sodium sulfate, filtered and concentrated under vacuum. The residue is purified by flash chromatography on silica gel with a suitable eluent, such as ethyl acetate/hexane to provide the tin derivative (12).

In Scheme II, step B, tin derivative (12) is dehydrated to the 1,2,3,6-tetrahydropyridine (13) under standard conditions. For example, the tin derivative (12) is dissolved in a suitable organic solvent, such as methylene chloride and the solution is cooled to about 0° C. An excess of triethylamine and about 2.0 equivalents of methanesulfonyl chloride are added to the solution which is allowed to stir for about 4 to 20 hours. The reaction mixture is warmed to room temperature and concentrated under vacuum. The residue is purified by flash chromatography on silica gel with a suitable eluent, such as ethyl acetate/hexane to provide the 1,2,3,6-tetrahydropyridine (13).

In Scheme II, step C the 1,2,3,6-tetrahydropyridine (13) is coupled with compound (4), prepared in Scheme I, to provide the compound of structure (14). For example, one equivalent of compound (4) and one equivalent of 1,2,3,6-tetrahydropyridine (13) are combined in a suitable organic solvent, such as toluene. A catalytic amount of 2,6-di-tert-butyl-4-methylphenol and a catalytic amount of tetrakis (triphenylphosphine)palladium(0) are added and the reaction mixture is heated at reflux for about 15 to 20 hours. The reaction mixture is then cooled, concentrated under vacuum and the residue purified by flash chromatography on silica gel with a suitable eluent, such as ethyl acetate/hexane to provide compound (14).

In Scheme II, step D, compound (14) is deprotected under conditions well known in the art to provide the compound of structure (7). For example, compound (14) is dissolved in a suitable organic solvent, such as toluene and treated with a suitable acid, such a p-toluenesulfonic acid. The reaction is heated at reflux for about 1 to 2 hours, then cooled to room temperature. The mixture is diluted with a suitable organic solvent, such as ethyl acetate, washed with sodium hydroxide solution, the organic layer is dried over anhydrous sodium sulfate, filtered and concentrated to provide compound (7).

Scheme III provides a synthesis of the aldehydes of structure (20).

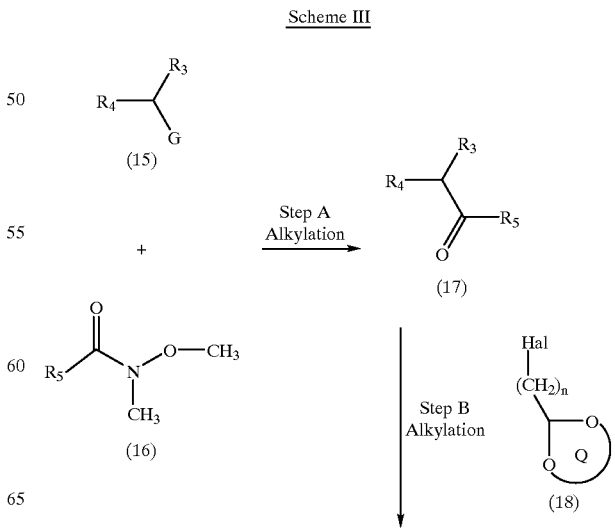

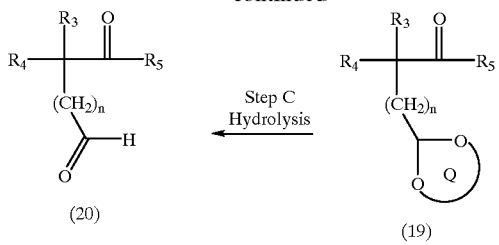

Q is an acyclic or cyclic acetal

In Scheme III, step A, the compound of structure (15) is alkylated with the compound of structure (16) to provide the compound of structure (17) under conditions well known in the art. When G is hydrogen and $R_4$ is 2-pyridyl, 3-pyridyl or 4-pyridyl, for example, then a base, such as n-butyllithium is used to prepare the corresponding anion which is reacted with compound (16). For example, compound (15) is dissolved in a suitable organic solvent, such as tetrahydrofuran and cooled to about −78° C. About 1.1 equivalents of n-buytllithium is added to the cooled solution which is then allowed to warm to room temperature over one hour. The solution is then re-cooled to about −78° C. and treated dropwise with about 1.05 equivalents of a compound of structure (16) dissolved in tetrahydrofuran. [Compounds of structure 16 are readily prepared by one of ordinary skill in the art following generally the procedure disclosed by Brornidge, S. M., et al., *Synthetic Communications*, 23(4), 487–494 (1993).] The reaction is then allowed to warm to room temperature and stirred for about 20 to 40 hours. The reaction mixture is then diluted with water and dilute acid maintaining a pH of about 12. The quenched reaction is then extracted with a suitable organic solvent, such as methylene chloride, the organic extracts are combined, dried over anhydrous sodium sulfate, filtered and concentrated under vacuum. The residue is then purified by flash chromatography on silica gel with a suitable eluent, such as ethyl acetate/hexane to provide the compound (17).

Alternatively, when G is Cl or Br and $R_4$ is aryl, for example, a Grignard reagent is prepared, using techniques and procedures well known in the art, from magnesium in a suitable organic solvent, such as diethyl ether or tetrahydrofuran and refluxing as necessary. The resulting Grignard reagent is then combined with the compound (16) to provide compound (17).

In Scheme III, step B, compound (17) is alkylated with a compound of structure (18) to provide the compound of structure (19) under conditions well known in the art. For purposes of Scheme III, Hal represents Cl, Br or I. For example, compound (17) is dissolved in a suitable organic solvent and treated with a suitable base. Examples of suitable organic solvents are tetrahydrofuran, methyl sulfoxide, dimethylformamide, methyl sulfoxide/tetrahydrofuran, dimethylformamide/tetrahydrofuran, and the like. Examples of suitable bases are potassium tert-butoxide, n-butyllithium, sodium hydride, and the like. For example, compound (17) is dissolved in tetrahydrofuran, and the solution is added dropwise to a cooled suspension (0° C.) of 1.4 equivalents of sodium hydride in tetrahydrofuran. The reaction is warmed to room temperature and stirred for about 2 to 4 hours. Then about 1.5 equivalents of a compound (18) is added to the reaction which is then heated at reflux for about 16 hours. The reaction is then diluted with water, extracted with a suitable eluent, such as diethyl ether, the organic extracts are combined, dried over anhydrous sodium sulfate, filtered and concentrated under vacuum. The residue is purified by flash chromatography on silica gel with a suitable eluent, such as ethyl acetate/hexane to provide compound (19).

In Scheme III, step C, compound (19) is hydrolyzed under conditions well known in the art to provide the aldehyde of structure (20). For example, compound (19) is dissolved in a suitable organic solvent, such as acetone and treated with an excess of a suitable acid, such as 3N HCl. The reaction is stirred at room temperature for about 10 to 20 hours. It is then neutralized with a suitable base, such as 1 N sodium hydroxide. The neutralized mixture is then extracted with a suitable organic solvent, such as ethyl acetate, the organic extracts are combined, dried over anhydrous sodium sulfate, filtered and concentrated under vacuum to provide the aldehyde (20).

Scheme IV provides a synthesis of compounds of formulas Ia through Id. All substituents, unless otherwise specified, are previously defined. The reagents and starting materials are readily available to one of ordinary skill in the art.

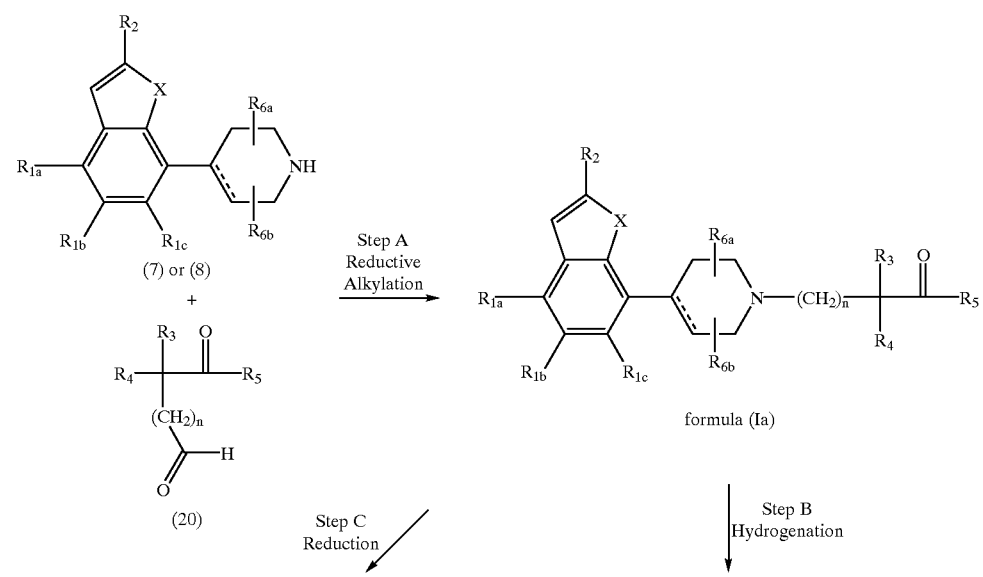

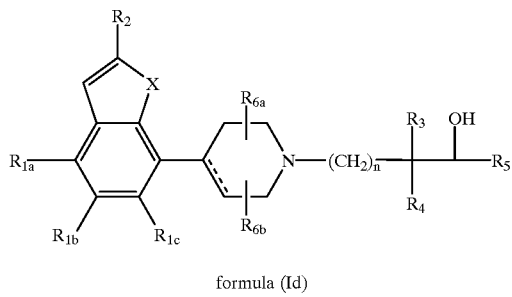

formula (Id)

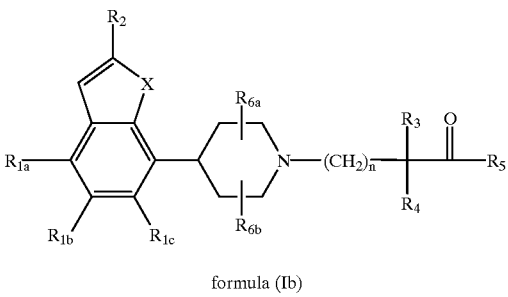

formula (Ib)

Step D
Reduction

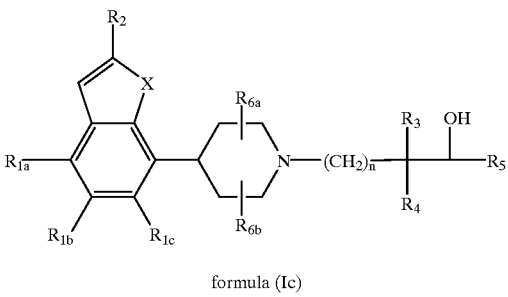

formula (Ic)

In Scheme IV, step A, compounds (7) or (8), prepared in Scheme I above, are subjected to a reductive alkylation with compound (20), prepared in Scheme III above, under conditions well known in the art, such as those disclosed in J. March, "Advanced Organic Chemistry: Reactions, Mechanisms and Structure", $2^{nd}$ Edition, McGraw-Hill, 1978, 819–820, to provide the compound of formula (Ia). For example, in Scheme IV, step A, about one equivalent of either compound (7) or (8) is combined with one equivalent of compound (20) in a suitable organic solvent, such as methylene chloride. To this solution is added about 2.5 equivalents of acetic acid and about 1.3 equivalents of sodium triacetoxyborohydride. The reaction is stirred at room temperature for about 4 to 24 hours and then made basic with 1N sodium hydroxide. The mixture is then extracted with a suitable organic solvent, such as methylene chloride, the combined organic extracts are dried over anhydrous sodium sulfate, filtered and concentrated under vacuum to provide the crude compound of formula Ia. This material can be purified by techniques well known in the art. For example, the crude material is purified by flash chromatography on silica gel with a suitable eluent such as ethyl acetate/hexane. The purified compound of formula Ia can then be converted to the pharmaceutically acceptable salt, such as the oxalate salt by dissolving in methanol and treating with one equivalent of oxalic acid. The solvent is then removed under vacuum to provide the oxalate salt of formula Ia. The oxalate salt can be further purified by recrystallization from suitable organic solvents, such as methylene chloride and hexane.

Alternatively, the crude compound of formula Ia can be purified by direct conversion of the crude free base to the pharmaceutically acceptable salt, such as the oxalate salt, and recrystallized from a suitable organic solvent, such as methylene chloride and hexane.

In Scheme IV, step B, formula Ia is hydrogenated under conditions well known in the art to provide the compound of formula Ib. For example, compound of formula Ia is dissolved in absolute ethanol and treated with 10% palladium on carbon. The reaction is stirred under an atmosphere of hydrogen for about 1 to 24 hours. The reaction is then filtered to remove the catalyst and the filtrate is concentrated under vacuum. The residue is purified by techniques well known in the art, such as those described in step A above to provide the compound of formula Ib as either the free base or a pharmaceutically acceptable salt.

In Scheme IV, step D, formula Ib is further reduced under conditions well known in the art to provide the compound of formula Ic. For example, the compound of formula Ib is dissolved in a suitable organic solvent such as methylene chloride, cooled to about −78° C. and treated with a suitable reducing agent, such as about 3 equivalents of diisobutylaluminum hydride or lithium aluminum hydride. The reaction is then slowly warmed to room temperature over about 2 hours and then stirred at room temperature for about 16 hours. The reaction is then diluted with saturated aqueous potassium sodium tartrate solution and extracted with methylene chloride. The organic extracts are combined, dried over anhydrous sodium sulfate, filtered and concentrated under vacuum. The residue is purified by flash chromatography on silica gel with a suitable eluent, such as ethyl acetate/hexane to provide the free base of the compound of formula Ic. As described above in step A, this free base can then be converted to the pharmaceutically acceptable salt, such as an oxalate salt.

In Scheme IV, step C the compound of formula Ia is reduced to the compound of formula Id in a manner analogous to the procedure described above in step D. In addition, the free base of formula Id is converted to the pharmaceutically acceptable salt in a manner analogous to the procedure described in step A above.

Scheme V provides a synthesis of the compound of formula Ie. Reagents and starting materials are readily available to one of ordinary skill in the art. All substituents are previously defined, unless otherwise indicated.

Scheme V

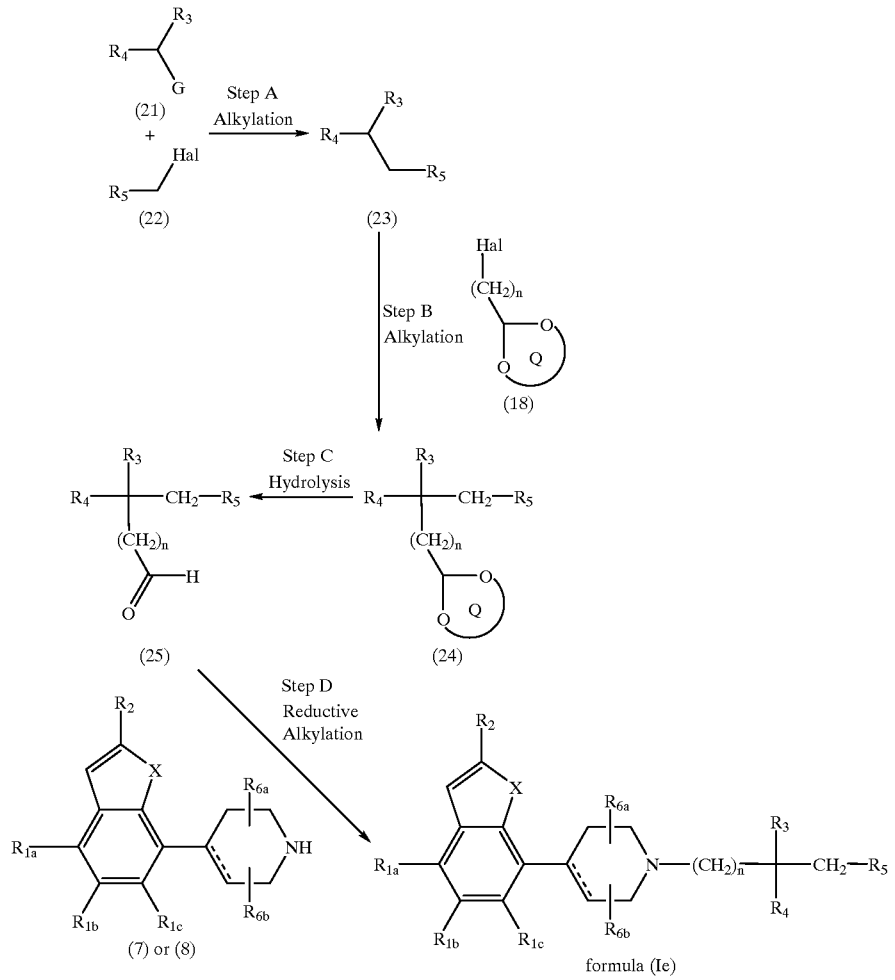

Q is an acylic or cyclic acetal

In Scheme V, step A, a compound of structure (21) is alkylated with a compound of structure (22) under conditions well known in the art to provide the compound of structure (23). When G is hydrogen and $R_4$ is 2-pyridyl, 3-pyridyl or 4-pyridyl, for example, then a base, such as n-butyllithium is used to prepare the corresponding anion which is reacted with compound (22). For example, compound (21) is dissolved in a suitable organic solvent, such as THF and treated with a suitable base, such as n-butyllithium at about −78° C. The mixture is warmed to room temperature and then cooled back down to −78° C. and treated with about 1.05 equivalents of a compound (22), wherein for the purposes of Scheme V, Hal represents Cl, Br or I. The reaction is warmed to room temperature and allowed to stir for 10 to 20 hours. It can then be heated to reflux for about 2 to 24 hours and then cooled to room temperature. The solvent is then removed under vacuum, the residue dissolved in a suitable organic solvent, such as ethyl acetate, followed by addition of water. The layers are separated, and the aqueous is extracted with ethyl acetate. The organic extracts are combined, dried over anhydrous magnesium sulfate, filtered and concentrated under vacuum. The residue is purified by flash chromatography on silica gel with a suitable eluent, such as ethyl acetate/hexane to provide compound (23).

Alternatively, when G is Cl or Br and $R_4$ is aryl, for example, a Grignard reagent is prepared, using techniques and procedures well known in the art, from magnesium in a suitable organic solvent, such as diethyl ether or tetrahydrofuran and refluxing as necessary. The resulting Grignard reagent is then combined with the compound (22) under standard conditions to provide compound (23). Additional conditions for coupling of alkyl halides with organometallic reagents, can be found in J. March, "Advanced Organic Chemistry: Reactions, Mechanisms and Structure", 2nd Edition, McGraw-Hill, 1978, pages 409–412.

In Scheme V, step B, compound (23) is alkylated with compound (18) in a manner analogous to the procedure described in Scheme III, step B to provide the compound of structure (24). As used herein, Hal represents Cl, Br or I only.

In Scheme V, step C, compound (24) is hydrolyzed under acidic conditions in a manner analogous to the procedure described in Scheme III, step C to provide the aldehyde of structure (25).

In Scheme V, step D, compound (25) is used to reductively alkylate with compound (7) [prepared in Scheme I or II above] or compound (8) [prepared in Scheme I above], in a manner analogous to the procedure described in Scheme IV, step A to provide the compound of formula Ie.

Compounds wherein X is S(=O) or S(=O)$_2$ in formula I are readily prepared by one of ordinary skill in the art using well known techniques and procedures. For example, compounds of formulas Ia–Ie wherein X is S can be oxidized under standard conditions, such as treatment with m-chloroperbenzoic acid, to provide the corresponding sulfone [S(=O)$_2$] or sulfoxide [S(=O)].

Intermediate aldehyde of structure (20a) can be prepared as described in Scheme VI below. Aldehyde (20a) is reductively aminated in a manner analogous to aldehyde (20) to provide compound of formula I. The reagents and starting materials are readily available to one of ordinary skill in the art.

Scheme VI

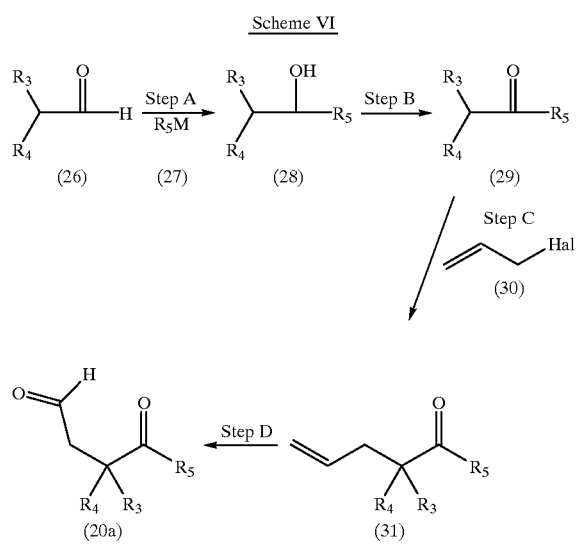

In Scheme VI, step A, aldehyde (26) is combined with a suitable organometallic reagent (27) under conditions well known in the art to provide alcohol (28). Examples of suitable organometallic reagents include Grignard Reagents, alkyl lithium reagents, and the like. Grignard Reagents are preferred. For examples of typical Grignard Reagents and reaction conditions, see J. March, "Advanced Organic Chemistry: Reactions, Mechanisms, and Structure", 2nd Edition, McGraw-Hill, pages 836–841 (1977). More specifically, aldehyde (26) is dissolved in a suitable organic solvent, such as tetrahydrofuran, cooled to about –5° C. and treated with about 1.1 to 1.2 equivalents of a Grignard reagent of formula (27) wherein M is MgCl or MgBr. The reaction is allowed to stir for about 1 to 2 hours, then quenched, and alcohol (28) is isolated. For example, the reaction mixture is poured onto ice-cold 1N HCl, the quenched mixture is extracted with a suitable organic solvent, such as toluene, the organic extracts are dried over anhydrous magnesium sulfate, filtered and concentrated under vacuum to provide alcohol (28).

In Scheme VI, step B, alcohol (28) is oxidized under standard conditions well know in the art, such as those described by J. March, "Advanced Organic Chemistry: Reactions, Mechanisms, and Structure", 2nd Edition, McGraw-Hill, pages 1082–1084 (1977), to provide ketone (29).

For example, alcohol (28) is dissolved in a suitable organic solvent, such as methylene chloride, the solution cooled with a wet ice-acetone bath, and treated with 2.5 to 3.0 equivalents of dimethyl sulfoxide. After stirring for about 30 minutes, the reaction is then treated with about 1.8 equivalents of P2O5. The reaction is allowed to stir for about 3 hours and then is treated over about 30 minutes with about 3.5 equivalents of a suitable amine, such as triethylamine. The cooling bath is then removed and the reaction is allowed to stir for about 8 to 16 hours. The ketone (29) is then isolated by standard extraction techniques well known in the art.

In Scheme VI, step C, ketone (29) is treated with a suitable base followed by addition of the alkene (30), wherein X is a suitable leaving group, to provide compound (31). For example, ketone (29) is combined with an excess of alkene (30) in a suitable organic solvent, such as tetrahydrofuran, and cooled with a wet ice acetone bath. Examples of suitable leaving groups are Cl, Br, I, and the like. Preferred leaving groups are Cl and Br. About 1.1 equivalents of a suitable base, such as potassium tert-butoxide, is added and the reaction is allowed to stir for about 2 hours at room temperature. The reaction is then quenched with aqueous acid and compound (31) is isolated by extraction with heptane. The heptane extracts are washed with sodium bicarbonate, dried over anhydrous magnesium sulfate, filtered and concentrated under vacuum to provide compound (31).

In Scheme VI, step D, compound (31) is treated with a suitable oxidizing agent to provide aldehyde (20a). Ozone is the preferred oxidizing agent. Examples of suitable oxidizing reagents and conditions are described by J. March, "Advanced Organic Chemistry: Reactions, Mechanisms, and Structure", 2nd Edition, McGraw-Hill, pages 1090–1096 (1977).

For example, compound (31) is dissolved in a suitable organic solvent, such as methanol, a small amount of Sudan III is added, and the solution is cooled to about –20° C. Ozone is bubbled into the solution for about 4 hours until the pink color turns to a pale yellow color. Then Me$_2$S is added to the reaction mixture and the cooling bath is removed. Concentration of the reaction mixture under vacuum provides the intermediate dimethyl acetal of aldehyde (20a). This dimethyl acetal is readily hydrolyzed under standard acidic conditions to provide aldehyde (20a). Alternatively, direct acidic work-up of the crude reaction mixture provides aldehyde (20a).

The compounds of formulas If, Ig, Ih and Ij can be prepared as described in Scheme VII. The reagents and starting materials are readily available to one of ordinary skill in the art. Unless otherwise specified, the substituents are as previously defined.

Scheme VII

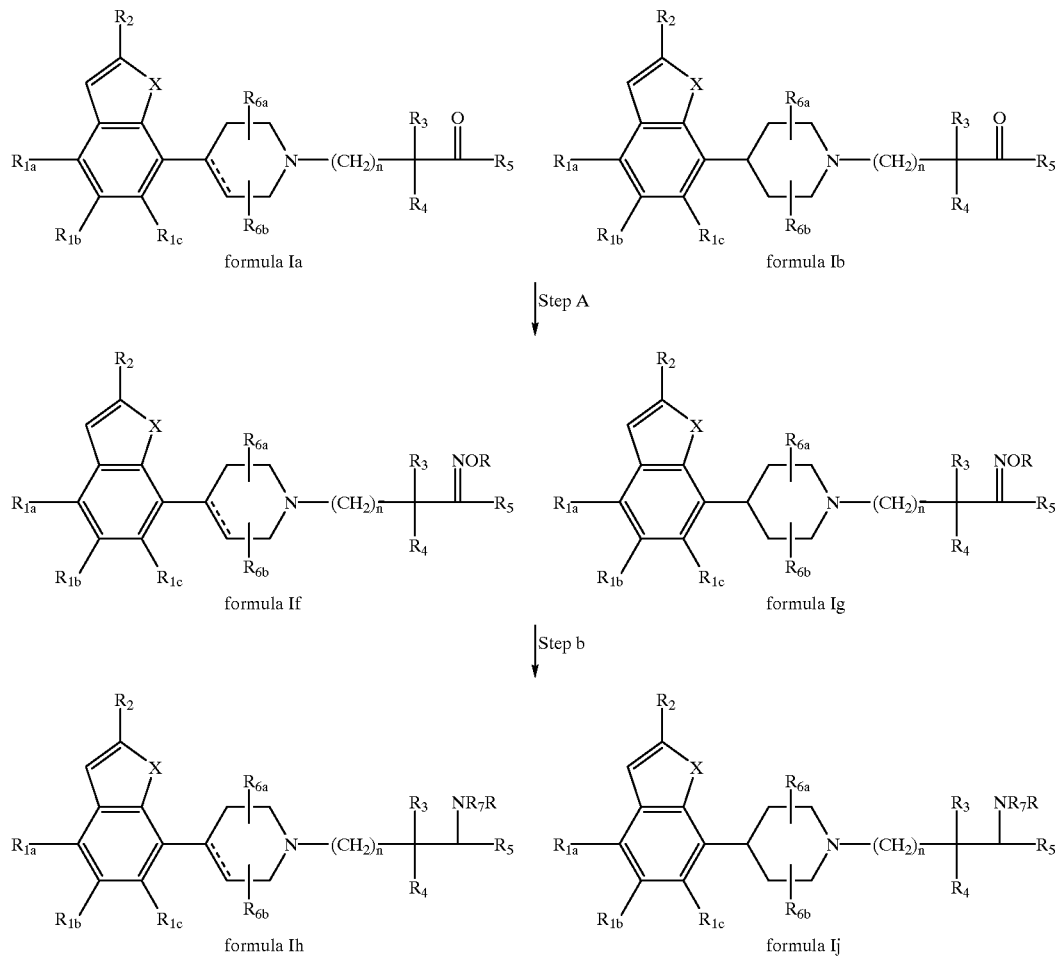

In Scheme VII, step A, the compounds of formula Ia or formula Ib are converted to the corresponding oxime of formulas If and Ig under conditions well known in the art. For example, the compounds of formula Ia or Ib are dissolved in a suitable solvent or solvent mixture, such as ethanol/water and treated with an excess of a suitable hydroxylamine, such as hydroxylamine hydrochloride. The reaction mixture is heated at reflux for 16 to 24 hours and then the compounds of formulas If and Ig are isolated and purified using standard techniques and procedures, such as extraction techniques and flash chromatography. For example, the cooled reaction is diluted with a suitable organic solvent, such as ethyl acetate, the organic layer is separated, washed with water, dried over anhydrous sodium sulfate, filtered and concentrated under vacuum to provide the crude oximes. The crude material can then be purified by flash chromatography on silica gel with a suitable eluent, such as methanol/ethyl acetate to provide the purified compounds of formulas If and Ig.

In Scheme VII, step B compounds of formulas If and Ig are reduced under standard conditions to provide the amines of formulas Ih and Ij. For example, the compounds of formula If or Ig are dissolved in a suitable organic solvent, such as diethyl ether and treated with a suitable reducing agent, such as lithium aluminum hydride. The reaction is stirred at a temperature of about room temperature to reflux for about 3 to 24 hours. The reaction is then quenched with 1N sodium hydroxide and the desired compounds of formulas Ih and Ij are isolated and purifed using standard techniques and procedures. For example, the quenched reaction mixture is extracted with a suitable organic solvent, such as ethyl acetate, the organic extracts are combined, dried over anhydrous sodium sulfate, filtered and concentrated under vacuum to provide the crude material. The crude material is then purified by flash chromatography on silica gel with a suitable eluent, such as methanol/methylene chloride with ammonia added to provide the purified compounds of formulas Ih and Ij. The free bases are converted to the corresponding pharmaceutically acceptable salts using standard procedures well known to one of ordinary skill in the art.

The following examples represent typical syntheses of the compounds of formula I as described generally above. These examples are illustrative only and are not intended to limit the invention in any way. The reagents and starting materials are readily available to one of ordinary skill in the art. As used herein, the following terms have the meanings indicated: "eq" refers to equivalents; "g" refers to grams; "mg" refers to milligrams; "L" refers to liters; "mL" refers to milliliters; "µL" refers to microliters; "mol" refers to moles; "mmol" refers to millimoles; "psi" refers to pounds per square inch; "min" refers to minutes; "h" refers to hours; "°

C." refers to degrees Celsius; "TLC" refers to thin layer chromatography; "HPLC" refers to high performance liquid chromatography; "R$_f$" refers to retention factor; "R$_t$" refers to retention time; "δ" refers to part per million down-field from tetramethylsilane; "THF" refers to tetrahydrofuran; "DMF" refers to N,N-dimethylformamide; "DMSO" refers to methyl sulfoxide; "LDA" refers to lithium diisopropylamide; "aq" refers to aqueous; "iPrOAc" refers to isopropyl acetate; "EtOAc" refers to ethyl acetate; "EtOH" refers to ethyl alcohol; "MeOH" refers to methanol; "MTBE" refers to tert-butyl methyl ether; "TMEDA" refers to N,N,N',N'-tetramethylethylenediamine, and "RT" refers to room temperature.

PREPARATION 1

Preparation of N-Benzyl-3,3-dimethyl-4-piperidone

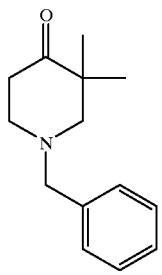

In a 1 liter 3-necked flask equipped with mechanical stirring, addition funnel and a calcium chloride drying tube is added a 37% weight solution of formaldehyde (168.5 mL, 2.25 mole) dissolved in 500 mL of absolute ethanol. The resulting solution was cooled in an ice-water bath to 10° C., and benzylamine (109 mL, 1 mole) was added dropwise over a one hour period. In a separate 3 liter 3-necked flask equipped with mechanical stirring, addition funnel and two condensers is added 3-methyl-2-butanone (113 mL, 1.06 mole) dissolved in 500 ml of absolute ethanol and concentrated hydrogen chloride (92 mL, 1.11 mole). The resulting solution is brought to reflux and the formaldehyde/benzylamine solution is added dropwise over a 2 hour period. This solution is refluxed overnight, and then cooled to ambient temperature. Diisopropylethylamine (142.2 g, 1.1 mole) and formaldehyde (22.46 mL, 0.3 mole) are added and the resulting solution is heated to reflux for six hours, and then cooled to ambient temperature. The solution was quenched with potassium hydroxide (61.6 g, 1.1 mole) in 200 mL of water, and then extracted with 500 ml ethyl acetate three times. The organics were concentrated under vacuum to give 225 g of red oil. The crude oil was dissolved in 1 liter of methylene chloride. This solution was carefully poured over 1 kg of silica gel on a sintered glass filter. The silica gel was washed with 4 L of methylene chloride. The methylene chloride was concentrated under vacuum to provide 142 g of a yellow oil which crystallizes in the freezer overnight. Yield=65.4%.

MS(ion spray)=218.3(M+1).

PREPARATION 2

Preparation of 1-N-Benzyl-4-hydroxy-4-(2'-(2",2"-O-diethoxy)ethylthiophenyl)piperidine

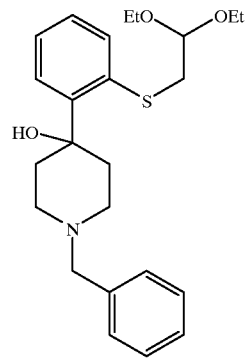

A 3 L flask containing 238 mL TMEDA (183.8g, 1.575 mmol) was purged with nitrogen at 5° C. for 10 minutes and n-BuLi (2M in cyclohexane, 786.5 mL, 1.537 mole) was added via addition funnel. A mild exotherm and some yellowish precipitate were observed. The addition funnel was rinsed clean with 125 mL of cyclohexane (dried over 4A molecular sieves and purged with nitrogen). Thiophenol (750 mmol, 82.7 g, 77.30 mL) in 45 mL of cyclohexane was added at such a rate so as to keep the temperature below 22° C., with the aid of an ice bath and vigorous stirring. The reaction mixture turned clear after 10 mL of the thiophenol solution was added, and remained so during the course of the addition which lasted 50 minutes. The solution was stirred at room temperature (22° C.) and turned cloudy after 2 h. After stirring for another 20 h at ambient temperature, the off-white suspension was cooled to −5° C., mixed with 500 mL of THF (sieve dried, nitrogen purged), stirred at −5° C. for 20 minutes, and then cooled to −60° C. N-benzyl-4-piperidone (distilled, 139.86 g, 740 mmol) in 250 mL of THF was added dropwise within 50 minutes, while keeping the reaction temperature below −50° C. The resulting yellow suspension was stirred at −60° C. for 20 minutes, then allowed to warm to ambient temperature within 2 h to give a clear solution. Diethyl bromoacetal (149.7 g, 760 mmol) was added, and the resulting solution was heated to reflux at 76° C. for 3 h. Then with continuous heating, 1300 mL of solvents were distilled off, while the temperature reached 100° C. After heating at 100° C. for another 2 h, the solution was cooled to 22° C., mixed with 700 mL of toluene and an equal volume of water (exotherming to 35° C.). The aqueous layer was extracted with toluene (300 mL×3, and the combined organic layers were washed with water (300 mL×4) and brine (300 mL×2) to give a toluene solution of title compound and by-product and residual solvent. The wet toluene solution was dried over anhydrous MgSO$_4$, vacuum filtered, and concentrated to afford 345.0 g of crude title compound as an amber oil. The oil was seeded with crystals from previously made title compound, and the flask was cooled in an ice bath. Recrystallization was slow so leaving the mixture standing overnight was necessary. The title compound crystallized into a solid mass. Heptane (308 mL) was added to the mixture and the solid was broken up with a spatula. The mixture slurry was cooled in an ice bath with stirring for 3 h, vacuum filtered, washed with 100 mL of cold (about −22° C.) heptane, and air dried to afford 173.93 g (56.555%) of title compound as a beige solid.

PREPARATION 3

Preparation of N-Benzyl-4-(benzo[b]thiophene-7-yl)-1,2,3,6-tetrahydropyridine Hydrochloride

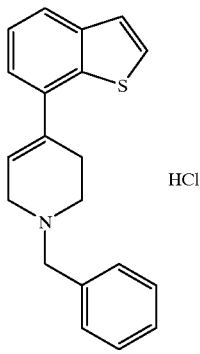

A solution of 1.00 g (0.00241 mol) of 1-N-benzyl-4-hydroxy-4-(2'-(2",2"-O-diethoxy)ethylthio-phenyl)piperidine (prepared in preparation 2) in 20 mL of toluene was added dropwise to 20 mL of 6 N HCl (aq) at reflux. Washings with 20 mL of toluene was added all at once. Water was added after 1 h to replenish the aqueous phase. After heating for 3 h, the mixture was cooled to room temperature and the title compound, as a white solid, was vacuum filtered, washed with 20 mL of THF and air dried to afford 0.18 g (22%) of title compound as a white solid.

The filtrate was neutralized with 6.00 g of $NaHCO_3$, 40 mL of 10% $NaHCO_3$ (aq) (pH=8), and extracted with 20 mL of toluene. The organic phase was saved. The aqueous phase was extracted with a solution of 20 mL of THF and 20 mL of toluene, and then with 20 mL of THF. The organic phases were combined, washed with 25 mL of 25% NaCl (aq), dried over anhydrous $MgSO_4$, gravity filtered, and concentrated to afford 0.69 g of crude free base of the title compound.

The crude free base of the title compound was purified by gel filtration (silica gel 60; 9:1 hexane: EtOAc) to afford 0.26 g (35%) of free base of the title compound. Total yield was 57%.

PREPARATION 4

Preparation of N-Benzyl4-hydroxy-(benzo[b]thiophene-7-yl)-piperidine

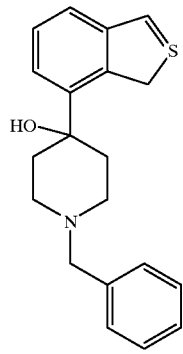

A 3-neck 500 mL roundbottom flask fitted with a condenser, dropping funnel and nitrogen purge, was charged with toluene (600 mL) and methanesulfonic acid (202 mL, 300 g, 6.5 eq). The mixture was heated to 45–55° C., and 1-N-benzyl-4-hydroxy-4-(2'-(2",2"-O-diethoxy)ethylthiophenyl)piperidine (200 g, 481.4 mmol) dissolved in toluene (1400 mL) was added over approximately 30 minutes maintaining the temperature at 45–50° C. The reaction mixture was stirred for about 1 to 2 hours at 45–55° C. and then quenched with a mixture of 2N sodium hydroxide (1685 mL, 7 eq) and isopropyl alcohol (400 mL). The layers were separated and the organic phase was washed with water (1000 mL). Approximately 800 mL of solvent were removed under vacuum (less than 100 mm Hg) and silica G60 (160 g) was added. The mixture was then stirred for at least 30 minutes at room temperature. The mixture was then filtered and the silica G60 was rinsed with toluene (1000 mL). The filtrate was concentrated under vacuum (less than 100 mm Hg) to a final pot volume of about 400 mL. The title compound could then be isolated by complete concentration under vacuum or, alternatively, it is allowed to remain in the toluene and carried on to the dehydration step.

PREPARATION 5

Alternative Preparation of N-Benzyl-4-(benzo[b]thiophene-7-yl)-1,2,3,6-tetrahydropyridine Hydrochloride The toluene solution from example 3 containing the compound prepared in preparation 4 was diluted with isopropyl alcohol (1000 mL) and heated to 60° C. Then 2.5 M HCl/isopropanol (212 mL, 1.1 eq) was added over 30 minutes. The reaction mixture was then cooled in an ice bath and stirred for at least one hour at 0° C. The cooled mixture was then filtered, the solid rinsed with cold isopropyl alcohol and dried under vacuum at 50° C. to provide the title compound (55–60%) as the HCl salt.

PREPARATION 6

Preparation of 1-N-Carbethoxy-4-hydroxy-4-(2'-(2",2"-O-diethoxy)ethylthiophenyl)piperidine

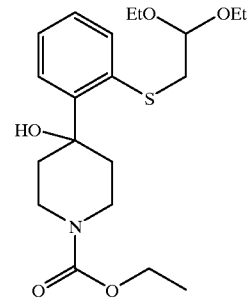

A solution of 2.0M of n-BuLi in cyclohexane (11.99 mL, 24 mmol) was cooled to 5° C. under a nitrogen atmosphere. TMEDA (3.71 mL, 24.6 mmol) was added dropwise keeping the exotherm under 10° C. Thiophenol (1.20 mL, 11.7 mmol) in 2 mL cyclohexane was added dropwise keeping the exotherm under 20° C. The resulting solution was allowed to stir to ambient temperature overnight. The thick white slurry was cooled to −50° C., and diluted with 2 mL of dry THF. A solution of 1-carbethoxy-4-piperidone (2.0 g, 11.7 mmol) in 1 mL of dry THF was added dropwise keeping the exotherm less than −50° C. The resulting solution was warmed to ambient temperature and stirred for 2 hours. Bromo acetaldehyde diethyl acetal (1.78 mL, 11.82 mmol) was added all at once, and the resulting solution was heated at reflux for 4 hr. The solution was cooled to ambient temperature, quenched with pH=7 buffer (50 mL), and extracted with ethyl acetate (3×50 mL). The combined organics were absorbed on silica gel, and purified using silica gel flash chromatography to provide the title compound (3.30 g) as a colorless oil.

PREPARATION 7

Preparation of N-Carbethoxy-4-(benzo[b]thiophene-7-yl)-1 2,3,6-tetrahydropyridine

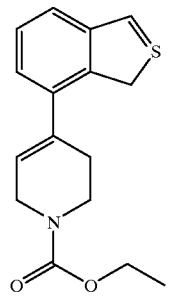

A solution of methanesulfonic acid (0.98 mL, 15.11 mmol) in 5 mL toluene was cooled to 0° C. To this solution was added 1-N-carbethoxy-4-hydroxy-4-(2'-(2",2"-O-diethoxy)ethylthio-phenyl)piperidine (1.0 g, 2.52 mmol) in 5 mL of toluene dropwise at 0° C. The solution was then stirred at 10° C. for 15 minutes, and slowly warmed to ambient temperature. After the starting material disappeared by TLC, the reaction was quenched with a saturated solution of sodium bicarbonate and extracted with ethyl acetate (3×25 mL). The organics were dried over anhydrous magnesium sulfate, filtered and purified over silica gel (ethyl acetate/hexane, 1:1) to provide the title compound (123 mg) as a light yellow oil.

PREPARATION 8

Preparation of 4-(Benzo[b]thiophene-7-yl)-1,2,3,6-tetrahydropyridine

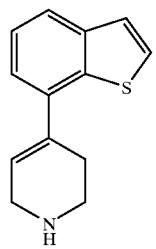

Dissolve N-carbethoxy-4-(benzo[b]thiophene-7-yl)-1,2,3,6-tetrahydropyridine (105 mg, 0.3652mmol) in 1 mL ethylene glycol and add potassium hydroxide (102 mg, 1.826 mmol) dissolved in 1 mL of water. The reaction mixture is heated at reflux for 8 hours and then cooled to room temperature. It is then diluted with 5 mL water and extracted with ethyl acetate (3×5 mL), dried over anhydrous magnesium sulfate, filtered and concentrated under vacuum. The reside is purified over silica gel to provide the title compound as a yellow oil (51 mg), MS(ion spray)=216.3 (M+1).

EXAMPLE 1

Preparation of 4-(7-Benzo(b)thiophene-1,2,3,6-tetrahydropyridyl)-1-cyclohexyl-2-(2-pyridyl)butan-1-one Oxalate

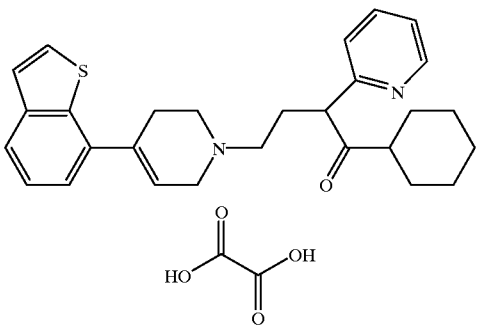

Preparation of 2-(2-Bromophenylthio)acetaldehyde Diethyl Acetal

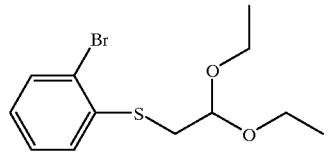

Scheme I, step A: A 500 mL round bottom flask was charged with anhydrous DMF (100 mL), 2-bromothiophenol (10.0 g, 52.88 mmol), potassium carbonate (11.0 g, 79.59 mmol) and bromoacetaldehyde diethyl acetal (8.35 mL, 55.5 mmol). The reaction was stirred at room temperature for 5 hours. Water (50 mL) and ethyl acetate (100 mL) were then added with mixing. The layers were separated and the organic layer was washed with water (5×50 mL), dried over anhydrous sodium sulfate, filtered and concentrated under vacuum to provide 2-(2-bromophenylthio)acetaldehyde diethyl acetal (13.78 g, 85%).

Preparation of 7-Bromobenzo(b)thiophene

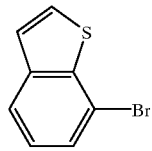

Scheme I, step B: Chlorobenzene (100 mL) and polyphosphoric acid (30.4 g, PPA) were combined and heated to reflux. The 2-(2-bromophenylthio)acetaldehyde diethyl acetal (13.7 g, 44.88 mmol, Scheme I, step A above) dissolved in chlorobenzene (20 mL) was added dropwise to the refluxing mixture over 20 minutes. The reaction was refluxed for 4 hours and then cooled. The solvent was decanted from the residue and toluene (2×50 mL) was added to the residue, stirred and decanted. The toluene extracts were concentrated under vacuum and the residue taken up in ethyl acetate and water. The organic phase was washed with saturated sodium bicarbonate, dried over anhydrous sodium sulfate, filtered and concentrated to provide 7-bromobenzo(b)thiophene (8.91 g, 93%).

Preparation of 1-(t-Butoxycarbonyl)-4-(7-benzo(b)thiophene)-4-hydroxy Piperidine

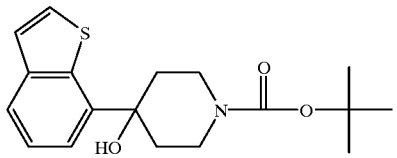

Scheme I, step C: 7-bromobenzo(b)thiophene (3.01 g, 14.1 mmol, prepared above in step B) was dissolved in diethyl ether (20 mL) and the solution was added dropwise to a suspension of magnesium (0.69 g, 28.3 mmol) in diethyl ether (20 mL). Dibromoethane (1.22 mL, 14.1 mmol) in diethyl ether (10 mL) was then added dropwise to the reaction mixture, which was then heated to reflux for 3 hours. The reaction was then cooled to room temperature and 1-(t-butoxycarbonyl)-4-piperidone (2.81 g, 14.1 mmol) was added. The reaction was stirred overnight at room temperature. Water was then added to the reaction, and the mixture was extracted with diethyl ether. The organic layers were combined, dried over anhydrous sodium sulfate, filtered and concentrated under vacuum. The residue was purified by flash chromatography (hexane:ethyl acetate, 7:3, silica gel) to provide 1-(t-butoxycarbonyl)-4-(7-benzo(b)thiophene-4-hydroxy piperidine (1.14 g).

Preparation of 7-Benzo(b)thiophene-1,2,3,6-tetrahydropyridyl

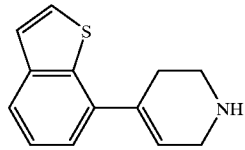

Scheme I, step D: 1-(t-butoxycarbonyl)-4-(7-benzo(b)thiophene-4-hydroxy piperidine (1.15 g, 3.45 mmol, prepared above in step C) was combined with toluene (50 mL) and p-toluenesulfonic acid (1.64 g, 9 8.63 mmol). The mixture was heated to reflux for 2 hours and then cooled. The reaction mixture was made basic with 1N sodium hydroxide and then extracted with ethyl acetate. The organic extracts were combined, dried over anhydrous sodium sulfate, filtered and concentrated under vacuum to provide 7-benzo(b)thiophene-1,2,3,6-tetrahydropyridyl (0.67 g).

Alternative Preparation of 7-Benzo(b)thiophene-1,2,3,6-tetrahydropyridyl

Preparation of 1-(t-Butoxycarbonyl)-4-hydroxy-4-tributylstannyl Piperidine

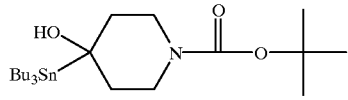

Scheme II, step A: Diisopropylamine (25.2 mL, 0.18 mol) in anhydrous THF (500 mL) was cooled to 0° C. and n-butyllithium (112.5 mL of a 1.6 M solution in THF, 0.18 mol) was added dropwise over 20 minutes to the cooled solution. The reaction mixture was stirred for an additional 15 minutes at 0° C. and then tri-n-butyltinhydride (48.4 mL, 0.18 mol) was added dropwise over 30 minutes. The reaction mixture was then stirred for one hour and then cooled to −78° C. N-(t-butoxycarbonyl)-4-piperidone (30.0 g, 0.15 mol) in THF (500 mL) was then added dropwise to the cooled solution over one hour. After addition was complete, the reaction was stirred for 2 hours at −78° C. and then quenched with buffer (pH 6). The mixture was extracted with ethyl acetate, the organic extracts were combined, dried over anhydrous sodium sulfate, filtered and concentrated under vacuum. The residue was purified by flash chromatography (5% ethyl acetate/hexane to provide 1-(t-butoxycarbonyl)-4-hydroxy4-tributylstannyl piperidine (36.06g).

Preparation of 1-(t-Butoxycarbonyl)-4-tributylstannyl-1,2,3,6-tetrahydropyridyl

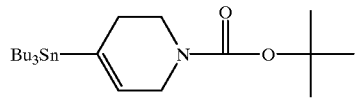

Scheme II, step B: 1-(t-butoxycarbonyl)-4-hydroxy-4-tributylstannyl piperidine (36.0 g, 73.4 mmol, prepared in Scheme II, step A above) was dissolved in methylene chloride (250 mL) and cooled to 0° C. Triethylamine (30.7 mL, 220 mmol) and methanesulfonyl chloride (8.56 mL, 110 mmol) were added to the solution which was warmed to room temperature and allowed to stir for 4 hours. An additional amount of methanesulfonyl chloride (4.28 mL) and triethylamine (15.3 mL) was added and the reaction was allowed to stir for an additional hour at room temperature. The reaction mixture was then stored in a freezer overnight. The crude reaction mixture was then concentrated under vacuum. The residue was then purified by flash chromatography (5% ethyl acetate/hexane, silica gel) to provide 1-(t-Butoxycarbonyl)-4-tributylstannyl-1,2,3,6-tetrahydropyridyl (24.75 g, 79%).

Preparation of 1-(t-Butoxycarbonyl)-4-(7-benzo(b)thiophene)-1,2,3,6-tetrahydropyridyl

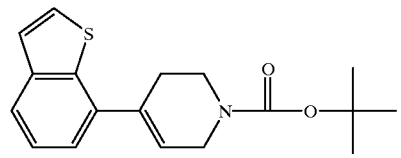

Scheme II, step C: 7-bromobenzo(b)thiophene(0.25 g, 1.17 mmol) and 1-(t-butoxycarbonyl)-4-tributylstannyl-1,2,3,6-tetrahydropyridyl (0.55 g, 1.17 mmol, prepared in Scheme II, step B above), 2,6-di-tert-butyl-4-methylphenol (25 mg) and tetrakis(triphenylphosphine)palladium(0) (0.046 g, 0.04 mmol) were combined in toluene (10 mL). The reaction mixture was heated to reflux for 16 hours. It was then cooled, filtered and concentrated to provide an orange oil which was purified by flash chromatography (5% ethyl acetate/hexane, silica gel) to provide 1-(t-butoxycarbonyl)-4-(7-benzo(b)thiophene)-1,2,3,6-tetrahydropyridyl (0.227 g, 61%).

Preparation of 7-Benzo(b)thiophene-1,2,3,6-tetrahydropyridyl

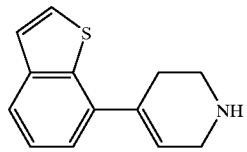

Scheme II, step D: 1-(t-butoxycarbonyl)-4-(7-benzo(b)thiophene)-1,2,3,6-tetrahydropyridyl (0.23 g, 0.73 mmol) was combined with p-toluenesulfonic acid in toluene (10 mL) and heated to reflux for one hour. The reaction was cooled to room temperature and diluted with ethyl acetate (50 mL). The mixture was then washed with 1 N sodium hydroxide (3×20 mL), the organic layer was dried over anhydrous sodium sulfate, filtered and concentrated under vacuum to provide 7-benzo(b)thiophene-1,2,3,6-tetrahydropyridyl (0.14 g, 96%).

Preparation of 1-Cyclohexyl-2-(2-pyridyl)ethan-1-one

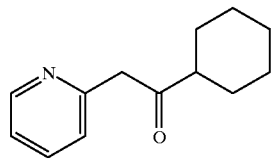

Scheme III, step A: A 100 mL round bottom flask was charged with 2-picoline (1.09 mL, 11.02 mmol) and anhydrous THF (15 mL). The solution was cooled to −78° C. and n-butyllithium (7.6 mL of a 1.6M solution in THF, 12.12 mmol) was added dropwise to the cooled solution. After addition was complete, the reaction mixture was warmed to room temperature over one hour and then cooled again to −78° C. N-methoxy-N-methyl cyclohexyl amide (2.0 g, 11.68 mmol) in THF (10 mL) was added dropwise to the reaction mixture. After addition was complete, the reaction was warmed to room temperature over one hour and then stirred for 40 hours. The reaction mixture was then treated with water and 1N HCl (keeping the pH at approximately 12). The reaction mixture was then extracted with methylene chloride (3×20 mL). The organic extracts were combined, dried over anhydrous sodium sulfate, filtered and concentrated under vacuum to provide an orange oil which was purified by flash chromatography (ethyl acetate:hexane, 3:7, silica gel) to provide 1-cyclohexyl-2-(2-pyridyl)ethan-1-one (2.06 g).

Preparation of 1-Cyclohexyl-3-(2-(1,3-dioxolane))-2-(2-pyridyl)propan-1-one

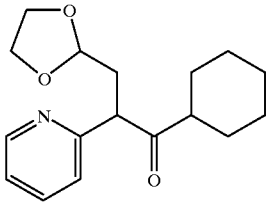

Scheme III, step B: A 250 mL round bottom flask was charged with anhydrous DMF (30 mL) and sodium hydride (0.56 g of a 60% dispersion, 14.0 mmol). The suspension was cooled to 0° C. and 1-cyclohexyl-2-(2-pyridyl)ethan-1-one (2.03 g, 10 mmol) in THF (30 mL) was added dropwise to the suspension. After addition was complete, the reaction was stirred for 2.5 hours at room temperature. Then 2-bromomethyl-1,3-dioxolane (1.55 mL, 15 mmol) was added and the reaction was heated at reflux for 16 hours. The reaction mixture was then quenched with water and extracted with diethyl ether (4×50 mL). The combined organic extracts were dried over anhydrous magnesium sulfate, filtered and concentrated under vacuum. The residue was purified by column chromatography (ethyl acetate:hexane, 3:7, silica gel) to provide 1-cyclohexyl-3-(2-(1,2-dioxolane))-2-(2-pyridyl)propan-1-one (1.79 g, 62%) as a yellow oil.

Preparation of 1-Cyclohexyl-2-(2-pyridyl)butan-1-one-4-al

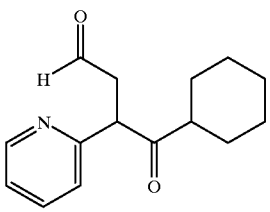

Scheme III, step C: 1-cyclohexyl-3-(2-(1,3-dioxolane))-2-(2-pyridyl)propan-1-one (0.40 g, 1.38 mmol, prepared above) was dissolved in acetone (10 mL), treated with 3N HCl (10 mL) and stirred for 16 hours at room temperature. The reaction mixture was basified with 1N sodium hydroxide (pH=8–9) and extracted with ethyl acetate. The organic extracts were dried over anhydrous sodium sulfate, filtered and concentrated under vacuum to provide crude 1-cyclohexyl-2-(2-pyridyl)butan-1-one-4-al which was carried on to the next step without further purification.

Preparation of the Final Title Compound

Scheme IV, step A: 1-cyclohexyl-2-(2-pyridyl)butan-1-one-4-al (approximately 1.38 g, prepared in Scheme III, step C above) is combined with 7-benzo(b)thiophene-1,2,3,6-tetrahydropyridyl (0.14 g, 9 0.65 mmol, prepared in Scheme I, step D or Scheme II, step D above) in methylene chloride (20 mL) with acetic acid (0.11 mL, 1.95 mmol) and sodium triacetoxyborohydride (0.37 g, 1.76 mmol). The reaction mixture was stirred at room temperature for 18 hours. It was then treated with 1N sodium hydroxide and extracted with methylene chloride. The combined organic extracts were dried over anhydrous sodium sulfate, filtered and concentrated under vacuum. The residue was purified by flash chromatography sodium sulfate, filtered and concentrated under vacuum. The residue was purified by flash chromatography (1:1 hexane:ethyl acetate, silica gel) to provide the free base of the title compound (0.237 g, 82%).

This free base was treated with oxalic acid (41.6 mg) in methanol. The resulting crystals were then collect by filtration to provide the title compound (0.206 g) mp 120–122° C.

Preparation of 4-(7-Benzo(b)thiophene-1,2,3,6-tetrahydropyridyl)-1-cyclohexyl-2-(2-pyridyl)butan-1-one HCl

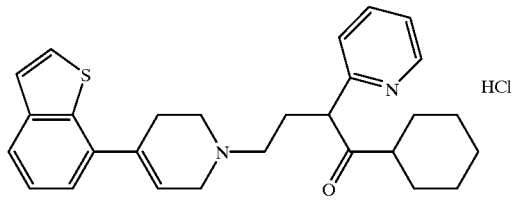

To the free base, 4-(7-benzo(b)thiophene-1,2,3,6-tetrahydropyridyl)-1-cyclohexyl-2-(2-pyridyl)butan-1-one (14.99 g, 33.7 mmole, prepared above) was added acetone (210 mL) and methyl t-butyl ether (150 mL). The solution was heated to reflux and 1.64 N anhydrous HCl in methyl t-butyl ether (20.5 mL) was added slowly while keeping the product in solution. After all of the HCl solution was added, additional methyl t-butyl ether (20 mL) was added and the solution was allowed to cool to room temperature gradually. After the solution was stirred at room temperature for a few hours, the solution was filtered under a positive pressure of nitrogen. The white solid was dried at 50° C. in vacuo to afford 11.68 g (72%) of the title compound. mp=147–154° C., $^1$H NMR (CDCl$_3$) δ 8.54 (dd, J=4.9, 0.9 Hz, 1H), 7.76 (dd, J=7.9, 0.9 Hz, 1H), 7.71 (dt, J=7.7, 1.9 Hz, 1H), 7.44 (d, J=5.5 Hz, 1H), 7.42 (d, J=7.9 Hz, 1H), 7.40–7.34 (m, 2H), 7.22 (d, J=7.6 Hz, 1H), 7.21 (dd, J=7.6, 0.9 Hz, 1H), 6.17 (s, 1H), 4.33 (dd, J=7.6, 6.1, 1H), 4.20–3.62 (br m, 1H), 3.62–3.24 (br m, 2H), 3.24–3.04 (m, 2H), 3.04–2.75 (br m, 1H), 2.75–2.59 (m, 1H), 2.55–2.29 (m, 2H), 1.96–1.50 (m, 5H), 1.50–0.97 (m, 7H).

Preparation of 4-(7-Benzo(b)thiophene-1,2,3,6-tetrahydropyridyl)-1-cyclohexyl-2-(2-pyridyl)butan-1-one 2HCl 4-(7-benzo(b)thiophene-1,2,3,6-tetrahydropyridyl)-1-cyclohexyl-2-(2-pyridyl)butan-1-one (1 equivalent, free base prepared above) was dissolved in methanol. HCl in ether (2 equivalents) was then added. After it was stirred at room temperature for 5 minutes, the volatile was evaporated. The white precipitate was dried under vacuum for 12 hours to provide the title compound, which slowly absorbs water from air. The melting point varies depending upon the amount of water absorbed: 118–130° C.

EXAMPLE 2

Preparation of 4-(7-Benzo(b)thiophene-1,2,3,6-tetrahydropyridyl)-1-cycloheptyl-2-(2-pyridyl)butan-1-one Oxalate

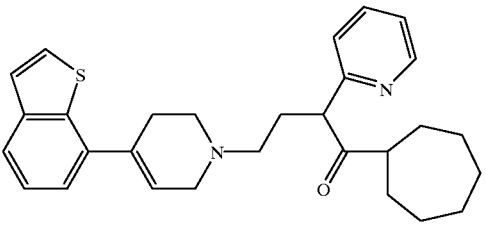

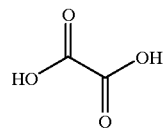

Preparation of N-methoxy-N-methyl Cycloheptyl Amide

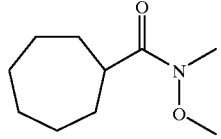

Cycloheptanecarboxylic acid (25.0 g, 0.176 mol) was dissolved in methylene chloride (100 mL) and oxalyl chloride (23 mL, 0.264 mol) was added dropwise to the solution. The reaction mixture was stirred for 30 minutes at room temperature and then concentrated under vacuum to provide the acid chloride of cycloheptanecarboxylic acid as a yellow oil.

N,O-dimethylhydroxylamine hydrochloride (18.03 g, 0.185 mol) was suspended in methylene chloride (200 mL) and treated with triethylamine (49.1 mL, 0.35 mol). The mixture was stirred for 15 minutes at room temperature and then cooled to 0° C. The above-formed acid chloride of cycloheptanecarboxylic acid dissolved in methylene chloride (30 mL) was added dropwise to the cooled solution. After addition was complete, the reaction mixture was warmed to room temperature and allowed to stir for 17 hours. The mixture was then poured into water (200 mL). The layers were separated, and the organic layer was dried over anhydrous sodium sulfate, filtered and concentrated to provide N-methoxy-N-methyl cycloheptyl amide.

Preparation of 1-Cycloheptyl-2-(2-pyridyl)ethan-1-one

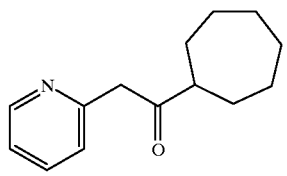

Scheme III, step A: A 100 mL round bottom flask was charged with 2-picoline (2.52 mL, 25.5 mmol) and anhydrous THF (30 mL). The solution was cooled to −78° C. and n-butyllithium (17.5 mL of a 1.6 M solution in THF, 28.05 mmol) was added dropwise to the solution. After addition was complete, the reaction was warmed slowly to room temperature over one hour and then cooled again to −78° C. N-methoxy-N-methyl cycloheptyl amide (5.0 g, 27.03 mmol, formed above) was added to the reaction. The reaction mixture was allowed to warm to room temperature with stirring overnight. The reaction was carefully quenched with water and extracted with ethyl acetate. The organic extracts were dried over anhydrous sodium sulfate, filtered and concentrated under vacuum. The residue was purified by flash chromatography (ethyl acetate:hexane, 3:7, silica gel) to provide 1-cycloheptyl-2-(2-pyridyl)ethan-1-one (5.03 g, 91%)

Preparation of 1-Cycloheptyl-3-(2-(1,3-dioxolane))-2-(2-pyridyl)propan-1-one

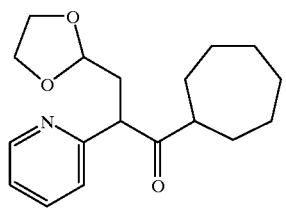

Scheme III, step B: 1-cycloheptyl-2-(2-pyridyl)ethan-1-one (5.0 g, 23.0 mmol, prepared above in Scheme III, step A) was dissolved in anhydrous THF (50 mL) was added dropwise to a suspension of sodium hydride (1.29 g of a 60% dispersion, 32.2 mmol) in anhydrous DMF cooled to 0° C. The reaction mixture was then warmed to room temperature and stirred for one hour. Then 2-bromomethyl-1,3-dioxolane (3.58 mL, 34.5 mmol) and potassium iodide (0.5 g, crushed) were added and the reaction mixture was heated at reflux for 16 hours. Water was added, and the mixture was extracted with ethyl acetate. The organic extracts were combined, dried over anhydrous sodium sulfate, filtered and concentrated under vacuum. The residue was purified by flash chromatography (ethyl acetate/hexane, 3/7, silica gel) to provide 1-cycloheptyl-3-(2-(1,3-dioxolane))-2-(2-pyridyl) propan-1-one (4.52 g, 65%).

Preparation of 1-Cycloheptyl-2-(2-pyridyl)butan-1-one-4-al

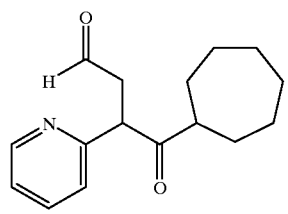

Scheme III, step C; 1-cycloheptyl-3-(2-(1,3-dioxolane))-2-(2-pyridyl)propan-1-one (0.51 g, 1.68 mmol) was dissolved in acetone (10 mL), treated with 3N HCl (10 mL) and stirred for 16 hours at room temperature. The reaction mixture was neutralized with 1N sodium hydroxide (30 mL) and extracted with ethyl acetate. The organic extracts were dried over anhydrous sodium sulfate, filtered and concentrated under vacuum to provide 1-cycloheptyl-2-(2-pyridyl) butan-1-one-4-al.

Preparation of Final Title Compound

Scheme IV, step A: 1-cycloheptyl-2-(2-pyridyl)butan-1-one-4-al (0.31 g, 1.19 mmol, prepared in Scheme III, step C above) is combined with 7-benzo(b)thiophene-3,4-dehydropiperidine (0.26 g, 1.19 mmol, prepared in Example 1, Scheme I, step D) in methylene chloride (10 mL) with acetic acid (0.17 mL, 2.98 mmol) and sodium triacetoxyborohydride (0.33 g, 1.55 mmol). The reaction mixture was stirred at room temperature for 5 hours. It was then made basic with 1N sodium hydroxide and extracted with methylene chloride. The combined organic extracts were dried over anhydrous sodium sulfate, filtered and concentrated under vacuum. The residue was purified by flash chromatography (ethyl acetate:hexane, 1:1, silica gel) to provide the free base of the final title compound (0.19 g).

This free base was treated with oxalic acid (37.6 mg) in methanol. The resulting crystals were filtered to provide the final title compound (0.206 g) mp 105–108° C.

EXAMPLE 3

Preparation of 4-(7-Benzo(b)thiophene-1,2,3,6-tetrahydropyridyl)-1-cyclopentyl-2-(2-pyridyl)butan-1-one Oxalate

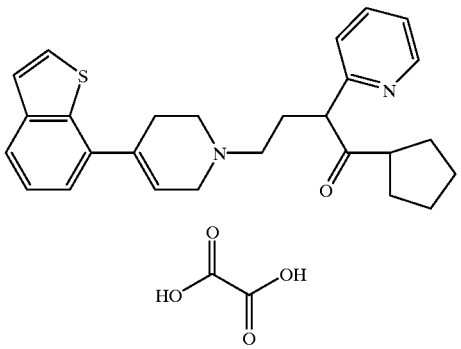

Preparation of 1-Cyclopentyl-2-(2-pyridyl)ethan-1-one

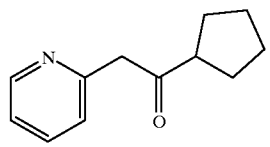

Scheme III, step A: A 100 mL round bottom flask was charged with 2-picoline (2.97 mL, 30.05 mmol) and anhydrous THF (30 mL). The solution was cooled to −78° C. and n-butyllithium (20.7 mL of a 1.6 M solution in THF, 33.1 mmol) was added dropwise. The reaction mixture was slowly warmed to room temperature and then stirred for one hour. The reaction mixture was then cooled back to −78° C. and N-methoxy-N-methyl-cyclopentyl amide (5.0 g, 31.85 mmol) was added. The reaction mixture was allowed to warm to room temperature overnight with stirring and then quenched with 0.1 N HCl to pH 9. The mixture was then extracted with methylene chloride, the organic extracts were combined, dried over anhydrous sodium sulfate, filtered and concentrated under vacuum. The residue was purified by flash chromatography (ethyl acetate:hexane, 3:7, silica gel) to provide 1-cyclopentyl-2-(2-pyridyl)ethan-1-one (4.35 g, 77%).

Preparation of 1-Cyclopentyl-3-(2-(1,3-dioxolane))-2-(2-pyridyl)propan-1-one

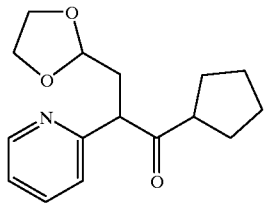

Scheme III, step B: A 500 round bottom flask was charged with 60% sodium hydride (1.27 g, 31.9 mmol) and anhydrous DMF (50 mL). The suspension was cooled to 0° C. and 1-cyclopentyl-2-(2-pyridyl)ethan-1-one (4.30 g, 22.8 mmol, prepared above in Scheme III, step A) dissolved in anhydrous THF (50 mL) was added dropwise to the suspension. The reaction mixture was warmed to room temperature and stirred for one hour. Then 2-bromomethyl-1,3-dioxolane (3.54 mL, 34.2 mmol) and potassium iodide (0.2 g, crushed) were added and the reaction mixture was heated at reflux for 6 hours. The reaction mixture was then cooled to room temperature and stirred for 16 hours. Water was added, and the mixture was extracted with ethyl acetate. The organic extracts were combined, dried over anhydrous sodium sulfate, filtered and concentrated under vacuum. The residue was purified by flash chromatography (ethyl acetate:hexane, 3:7, silica gel) to provide 1-cyclopentyl-3-(2-(1,3-dioxolane))-2-(2-pyridyl)propan-1-one (1.43 g).

Preparation of 1-Cyclopentyl-2-(2-pyridyl)butan-1-one-4-al

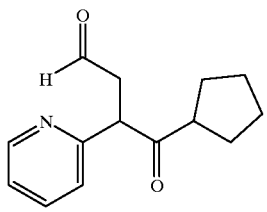

Scheme III, step C: 1-cyclopentyl-3-(2-(1,3-dioxolane))-2-(2-pyridyl)propan-1-one (0.48 g, 1.75 mmol, prepared above in Scheme III, step B) was combined with 3N HCl (10 mL) and acetone (10 mL), and the reaction mixture was stirred overnight at room temperature. The reaction mixture was then neutralized with 1N sodium hydroxide (30 mL) and extracted with diethyl ether. The organic extracts were combined, dried over anhydrous sodium sulfate, filtered and concentrated under vacuum to provide 1-cyclopentyl-2-(2-pyridyl)butan-1-one-4-al (0.165 g).

Preparation of Final Title Compound

Scheme IV, step A: 1-cyclopentyl-2-(2-pyridyl)butan-1-one-4-al (0.38 g, 1.64 mmol, prepared in Scheme III, step C above) was combined with 7-benzo(b)thiophene-3,4-dehydropiperidine (0.35 g, 1.64 mmol, prepared in Example 1, Scheme I, step D) in methylene chloride (20 mL) with acetic acid (0.23 mL, 4.1 mmol) and sodium triacetoxyborohydride (0.45 g, 2.1 mmol). The reaction mixture was stirred at room temperature for 16 hours. It was then made basic with 1N sodium hydroxide and extracted with methylene chloride (20 mL). The organic extract was dried over anhydrous sodium sulfate, filtered and concentrated under vacuum. The residue was purified by flash chromatography (ethyl acetate:hexane, 6:4, silica gel) to provide the free base of the final title compound (0.28 g, 39%).

The above free base was treated with oxalic acid (56.8 mg) in methanol. The resulting crystals were filtered to provide the oxalate salt of the final title compound (0.28 g) mp 118–120° C.

EXAMPLE 4

Preparation of 4-(7-Benzo(b)thiophene-1,2,3,6-tetrahydropyridyl)-1-cyclohexyl-2-(2-pyridyl)butan-1-one Oxalate

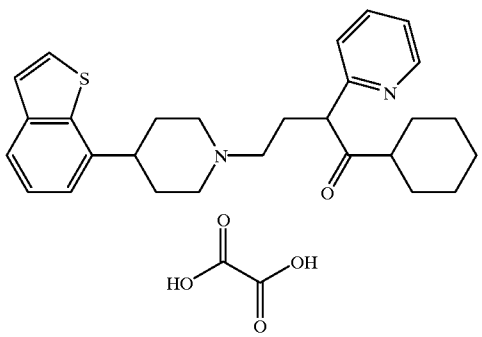

Preparation of 7-Benzo(b)thiophene-piperidine

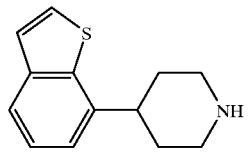

Scheme I, step E: 7-benzo(b)thiophene-3,4-dehydropiperidine (0.75 g, 3.5 mmol, prepared in Example 1, Scheme I, step D) was dissolved in ethanol (25 mL). 10% Palladium on carbon (2.25 g) was added and the reaction was stirred under hydrogen at 60 psi at room temperature overnight. The reaction mixture was filtered and the filtrate concentrated to provide 7-benzo(b)thiophene-piperidine.

Preparation of Final Title Compound

Scheme IV, step A; 1-cyclohexyl-2-(2-pyridyl)butan-1-one-4-al (0.20 g, 0.83 mmol, prepared in Example 1, Scheme III, step C) is combined with 7-benzo(b)thiophene-piperidine (0.13 g, 0.60 mmol, prepared in Scheme I, step E above) in methylene chloride (10 mL) with acetic acid (0.09 mL, 1.5 mmol) and sodium triacetoxyborohydride (0.17 g, 0.78 mmol). The reaction mixture was stirred at room temperature overnight. It was then made basic with 1N sodium hydroxide and extracted with methylene chloride. The organic extract was dried over anhydrous sodium sulfate, filtered and concentrated under vacuum. The residue was purified by flash chromatography (2% methanol/ethyl acetate, silica gel) to provide the free base of the final title compound (0.168 g, 62%).

The free base was then treated with oxalic acid (34 mg) in methanol. The resulting crystals were filtered to provide the final title compound (0.13 g) mp 122–125° C.

EXAMPLE 5

Preparation of 4-(7-Benzo(b)furan-3,4-dehydropiperidinyl)-1-cyclohexyl-2-(2-pyridyl)butan-1-one Dihydrochloride

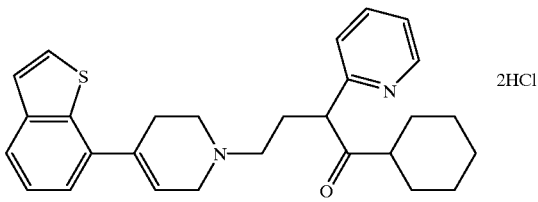

Preparation of 2-(2-Bromophenol)acetaldehyde Diethyl Acetal

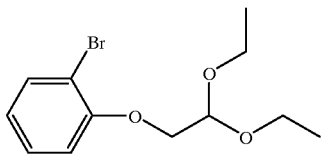

Scheme I, step A: 2-Bromophenol (22.65 g, 0.13 mol) was dissolved in anhydrous DMF (10 mL) and added over 15 minutes to a suspension of sodium hydride (5.76 g of a 60% dispersion, 0.14 mol) in anhydrous DMF (90 mL) at 0° C. The reaction was stirred for an additional 15 minutes and bromoacetaldehyde diethyl acetal (38.4 g, 0.195 mol) was added. The reaction was then heated at reflux for 2 hours. The reaction mixture was then poured into water (100 mL) and extracted with ethyl acetate (3×200 mL). The organic extracts were combined, washed with water (5×100 mL), dried over anhydrous sodium sulfate, filtered and concentrated under vacuum to provide a yellow oil. This oil was then purified by flash chromatography (hexane:ethyl acetate, 9:1, silica gel) to provide 2-(2-bromophenol)acetaldehyde diethyl acetal as a yellow oil.

Preparation of 7-Bromobenzo(b)furan.

Scheme I, step B: Polyphosphoric acid (60 g) and chlorobenzene (100 mL) were combined and heated to reflux. To the refluxing mixture was added dropwise 2-(2-bromophenol)acetaldehyde diethyl acetal (27 g, 0.093 mol, prepared above in Scheme I, step A) dissolved in chlorobenzene (20 mL) over 15 minutes. Heating of the reaction mixture at reflux was continued for 2 hours and then it was cooled to room temperature. 1N sodium hydroxide (100 mL) was added and the reaction was stirred at room temperature overnight. The reaction mixture was then extracted with diethyl ether (3×100 mL), the organic extracts were combined, dried over anhydrous sodium sulfate, filtered and concentrated under vacuum. The residue was purified by flash chromatography (hexane, silica gel) to provide the 7-bromobenzo(b)furan (13.4 g, 73%) as a clear oil.

Preparation of 1-(t-Butoxycarbonyl)-4-(7-benzo(b)furan)-4-hydroxy Piperidine

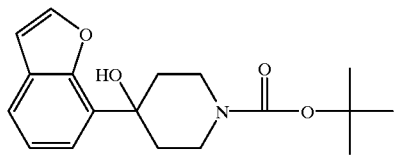

Scheme I, step C: A 500 mL round bottom flask was charged with anhydrous THF (150 mL) and 7-bromobenzo(b)furan (13.0 g, 0.066 mol, prepared above in Scheme I, step B), and the solution was cooled to −78° C. n-Butyllithium (41.2 mL of a 1.6 M solution in THF, 0.066 mol) was added over 3 minutes followed by addition of 1-(t-butoxycarbonyl)-4-piperidone (12.52 g, 0.063 mol). The reaction mixture was then allowed to warm to room temperature over 18 hours with stirring. The reaction was then quenched with water (4 mL) and extracted with ethyl acetate. The organic extracts were combined, dried over anhydrous sodium sulfate, filtered and concentrated under vacuum to provide a tan oil. The tan oil was then purified by flash chromatography (silica gel, 2 times) to provide 1-(t-butoxycarbonyl)-4-(7-benzo(b)furan)-4-hydroxy piperidine (0.2 g).

Preparation of 7-Benzo(b)furan-1,2,3,6-tetrahydropyridyl

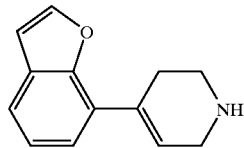

Scheme I, step D: A 500 mL round bottom flask was charged with 1-(t-butoxycarbonyl)-4-(7-benzo(b)furan)-4-hydroxy piperidine (13.1 g, 0.041 mol, prepared above in Scheme I, step C), p-toluenesulfonic acid (19.63 g, 0.10 mol) and toluene (100 mL). The reaction mixture was then heated at reflux for 3 hours during which 2.7 mL of water was collected in a Dean-Stark trap. The reaction mixture was then cooled to room temperature and concentrated under vacuum to a brown oil. Saturated potassium carbonate solution was added to basify and the mixture was extracted with ethyl acetate (2×100 mL). The organic extracts were combined, dried over anhydrous sodium sulfate, filtered and concentrated under vacuum. The residue was purified by flash chromatography (methanol:ammonium hydroxide:methylene chloride, 20:2:78, silica gel) to provide 7-benzo(b)furan-1,2,3,6-tetrahydropyridyl (1.6 g).

Preparation of Final Title Compound

Scheme IV, step A: 1-cyclohexyl-2-(2-pyridyl)butan-1-one-4-al (0.40 g, 1.63 mmol, prepared in Example 1, Scheme III, step C) was combined with 7-benzo(b)furan-1,2,3,6-tetrahydropyridyl (0.33 g, 1.63 mmol, prepared in Scheme I, step D above) in methylene chloride (20 mL) with acetic acid (0.20 mL, 3.42 mmol) and sodium triacetoxyborohydride (0.45 g, 2.12 mmol). The reaction mixture was stirred at room temperature for 2.5 hours. It was then made basic with 1N sodium hydroxide and extracted with methylene chloride (2×50 mL). The organic extracts were combined, dried over anhydrous sodium sulfate, filtered and concentrated under vacuum. The residue was purified by chromatography (ethyl acetate, silica gel) to provide a yellow oil. The oil was taken up in diethyl ether which was then treated with 1 N HCl in diethyl ether. A white precipitate formed which was collected by filtration and dried to provide the title compound (0.23 g) mp 150–154° C.

EXAMPLE 6

Preparation of 4-(7-Benzo(b)furan-1,2,3,6-tetrahydropyridyl)-1-phenyl-2-phenyl-butan-1-one Oxalate

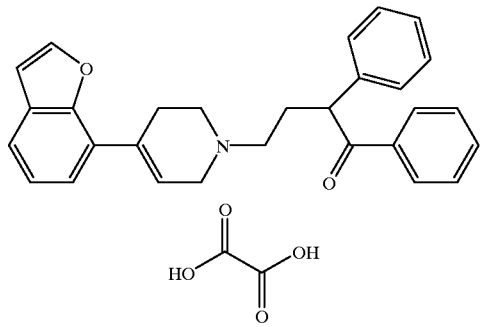

Preparation of 1-Phenyl-3-(2-(1,3-dioxolane))-2-phenyl-propan-1-one

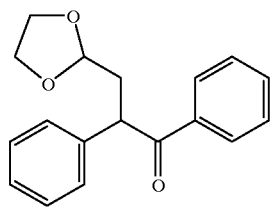

Scheme III, step B: To a stirred lithium diisopropyl amide solution (6.2 mmol in 10 mL of THF) was added deoxybenzoin (1.10 g, 9 5.6 mmol) in DMF (10 mL) at 0° C. under an atmosphere of nitrogen. The mixture was stirred at room temperature for 2 hours and then heated to reflux for 12 hours. The title compound was isolated by standard work-up and purified by purified by flash chromatography to provide 1.17 g (74%).

Preparation of 1-Phenyl-2-phenyl-butan-1-one-4-al

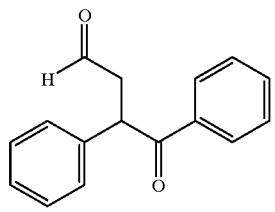

Scheme III, step C: A 500 mL round bottom flask was charged with 1-phenyl-3-(2-(1,3-dioxolane))-2-phenyl-propan-1-one (2.50 g, 8.85 mmol, prepared above in Scheme III, step B above), acetone (100 mL) and 2N HCl (100 mL). The reaction was then stirred at room temperature for 6 hours and then made slightly basic (pH 10) with 1N NaOH. The reaction was then partially concentrated under vacuum and the aqueous/residue was extracted with diethyl ether (2×100 mL). The organic extracts were combined, dried over anhydrous sodium sulfate, filtered and concentrated under vacuum to provide 1-phenyl-2-phenyl-butan-1-one-4-al.

Preparation of Final Title Compound

Scheme IV, step A: 1-phenyl-2-phenyl-butan-1-one-4-al (0.50 g, 2.1 mmol, prepared above in Scheme III, step C), acetic acid (0.25 mL, 4.2 mmol), methylene chloride (20 mL) and 7-benzo(b)furan-3,4-dehydropiperidine (0.42 g, 2.1 mmol, prepared in Example 5, Scheme I, step D) were combined with sodium triacetoxyborohydride (0.58 g, 2.7 mmol) and stirred at room temperature for 16 hours. The reaction was then treated with 1 N sodium hydroxide (5 mL) and extracted with methylene chloride. The organic extracts were combined, dried over anhydrous sodium sulfate, filtered and concentrated under vacuum. The residue was purified by flash chromatography to provide the free base of the title compound (0.533 g).

The free base was treated with oxalic acid (114 mg) in methanol. The solution was concentrated to provide the final title compound (0.48 g) as a yellow powder, mp 85–87° C.

EXAMPLE 7

Preparation of 4-(7-Benzo(b)furan-1,2,3,6-tetrahydropyridyl)-1-cyclopentyl-2-(2-pyridyl)butan-1-one Oxalate

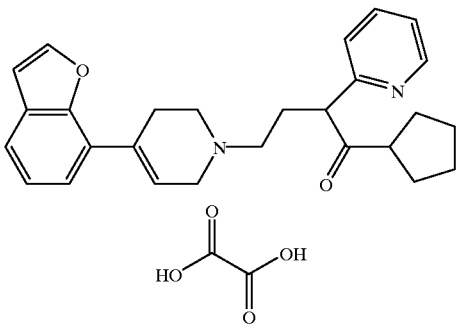

Scheme IV, step A: 1-cyclopentyl-2-(2-pyridyl)butan-1-one-4-al (0.16 g, 0.69 mmol, prepared in Example 3, Scheme III, step C), 7-benzo(b)furan-1,2,3,6-tetrahydropyridyl (0.15 g, 0.76 mmol, prepared in Example 5, Scheme I, step D), methylene chloride (10 mL), and acetic acid (0.08 mL, 1.39 mmol) were combined and treated with sodium triacetoxyborohydride (0.19 g, 0.90 mmol). The reaction mixture was stirred at room temperature for 3 hours and then made basic with 1N sodium hydroxide (5 mL). The reaction mixture was then extracted with methylene chloride, the organic extracts were combined, dried over anhydrous sodium sulfate, filtered and concentrated under vacuum. The residue was purified by flash chromatography (ethyl acetate, silica gel) to provide the free base of the title compound (0.13 g, 45%).

The free base was dissolved in methanol and treated with oxalic acid (28 mg) and concentrated under vacuum to provide the final title compound (0.15 g) mp 160–163° C.

EXAMPLE 8

Preparation of 4-(7-Benzo(b)furan-1,2,3,6-tetrahydropyridyl)-1-cycloheptyl-2-(2-pyridyl)butan-1-one Oxalate

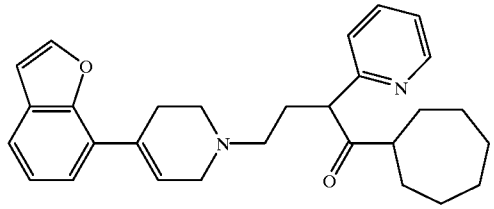

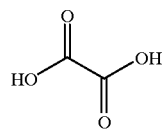

Scheme IV, step A: 1-Cycloheptyl-2-(2-pyridyl)butan-1-one-4-al (0.50 g, 1.93 mmol, prepared in Example 2, Scheme III, step C)), 7-benzo(b)furan-1,2,3,6-tetrahydropyridyl (0.42 g, 2.12 mmol, prepared in Example 5, Scheme I, step D), methylene chloride (20 mL), and acetic acid (0.28 mL, 4.83 mmol) were combined and treated with sodium triacetoxyborohydride (0.53 g, 2.51 mmol). The reaction mixture was stirred at room temperature for 3.5 hours and then made basic with 1N sodium hydroxide (5 mL). The reaction mixture was then extracted with methylene chloride, the organic extracts were combined, dried over anhydrous sodium sulfate, filtered and concentrated under vacuum. The residue was purified by flash chromatography (ethyl acetate, silica gel) to provide the free base of the final title compound (0.53 g, 62%).

The free base was dissolved in methanol and treated with oxalic acid (0.104 g) and concentrated under vacuum to provide the final title compound (0.420 g) mp 118–119° C.

EXAMPLE 9

Preparation of 4-(5-Fluoro-7-benzo(b)furan-1,2,3,6-tetrahydropyridyl)-1-cyclohexyl-2-(2-pyridyl)butan-1-one Oxalate

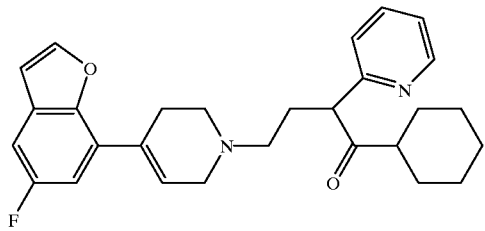

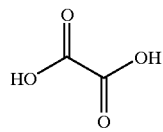

Preparation of 2-(2-Bromo-4-fluorophenol) acetaldehyde Diethyl Acetal

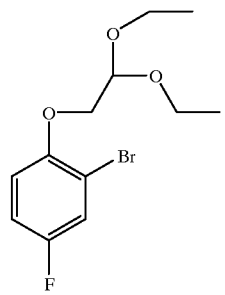

Scheme I, step A: A 500 mL round bottom flask was charged with sodium hydride (8.69 g of a 60% dispersion, 0.217 mol) and anhydrous DMF (130 mL), and the suspension was cooled to 0° C. To the cooled stirring suspension was added 2-bromo-4-fluorophenol (39.5 g, 0.207 mmol) dissolved in anhydrous DMF (20 mL). The reaction was stirred for 30 minutes after addition and then bromoacetaldehyde diethyl acetal (42.8 g, 0.217 mol) was added. The reaction was then heated at reflux for 2.5 hours, cooled to room temperature, and stirred for 24 hours. The reaction mixture was then poured into water and extracted with ethyl acetate (2×200 mL). The organic extracts were combined, washed with water (5×100 mL), dried over anhydrous sodium sulfate, filtered and concentrated under vacuum. The residue was purified by flash chromatography to provide 2-(2-bromo-4-fluorophenol)acetaldehyde diethyl acetal (53.3 g).

Preparation of 5-Fluoro-7-bromo-benzo(b)furan

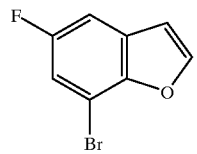

Scheme I, step B: A 500 mL round bottom flask was charged with chlorobenzene (120 mL) and polyphosphoric acid (40.0 g), and the mixture was heated to reflux. To the refluxing mixture was added dropwise 2-(2-bromo-fluorophenol)acetaldehyde diethyl acetal (48.3 g, 0.16 mol, prepared in Scheme I, step A above) dissolved in chorobenzene (60 mL). After refluxing for 2 hours at room temperature, the reaction mixture was cooled to room temperature and poured into 1 N sodium hydroxide. The reaction mixture was then stirred for 16 hours, extracted with diethyl ether, the organic extracts were combined, dried over anhydrous sodium sulfate, filtered and concentrated under vacuum. The residue was purified by flash chromatography (hexane, silica gel) to provide 5-fluoro-7-bromo-benzo(b)furan (9.3 g) as a clear oil.

Preparation of 1-(t-Butoxycarbonyl)-4-(5-fluoro-7-benzo(b)furan-4-hydroxy Piperidine

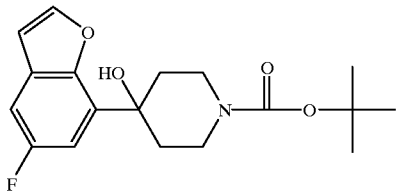

Scheme I, step C: A 200 mL round bottom flask was charged with anhydrous THF (100 mL), 5-fluoro-7-bromo-benzo(b)furan (2.2 g, 0.01 mol) and 1-(t-butoxycarbonyl)-4-piperidone (2.2 g, 0.011 mol). The solution was cooled to −78° C. and treated with sec-butyllithium (8.3 mL of a 1.3 M solution in cyclohexane, 0.011 mol). The reaction mixture was then slowly warmed to room temperature and stirred for 16 hours. The reaction mixture was then quenched with water and extracted with ethyl acetate (2×100 mL). The organic extracts were combined, dried over anhydrous sodium sulfate, filtered and concentrated under vacuum to provide a yellow solid. This yellow solid was recrystallized from diethyl ether to provide 1-(t-butoxycarbonyl)-4-(5-fluoro-7-benzo(b)furan)-4-hydroxy piperidine (0.45 g, 13.4% as a tan solid, mp 228–230° C.

Preparation of 5-Fluoro-7-benzo(b)furan-1,2,3,6-tetrahydropyridyl

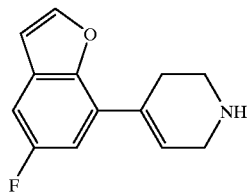

Scheme I, step D: 1-(t-butoxycarbonyl)-4-(5-fluoro-7-benzo(b)furan)-4-hydroxy piperidine (4.16 g, 12.42 mmol, prepared in Scheme I, step C above) was dissolved in toluene (120 mL) and treated with p-toluenesulfonic acid (5.91 g, 31.04 mmol). The reaction mixture was heated to reflux for 3 hours, then cooled to room temperature and then made basic with 1 N sodium hydroxide. The layers were separated, the organic phase was dried over anhydrous sodium sulfate, filtered and concentrated under vacuum. The residue was taken up in ethyl acetate, washed with 1N sodium hydroxide (3×50 mL), dried over anhydrous sodium sulfate, filtered and concentrated under vacuum to provide 5-fluoro-7-benzo(b)furan-1,2,3,6-tetrahydropyridyl.

Alternative Route:

Preparation of 1-(t-Butoxycarbonyl)-4-(5-fluoro-7-benzo(b)furan)-1,2,3,6-tetrahydropyridyl

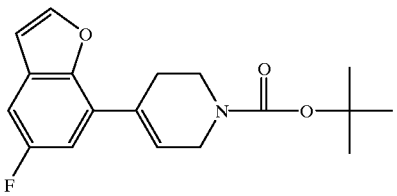

Scheme II, step C: 5-fluoro-7-bromo-benzo(b)furan (5.40 g, 25.13 mmol, prepared in Scheme I, step B above) was combined with 1-(t-butoxycarbonyl)-4-tributylstannyl-1,2,3,6-tetrahydropyridyl (11.87 g, 25.13 mmol, prepared in Example 1, Scheme II, step B ), toluene (150 mL) and tetrakis(triphenylphosphine)palladium(0) (0.99 g, 0.85 mmol). The reaction mixture was heated to reflux for 20 hours, then cooled to room temperature and quenched with water. The reaction was then extracted with ethyl acetate, the organic extracts were combined, dried over anhydrous sodium sulfate, filtered and concentrated under vacuum. The residue was purified by flash chromatography (hexane:ethyl acetate, 9:1, silica gel) to provide 1-(t-butoxycarbonyl)-4-(5-fluoro-7-benzo(b)furan)-1,2,3,6-tetrahydropyridyl (6.47 g, 81%).

Preparation of 5-Fluoro-7-benzo(b)furan-1,2,3,6-tetrahydropyridyl

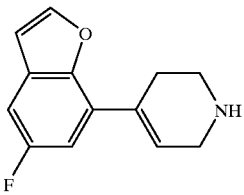

Scheme II, step D: 1-(t-butoxycarbonyl)-4-(5-fluoro-7-benzo(b)furan)-1,2,3,6-tetrahydropyridyl (6.47 g, 20.4 mmol, prepared above in Scheme II, step C) was combined with p-toluenesulfonic acid (11.65 g, 61.2 mmol) and toluene (200 mL). The reaction mixture was heated at reflux for 1.5 hours. It was then diluted with ethyl acetate (300 mL) and washed with 1N sodium hydroxide (3×200 mL). The organic phase was dried over anhydrous sodium sulfate, filtered and concentrated under vacuum. The residue was taken up in 0.2N HCl, the aqueous was washed with diethyl ether (3×200 mL) and then the aqueous was made basic with 5N sodium hydroxide. The aqueous was then extracted with diethyl ether, the organic extracts were combined, dried over anhydrous sodium sulfate, filtered and concentrated under vacuum to provide 5-fluoro-7-benzo(b)furan-1,2,3,6-tetrahydropyridyl (3.15 g, 71%).

Preparation of 1-Cyclohexyl-2-(2-pyridyl)butan-1-one-4-al

Scheme III, step C: 1-cyclohexyl-3-(2-(1,3-dioxolane))-2-(2-pyridyl)propan-1-one (0.50 g, 1.73 mmol, prepared in Example 1, Scheme III, step B) was combined with acetone (10 mL) and 3N HCl (10 mL). The reaction mixture was stirred for 18 hours at room temperature and then neutralized with 1N sodium hydroxide (30 mL). The neutralized mixture was then extracted with diethyl ether, the organic extracts were combined, dried over anhydrous sodium sulfate, filtered and concentrated under vacuum to provide 1-cyclohexyl-2-(2-pyridyl)butan-1-one-4-al (0.22 g).

Preparation of Final Title Compound

Scheme IV, step A: 1-cyclohexyl-2-(2-pyridyl)butan-1-one-4-al (0.22 g, prepared in Scheme III, step C above), 5-fluoro-7-benzo(b)furan-1,2,3,6-tetrahydropyridyl (0.20 g, 0.90 mmol, prepared in Scheme I, step D or Scheme II, step D above), methylene chloride (10 mL), and acetic acid (0.15 mL, 2.7 mmol) were combined and treated with sodium triacetoxyborohydride (0.25 g, 1.17 mmol). The reaction mixture was stirred at room temperature for 3 hours and then made basic with 1N sodium hydroxide (5 mL). The reaction mixture was then extracted with methylene chloride, the organic extracts were combined, dried over anhydrous sodium sulfate, filtered and concentrated under vacuum. The residue was purified by flash chromatography to provide the free base of the final title compound (0.19 g, 47%).

The free base was dissolved in methanol and treated with oxalic acid (38.3 mg) and concentrated under vacuum to provide the final title compound (0.188 g) mp 117–120° C.

EXAMPLE 10

Preparation of 4-(2-Methyl-5-fluoro-7-benzo(b) furan-1,2,3,6-tetrahydropyridyl)-1-cyclohexyl-2-(2-pyridyl)butan-1-one Oxalate

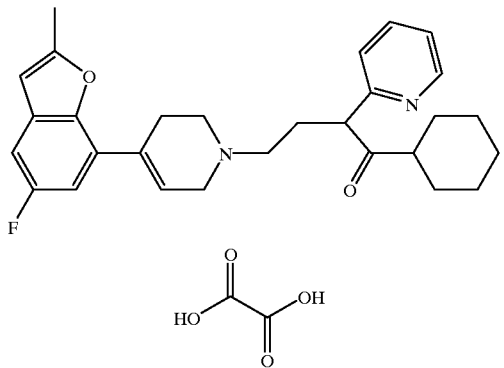

Preparation of Ethyl 2-(2'-Bromo-4'-fluorophenoxy) propionate

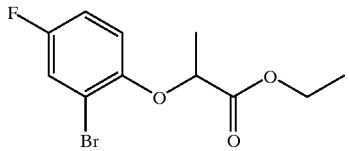

Scheme IA, step A: 2-bromo-4-fluorophenol (15.0 g, 78.5 mmol) was dissolved in THF (200 mL) and treated with potassium carbonate (13.0 g, 94.2 mmol) and ethyl 2-bromopropionate (11.2 mL, 86.4 mmol). The reaction mixture was heated at reflux for 3 hours. Potassium iodide (0.1 g) was added and the reaction mixture was stirred for an additional 2 hours at reflux. The reaction was then cooled, diluted with water and extracted with ethyl acetate. The organic extracts were combined, dried over anhydrous sodium sulfate, filtered and concentrated under vacuum. The residue was purified by flash chromatography to provide ethyl 2-(2'-bromo-4'-fluorophenoxy)propionate (19.8 g) as a clear oil.

Preparation of 2-(2'-Bromo-4'-fluoro) phenoxypropionaldehyde.

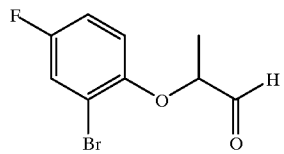

Scheme IA, step B: ethyl 2-(2'-bromo-4'-fluorophenoxy) propionate (19.4 g, 66.7 mmol, prepared in Scheme IA, step A above) was dissolved in anhydrous toluene (400 mL) and cooled to −78° C. The cooled solution was then treated dropwise over 35 minutes with diisobutylaluminum hydride (100 mL of a 1M solution in toluene, 100 mmol). It was then stirred for an additional 20 minutes and then quenched at −78° C. with methanol. After warming to room temperature it was diluted with saturated sodium tartrate solution for 30 minutes and then extracted with ethyl acetate. The organic extracts were combined, dried over anhydrous sodium sulfate, filtered and concentrated under vacuum to provide 2-(2'-bromo-4'-fluoro)phenoxypropionaldehyde (16.9 g).

Preparation of 2-Methyl-5-fluoro-7-bromo-benzo(b) furan

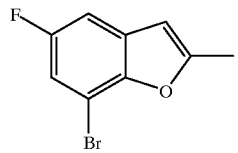

Scheme IA, step C: 2-(2'-Bromo4'-fluoro) phenoxypropionaldehyde (16.5 g, 66.8 mmol, prepared above in Scheme IA, step B) was dissolved in chlorobenzene (100 mL) and added dropwise to a refluxing mixture of polyphosphoric acid (60 g) in chlorobenzene (300 mL). After addition was complete, the reaction mixture was heated at reflux for 3 hours and then cooled to room temperature overnight. The reaction mixture was then slowly poured into dilute sodium hydroxide and stirred for 30 minutes. The mixture was extracted with ethyl acetate (3×300 mL), the organic extracts were combined, dried over anhydrous sodium sulfate, filtered and concentrated under vacuum. The black residue was purified by flash chromatography (hexane, silica gel) to provide 2-methyl-5-fluro-7-bromo-benzo(b)furan (5.2 g).

Preparation of 1-(t-Butoxycarbonyl)-4-(2-methyl-5-fluoro-7-benzo(b)furan)-4-hydroxy Piperidine

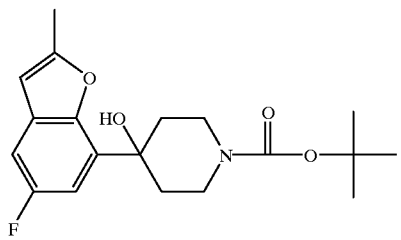

Scheme I, step C: 2-methyl-5-fluro-7-bromo-benzo(b) furan (3.70 g, 16.16 mmol, prepared above in Scheme IA, step C) was dissolved in anhydrous THF (100 mL), the solution was cooled to −78° C. and then treated with n-butyllithium (11.12 mL of a 1.6 M solution in THF, 17.74 mmol). After addition was complete, the reaction was stirred for an additional 10 minutes at −78° C. and 1-(t-butoxycarbonyl)-4-piperidone (3.54 g, 17.78 mmol) was added. The reaction mixture was allowed to warm to room temperature overnight and then it was quenched with water. The quenched reaction was then extracted with ethyl acetate, the combined organic extracts were dried over anhydrous sodium sulfate, filtered and concentrated under vacuum. The residue was purified by flash chromatography to provide 1-(t-butoxycarbonyl)-4-(2-methyl-5-fluoro-7-benzo(b)furan)-4-hydroxy piperidine (3.68 g, 65%).

Preparation of 2-Methyl-5-fluoro-7-benzo(b)furan-1,2,3,6-tetrahydropyridyl Oxalate

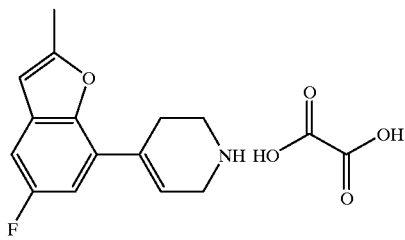

Scheme I, step D: 1-(t-butoxycarbonyl)-4-(2-methyl-5-fluoro-7-benzo(b)furan-4-hydroxy piperidine (3.68 g, 10.54 mmol, prepared above in Scheme I, step C) was dissolved in toluene (50 mL) and treated with p-toluenesulfonic acid (8.02 g, 42.18 mmol). The reaction was heated at reflux for 1.5 hours, then cooled to room temperature and concentrated under vacuum to a yellow semi-solid. The semi-solid was suspended in ethyl acetate and washed with 1N sodium hydroxide (5×50 mL). The organic phase was then dried over anhydrous sodium sulfate, filtered and concentrated under vacuum to provide the free base of the title compound as a yellow oil. The oil was dissolved in methanol, treated with oxalic acid (0.77 g) and then concentrated under vacuum to provide 2-methyl-5-fluoro-7-benzo(b)furan-1,2,3,6-tetrahydropyridyl oxalate as a tan solid.

Preparation of Final Title Compound

Scheme IV, step A; 1-cyclohexyl-2-(2-pyridyl)butan-1-one-4-al (0.32 g, 1.31 mmol, prepared in Example 1, Scheme III, step C), 2-methyl-5-fluoro-7-benzo(b)furan-3,4-dehydropiperidine oxalate (0.21 g, 0.92 mmol, prepared in Scheme I, step D, above), methylene chloride (10 mL), and acetic acid (0.22 mL, 3.93 mmol) were combined and treated with sodium triacetoxyborohydride (0.36 g, 1.70 mmol). The reaction mixture was stirred at room temperature for 5 hours and then made basic with 1N sodium hydroxide (5 mL). The reaction mixture was then extracted with methylene chloride, the organic extracts were combined, dried over anhydrous sodium sulfate, filtered and concentrated under vacuum. The residue was purified by flash chromatography to provide the free base of the title compound (0.162 g, 38%).

The free base was dissolved in methanol and treated with oxalic acid (31.6 mg) and concentrated under vacuum to provide the final title compound, mp 188–189° C.

EXAMPLE 11

Preparation of 4-(7-Benzo(b)furan-1,2,3,6-tetrahydropyridyl)-1-phenyl-2-phenyl-butan-1-ol Oxalate

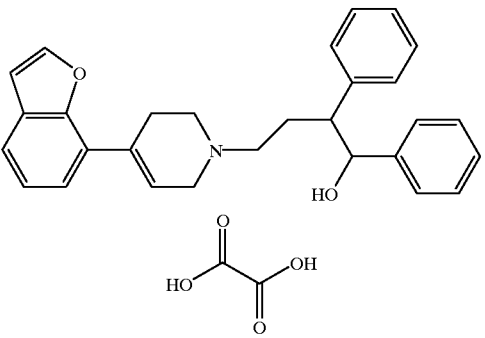

Scheme IV, step C: A 50 mL round bottom flask was charged with 4-(7-benzo(b)furan-3,4-dehydropiperidinyl)-1-phenyl-2-phenyl-butan-1-one (0.30 g, 0.59 mmol, prepared in Example 6) and methylene chloride (10 mL). The solution was cooled to −78° C. and treated dropwise with diisobutylaluminum hydride (1.76 mL of a 1 M solution in toluene, 1.76 mmol). The reaction mixture was then warmed slowly to room temperature over 2 hours and then stirred for 16 hours. The reaction mixture was then diluted with saturated potassium sodium tartrate solution and then extracted with methylene chloride. The organic extracts were combined, dried over anhydrous sodium sulfate, filtered and concentrated under vacuum. The residue was purified by flash chromatography to provide the free base of the title compound (0.154 g). The free base was dissolved in methanol, treated with oxalic acid (11 mg) and concentrated under vacuum to provide the title compound, mp 105–107° C.

EXAMPLE 12

Preparation of 4-(4-Fluoro-7-benzo(b)furan-1,2,3,6-tetrahydropyridyl)-1-cyclohexyl-2-(2-pyridyl)butane Oxalate

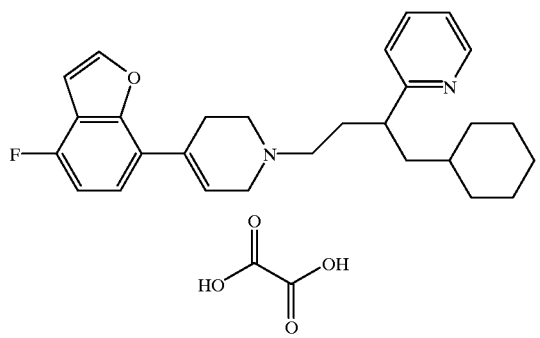

Preparation of 2-Pyridyl-1-cyclohexylethane

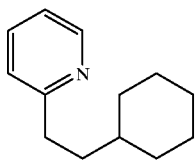

Scheme V, step A: 2-Picoline (5 g, 54 mmol) is dissolved in THF (100 mL) and cooled to −78° C. N-Butyllithium (40 mL of a 1.6M solution in THF, 64.3 mmol) was added to the solution over 10 minutes. The reaction mixture was then warmed to room temperature for 5 minutes and then cooled back down to −78° C. Then cyclohexylmethyl bromide (10 g, 57 mmol) was added, the reaction was warmed to room temperature and allowed to stir overnight. The reaction was then heated at reflux for 6 hours and then cooled to room temperature. The solvent was removed under vacuum and water and ethyl acetate were then added to the residue. The layers were separated and the aqueous was extracted with ethyl acetate. The organic extracts were combined, dried over anhydrous magnesium sulfate, filtered and concentrated to provide a dark oil. The oil was purified by flash chromatography to provide 2-pyridyl-1-cyclohexylethane (9 g, 89%).

Preparation of 2-Pyridyl-3-cyclohexyl-butyraldehyde Diethyl Acetal

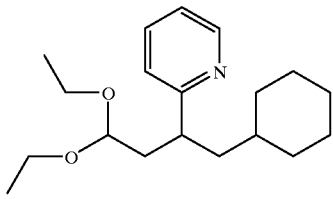

Scheme V, step B: 2-Pyridyl-1-cyclohexylethane (2 g, 10.6 mmol, prepared above) was dissolved in THF (20 mL) and cooled to −78° C. N-Butyllithium (13 mL of a 1.6 M solution in THF, 21.2 mmol) was added to the cooled solution. After stirring for 10 minutes, the cooling bath was removed and after 10 minutes, when the reaction had reached room temperature, it was re-cooled to −78° C. Bromoacetaldehyde diethyl acetal (2.1 g, 10.6 mmol) was then added and after one hour the cooling bath was removed. After 1.5 hours, n-Bu$_4$NBr was added and the reaction was then stirred overnight. Water was then added and the quenched reaction was extracted with ethyl acetate (3 times). The organic extracts were combined, dried over anhydrous sodium sulfate, filtered and concentrated under vacuum. The residue was purified by flash chromatography to provide 2-pyridyl-3-cyclohexyl-butyraldehyde diethyl acetal (1.5 g, 46%).

Preparation of 4-Cyclohexyl-3-(2-pyridyl)-butyraldehyde

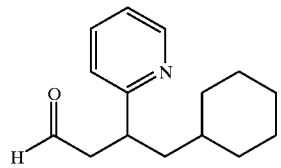

Scheme V, step C: 2-Pyridyl-3-cyclohexyl-butyraldehyde diethyl acetal (650 mg) was dissolved in acetone (10 mL), treated with HCl (a solution of 2.5 mL concentrated HCl and 7.5 mL water) and the reaction was stirred at room temperature overnight. 1N sodium hydroxide (30 mL) was then added and the neutralized reaction mixture was extracted with ethyl acetate (2 times). The organic extracts were combined, dried over anhydrous magnesium sulfate, filtered and concentrated under vacuum to provide 4-cyclohexyl-3-(2-pyridyl)-butyraldehyde (480 mg) as an oil.

Preparation of 2-(2-Bromo-5-fluorophenol) acetaldehyde Diethyl Acetal

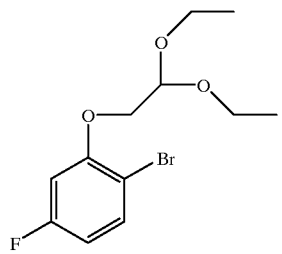

Scheme I, step A: 2-Bromo-5-fluorophenol (15 g, 78.5 mmol), bromoacetaldehyde diethyl acetal (16.2 g, 82.5 mmol) and sodium hydride (3.8 g of a 60% dispersion, 94.2 mmol) were combined with DMF (100 mL) in a manner analogous to the procedure described in Example 1, Scheme I, step A, to provide 2-(2-bromo-5-fluorophenol) acetaldehyde diethyl acetal (21.8 a, 90%).

Preparation of 4-Fluoro-7-bromo-benzo(b)furan

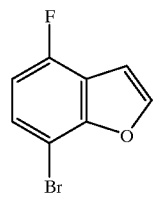

Scheme I, step B: 2-(2-Bromo-5-fluorophenol) acetaldehyde diethyl acetal (21 g, prepared above) were combined with polyphosphoric acid (50 g) and chlorobenzene (250 mL) in a manner analogous to the procedure described in Example 9, Scheme I, step B to provide 4-fluoro-7-bromo-benzo(b)furan (8 g).

Preparation of 1-(t-Butoxycarbonyl)-4-(4-fluoro-7-benzo(b)furan)-4-hydroxy Piperidine

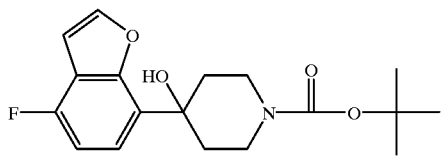

Scheme I, step C: 4-Fluoro-7-bromo-benzo(b)furan (5.58 g, 26 mmol) was combined with magnesium (1.26 g, 52 mmol) in diethyl ether (100 mL) and the mixture was stirred for 30 minutes. Then 1,2-dibromoethane (0.5 mL) was added. After 15 minutes an additional amount of 1,2-dibromoethane (1.7 mL) was added over 2 hours. It was then heated to gentle reflux for one hour and then cooled to room temperature. 1-(t-Butoxycarbonyl)-4-piperidone (5.7 g, 23.6 mmol) dissolved in diethyl ether was then added to the reaction mixture and the reaction was stirred overnight. Then ethyl acetate (100 mL) and water (200 mL) was added followed by addition of 1N HCl until the layers separated. The layers were separated and the aqueous was extracted with ethyl acetate (2 times). The organic extracts were combined, dried over anhydrous magnesium sulfate, filtered and concentrated under vacuum to provide 1-(t-butoxycarbonyl)-4-(4-fluoro-7-benzo(b)furan)-4-hydroxy piperidine (9.2 g).

Preparation of 4-Fluoro-7-benzo(b)furan-1,2,3,6-tetrahydropyridyl

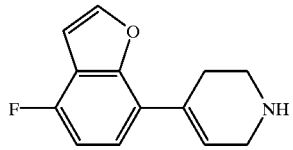

Scheme I, step D: 1-(t-Butoxycarbonyl)-4-(4-fluoro-7-benzo(b)furan)-4-hydroxy piperidine (9.2 g, 28.8 mmol), p-toluenesulfonic acid (12.0 g, 63 mmol) and toluene (200 mL) was combined in a manner analogous to the procedure described in Example 9, Scheme I, step D to provide 4-fluoro-7-benzo(b)furan-1,2,3,6-tetrahydropyridyl (4.1 g, 83%) as an oil.

Preparation of Final Title Compound

Scheme V, step D: 4-Fluoro-7-benzo(b)furan-3,4-dehydropiperidine (220 mg), 4-cyclohexyl-3-(2-pyridyl)-butyraldehyde (201 mg, 0.82 mmol), acetic acid (0.14 mL, 2.46 mmol), sodium triacetoxyborohydride (226 mg, 1.067 mmol) and methylene chloride (10 mL) were combined in a manner analogous to the procedure described in Example 9, Scheme I, step D to provide, after purification by flash chromatography (ethyl acetate:hexane, 7:3 to 1:1, silica gel), the free base of the final title compound (167 mg). The free base was treated with (34.8 mg) oxalic acid in methanol. The solution was concentrated under vacuum to provide the title compound, mp 110–115° C.

EXAMPLE 13

Preparation of 4-(5-Fluoro-7-benzo(b)furan-piperidinyl)-1-cyclohexyl-2-(2-pyridyl)butan-1-one Oxalate

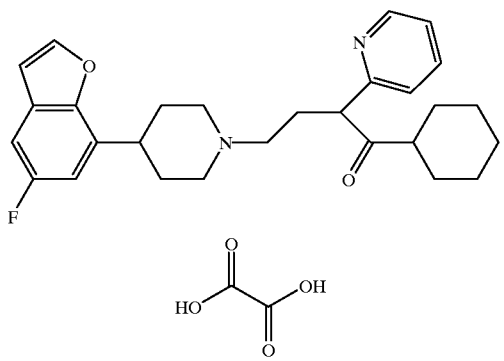

Preparation of 4-Fluoro-7-benzo(b)furan-piperidine

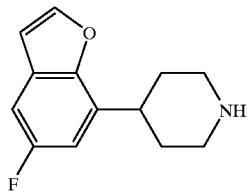

Scheme I, step E: 5-fluoro-7-benzo(b)furan-3,4-dehydropiperidine (0.70 g, 3.23 mmol, prepared in Example 9, Scheme I, step D) was dissolved in absolute ethanol (30 mL) and treated with 10% palladium on carbon (0.21 g) and $NH_4CO_2$ (0.71 g, 11.31 mmol). The reaction mixture was heated to reflux for 3 hours, cooled and then stirred at room temperature for 16 hours. The reaction mixture was then filtered through Celite (diatomaceous earth) and the filtrate was concentrated under vacuum to provide a clear oil (0.609 g). The oil was taken up in methanol, treated with oxalic acid (0.25 g) and then concentrated under vacuum to provide a white solid. The white solid was then triturated with diethyl ether to provide 4-fluoro-7-benzo(b)furan-piperidine (0.6 g), mp 210–211° C.

Preparation of Final Title Compound

Scheme IV, step A: 1-cyclohexyl-2-(2-pyridyl)butan-1-one-4-al (0.42 g (50% pure), 0.86 mmol, prepared in Example 1, Scheme II, step C), 4-fluoro-7-benzo(b)furan-piperidine (0.19 g, 0.87 mmol, prepared in Scheme I, step E, above), methylene chloride (15 mL), and acetic acid (0.15 mL, 2.6 mmol) were combined and treated with sodium triacetoxyborohydride (0.24 g, 1.12 mmol). The reaction mixture was stirred at room temperature for 18 hours and then made basic with 1N sodium hydroxide (5 mL). The reaction mixture was then extracted with methylene chloride, the organic extracts were combined, dried over anhydrous sodium sulfate, filtered and concentrated under vacuum. The residue was purified by flash chromatography to provide the free base of the title compound (0.334 g, 85%).

The free base was dissolved in methanol and treated with oxalic acid (66 mg) and concentrated under vacuum to provide the final title compound, mp 154–155° C.

The following Table I illustrates additional compounds of the present invention. The following compounds are readily prepared by one of ordinary skill in the art in a manner analogous to the procedures described hereinabove.

TABLE I

| Example | Compound | Melting Point |
|---|---|---|
| 14 | | 130–132° C. |
| 15 | | 123–125° C. |
| 16 | | 148–150° C. |
| 17 | | 118–120° C. |
| 18 | | 170–175° C. |
| 19 | | 185–188° C. |

TABLE I-continued

| Example | Compound | Melting Point |
|---|---|---|
| 20 | | 138–140° C. |
| 21 | | 118–120° C. |
| 22 | | 135–138° C. |
| 23 | | 190–191° C. |
| 24 | | 82–85° C. |
| 25 | | 82–85° C. |

TABLE I-continued

| Example | Compound | Melting Point |
|---|---|---|
| 26 | | 137–139° C. |
| 27 | | 85–92° C. |

More specifically, the compound of Example 17 is prepared as follows:

Preparation of 4-(4-Fluoro-7-benzo(b)furan-1,2,3,6-tetrahydropyridyl)-1-cyclohexyl-2-2-(2-pyridyl)butan-1-one Oxalate

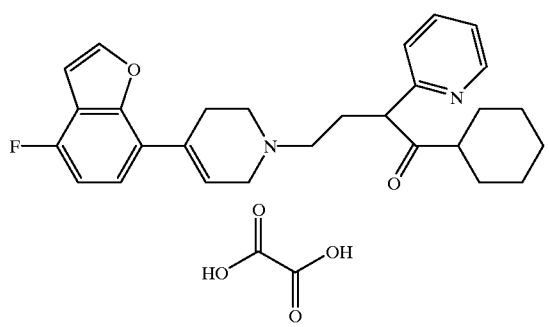

4-(4-fluoro-7-benzo(b)furan-3,4-dehydropiperidine (5 g, 23 mmol, prepared in example 12), 1-cyclohexyl-2-(2-pyridyl)butan-1-one-4-al (8.5 g, 35 mmol, prepared in example 1, Scheme III, step C), methylene chloride (200 mL) and acetic acid (5.2 mL, 92 mmol) were combined and treated with sodium triacetoxyborohydride (8.8 g, 41 mmol). The reaction mixture was stirred at room temperature for 2.5 hours and then made basic with 1 N sodium hydroxide. The reaction mixture was then extracted with methylene chloride. The organic extracts were combined, dried over anhydrous sodium sulfate, filtered, and concentrated under vacuum. The residue was purified by flash chromatography (solvent: Ethyl acetate) to provide the free base of the title compound (9.7 g, 94%) as an oil. The free base was dissolved in methanol and treated with 1 equivalent of oxalic acid and concentrated under vacuum, to provide the final title compound, melting point 118–200° C.

Preparation of 4-(4-Fluoro-7-benzo(b)furan-1,2,3,6-tetrahydropyridyl)-1-cyclohexyl-2-2-(2-pyridyl)butan-1-one 2HCl 4-(4-fluoro-7-benzo(b)furan-1,2,3,6-tetrahydropyridyl)-1-cyclohexyl-2-2-(2-pyridyl)butan-1-one (493 mg, free base prepared above) was dissolved in diethyl ether (40 ml) and an ether solution of saturated with HCl gas was added dropwise until slightly acid as indicated by pH paper. This gave a filterable solid of the title compound (494 mg, 86% yield) melting point 105–110° C. Mass Spec ESI+, M+1= 447.2 (MW of free base=446.56), $^1$H NMR (300 MHz, CDCl$_3$) δ 068–1.878 ppm (15H, m); 2.35–4.36 ppm (9H, m); 6.44–8.55 ppm (9H, m).

EXAMPLE 28

Preparation of 1-Cyclohexyl-2-phenylpropanol

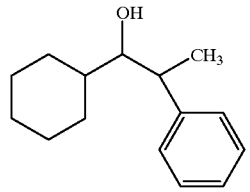

Scheme VI, step A: To a solution of cyclohexylmagnesium chloride (50 mmol) in 25 mL of Et$_2$O and 40 mL of THF at −5° C. was added a solution of 2-phenylpropanaldehyde (5.36 g, 40 mmol) in 10 mL of THF. The reaction mixture exothermed to 5° C. After stirring at room temperature for 75 min, the solution was poured onto ice cold 1 N HCl, extracted with toluene, dried over MgSO$_4$, and concentrated to give the title compound as a colorless oil (6.15 g, 70%): $^1$H NMR (d$^6$-DMSO): δ 7.23–7.30 (m, 2H, phenyl CH), 7.15–7.22 (m, 3H, phenyl CH), 4.17–4.51 (brs, 1H, —OH), 3.23–3.33 (m, 1H, R$_2$C HOH), 2.78 (dq, J=7.0 Hz, J=7.1 Hz, 1H, —CH(CH$_3$)Ph), 1.23–1.83 (m, 6H, cyclohexyl CH), 1.20 (d, J=6.9 Hz, 3H, —CH(CH$_3$)Ph), 0.88–1.18 (m, 5H, cyclohexyl CH).

Preparation of Cyclohexyl 1-Phenylethyl Ketone

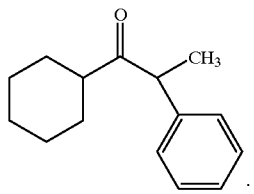

Scheme VI, step B: DMSO (118 mL, 1.6674 mol) was added dropwise to a solution of 126.42 g (0.579 mol) of 1-cyclohexyl-2-phenylpropanol in 1737 mL of $CH_2Cl_2$ (cooled in a wet ice acetone bath). After 29 min, 147.93 g (1.0422 mol) of $P_2O_5$ was added. After 11 min, the cooling bath was removed. An aliquot quenched with $Et_3N$ showed complete reaction within 3 h at RT. The reaction mixture was cooled in a wet ice acetone bath. $Et_3N$ (282 mL, 2.0265 mol) was added dropwise to the cooled reaction mixture over a 30 min period. The cooling bath was removed and the mixture was stirred overnight at RT. The reaction mixture was quenched by dropwise addition of 500 mL of 3 N HCl (aq) (pH=0). After shaking in separatory funnel, the aqueous phase was removed. The organic phase was washed with 500 mL of 3 N HCl (aq) (pH=0), washed twice with 1 L of 10% $K_2CO_3$ (aq) (pH=12;12), washed three times with 500 mL of NaOCl (aq) solution, washed with 1L of water, washed with 1 L of 25% NaCl (aq), dried over $MgSO_4$, gravity filtered and concentrated under vacuum with dry ice trap to collect $Me_2S$. An amber oil of the title compound (107.01 g, 85.437 %) was obtained;

$^1$H NMR ($d^6$DMSO): δ 7.30–7.37 (m, 2H, phenyl C$\underline{H}$), 7.21–7.28 (m, 3H, phenyl C$\underline{H}$), 4.08 (q, J=6.9 Hz, 1H, —C$\underline{H}$(CH$_3$)Ph), 2.40–2.49 (m, 1H, cyclohexyl C$\underline{H}$), 1.82–1.84 (m, 1H, cyclohexyl —C$\underline{H}_2$), 1.67–169 (m, 1H, cyclohexyl —C$\underline{H}_2$), 1.52–1.63 (m, 1H, cyclohexyl —C$\underline{H}_2$), 1.34–1.43 (m, 1H, cyclohexyl —C$\underline{H}_2$), 1.26 (d, J=6.9 Hz, 3H, —CH(C$\underline{H}_3$)Ph), 1.01–1.24 (m, 4H, cyclohexyl —C$\underline{H}_2$).

Preparation of 2-Phenyl-2-methyl-4-pentenoyl Cyclohexane

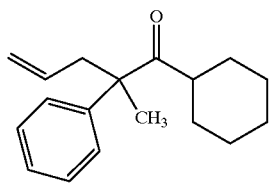

Scheme VI, step C; A solution of 31.39 g (0.2797 mol) of t-BuOK in 100 mL of THF was added dropwise to a solution of 55.00 g (0.2543 mol) of cyclohexyl 1-phenylethyl ketone and 26.4 mL (0.3052 mol) of allyl bromide in 136 mL of THF (cooled in a wet ice acetone bath). THF washings (16 mL) were added to the reaction mixture. The cooling bath was removed after addition. After reaction completion (2 h), the reaction mixture was quenched with 300 mL of 1 N HCl (pH=0) and extracted with 300 mL of heptane. The heptane extract was washed with 10% NaHCO$_3$ (aq) (pH=9), dried over MgSO$_4$, gravity filtered and concentrated under vacuum to afford 59.70 g (91.58%) of title compound as an amber oil: $^1$H NMR (d$^6$-DMSO): δ 7.32–7.42 (m, 2H, phenyl C$\underline{H}$), 7.24–7.31 m, 3H, phenyl C$\underline{H}$), 5.34–5.47 (m, 1H, —C$\underline{H}$=CH$_2$), 5.02 (dd, J=17.1 Hz, J=2.1 Hz, 1H, —C$\underline{H}$=CH—$\underline{H}$ (trans)), 4.97 (ddd, J=10.2 Hz, J=2.2 Hz, J=1.0 Hz, 1H, —C$\underline{H}$=CH—$\underline{H}$ (cis, W-coupling)), 2.66 (ddd, J=14.2 Hz, J=6.9 Hz, J=1.0 Hz, 1H, —C$\underline{H}_2$CH=CH$_2$), 2.59 (ddd, J=14.2 Hz, J=7.3 Hz, J=1.0 Hz, 1H, —C$\underline{H}_2$CH=CH$_2$), 2.38–2.49 (m, 1H, cyclohexyl C$\underline{H}$), 1.48–1.69 (m, 4H, cyclohexyl —C$\underline{H}_2$), 1.46 (s, 3H, —CH(C$\underline{H}_3$)Ph), 1.36–1.44 (m, 1H, cyclohexyl —C$\underline{H}_2$), 0.82–1.36 (m, 5H, cyclohexyl —C$\underline{H}_2$).

Preparation of 4-Cyclohexyl-3-methyl4-oxo-3-phenylbutyraldehyde

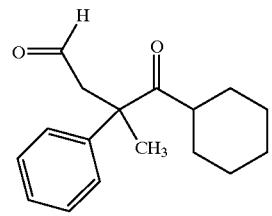

Scheme VI, step D: Ozone was bubbled through a cloudy mixture of 56.50 g (0.2204 mol) of 2-phenyl-2-methyl-4-pentenoyl cyclohexane and a small amount (~10 mg) of Sudan III in 220 mL of MeOH (cooled in a dry ice acetone bath at −20° C.) for 4 h until pink color turned to pale yellow color. After all of the olefin was consumed, Me$_2$S (50 mL) was added to reaction mixture. The cooling bath was removed. The exotherm rose to 38° C. and mixture was cooled in cooling bath until there was no exotherm. Then the cooling bath was removed and the mixture was stirred overnight. The reaction solution was concentrated under vacuum with dry ice trap to collect excess Me$_2$S to afford 83.65 g of crude 4-cyclohexyl-3-methyl-4-oxo-3-phenylbutyraldehyde dimethyl acetal as a pink oil:

$^1$H NMR (d$^6$-DMSO): δ 7.34–7.39 (m, 2H, phenyl C$\underline{H}$), 7.24–7.30 (m, 3H, phenyl C$\underline{H}$), 3.99 (dd, J=4.2 Hz, J=5.9 Hz, 1H, C$\underline{H}$(OCH$_3$)$_2$), 3.14 (s, 3H, CH(OC$\underline{H}_3$)$_2$), 3.06 (s, 3H, CH(OC$\underline{H}_3$)$_2$), 2.34–2.43 (m, 1H, cyclohexyl C$\underline{H}$), 2.10–2.20 (m, 2H, —C$\underline{H}_2$CH(OCH$_3$)$_2$), 1.55–1.67 (m, 1H, cyclohexyl —C$\underline{H}_2$), 1.53 (s, 3H, R$_2$C(CH$_3$)Ph), 0.80–1.52 (m, 9H, cyclohexyl —C$\underline{H}_2$).

To a solution of 82.65 g (66.29 g, 0.2177 mol) of 4-cyclohexyl-3-methyl-4-oxo-3-phenylbutyraldehyde dimethyl acetal in 539 mL of acetone was added 539 mL of 3 N HCl (aq) at RT. After reaction completion (2 h), the mixture was concentrated to 426.5 g (or 1/3 volume) of residue (RT −40° C.). The residue contained mostly water (pH=0) and was extracted twice with 300 mL of MTBE. The MTBE extract was washed with 300 mL of 25% NaCl (aq), dried over MgSO$_4$, gravity filtered and concentrated to afford 54.92 g (97.65%) of title compound as a pink oil: $^1$H NMR (d$^6$DMSO): δ 9.54 (t, J=2.0 Hz, 1H, —C$\underline{H}$O), 7.36–7.45 (m, 2H, phenyl C$\underline{H}$), 7.28–7.35 (m, 3H, phenyl C$\underline{H}$), 2.95 (dd, J=16.6 Hz, J=1.9 Hz, 1H, C$\underline{H}_2$CHO), 2.85 (dd, J=16.6 Hz, J=1.7 Hz, 1H, C$\underline{H}_2$CHO), 2.41–2.49 (m, 1H, cyclohexyl C$\underline{H}$), 1.72 (s, 3H, R$_2$C(CH$_3$)Ph), 0.85–1.66 (m, 10H, cyclohexyl —C$\underline{H}_2$).

Utilizing the aldehyde prepared in Example 28, the following compounds listed in Table II can readily be prepared by one of ordinary skill in the art in a manner analogous to the procedures described hereinabove. The compounds in Table II were not actually prepared.

TABLE II

| Example | Compound |
|---|---|
| 29 | *(structure)* |
| 30 | *(structure)* |
| 31 | *(structure)* |
| 32 | *(structure)* |
| 33 | *(structure)* |
| 34 | *(structure)* |
| 35 | *(structure)* |

TABLE II-continued

| Example | Compound |
|---|---|
| 36 | [Structure: 5-fluorobenzofuran-7-yl connected to piperidine-N-CH2CH2-C(CH3)(phenyl)-C(=O)-cyclohexyl] |

The following Table III provides additional compounds according to the present invention which can be prepared by one of ordinary skill in the art in a manner analogous to the procedures described hereinabove.

TABLE III

| Example | Compound | Melting Point |
|---|---|---|
| 37a | [Structure: 4-fluorobenzofuran-7-yl-tetrahydropyridine-N-CH2CH2-CH(2-pyridyl)-CH(OH)-cyclohexyl, diastereomer a, with oxalic acid] | 62–65° C. |
| 37b | [Structure: 4-fluorobenzofuran-7-yl-tetrahydropyridine-N-CH2CH2-CH(2-pyridyl)-CH(OH)-cyclohexyl, diastereomer b] | 160–165° C. |
| 38a | [Structure: 4-fluorobenzofuran-7-yl-piperidine-N-CH2CH2-CH(2-pyridyl)-CH(OH)-cyclohexyl, diastereomer a, with oxalic acid] | 94–98° C. |
| 38b | [Structure: 4-fluorobenzofuran-7-yl-piperidine-N-CH2CH2-CH(2-pyridyl)-CH(OH)-cyclohexyl, diastereomer b] | 52–55° C. |

TABLE III-continued

| Example | Compound | Melting Point |
|---------|----------|---------------|
| 39 | | 105–108° C. |
| 40 | | 95–98° C. |
| 41 | | 175–178° C. |
| 42 | | 100–102° C. |
| 43a | diastereomer a | 125–127° C. |
| 43b | diastereomer b | 130–132° C. |
| 44 | | 120–125° C. |

TABLE III-continued
| Example | Compound | Melting Point |
|---|---|---|
| 45 | 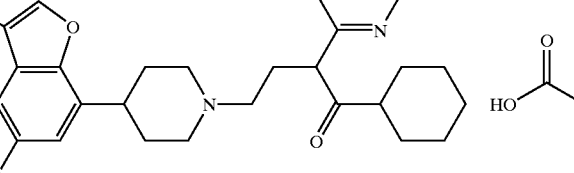 | Anal. C,H,N |
| 46 | 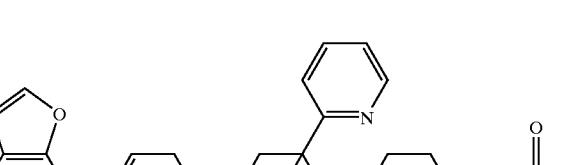 | 176–179° C. |
| 47 | 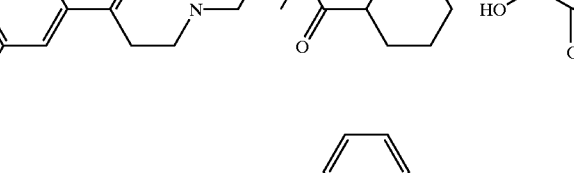 | 115–120° C. |
| 48 | 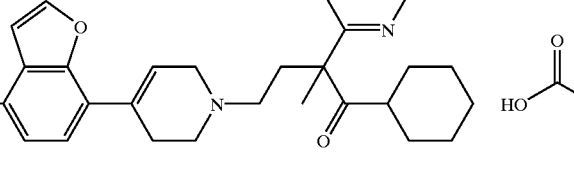 | 106–108° C. |
| 49 | 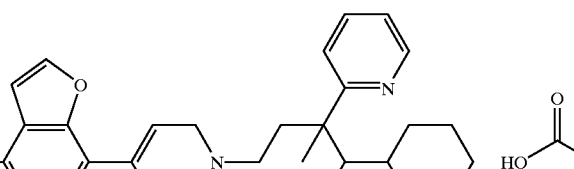 | 166–170° C. |
| 50 | 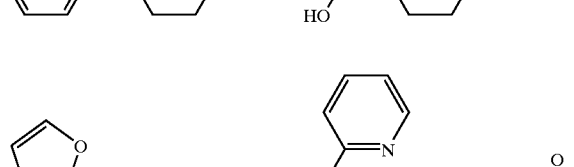 | 92–95° C. |

TABLE III-continued

| Example | Compound | Melting Point |
|---|---|---|
| 51 | | 175–180° C. |
| 52 | | 150–160° C. |
| 53 | | Enantiomer 1<br>90–95° C. |
| 54 | | Enantiomer 2<br>85–90° C. |
| 55 | | 85–90° C. |
| 56 | | Enantiomer 1<br>68–70° C. |
| 57 | | Enantiomer 2<br>90–94° C. |

TABLE III-continued

| Example | Compound | Melting Point |
|---|---|---|
| 58a | | Enantiomer 1<br>95–98° C. |
| 58b | | Enantiomer 2<br>97–100° C. |
| 59a | | Enantiomer 1<br>109–111° C. |
| 59b | | Enantiomer 2<br>158–160° C. |
| 60a | | Enantiomer 1<br>105–110° C. |
| 60b | | Enantiomer 2<br>115–120° C. |
| 61 | | 208–209° C. |

TABLE III-continued

| Example | Compound | Melting Point |
| --- | --- | --- |
| 62 | | 110–115° C. |
| 63a | | 79–81° C. |
| 63b | | 75–77° C. |
| 63c | | 84–86° C. |
| 63d | | 85–87° C. |
| 64 | | 167–170° C. |
| 65a | | 80–85° C. |

TABLE III-continued

| Example | Compound | Melting Point |
|---|---|---|
| 65b | | 85–90° C. |
| 66 | | 149–150° C. |
| 67 | | 163–165° C. |
| 68 | | 108–110° C. |
| 69a | | 100–107° C. |
| 69b | | 102–107° C. |

TABLE III-continued

| Example | Compound | Melting Point |
|---|---|---|
| 70 | | 160–161° C. |
| 71a | | 184–185° C. |
| 71b | | 100–105° C. |
| 72 | | 205–206° C. |
| 73 | | 115–120° C. |
| 74 | | 155–157° C. |
| 75 | | 91° C. |

TABLE III-continued

| Example | Compound | Melting Point |
|---|---|---|
| 76 | | 145–156° C. |
| 77 | | |
| 78 | | |
| 79 | | |
| 80a | | 78–82° C.<br>100% ee |
| 80b | | 71–75° C.<br>95.8% ee |
| 80c | | 80–84<br>95.4% ee |

TABLE III-continued

| Example | Compound | Melting Point |
|---|---|---|
| 80d | | 90–94° C. 98.0% ee |
| 81a | | 155–160° C. |
| 81b | | 155–160° C. |
| 82 | | 110–112° C. |
| 83 | | 110° C. |
| 84 | | 95–100° C. |
| 85 | | 110–112° C. |

TABLE III-continued

| Example | Compound | Melting Point |
|---|---|---|
| 86 | | 157–160° C. |
| 87 | | |
| 88 | | |
| 89 | | 203° C.(dec.) |
| 90 | | 82–85° C. |
| 91 | | |
| 92 | | 90–95° C. |

TABLE III-continued

| Example | Compound | Melting Point |
|---|---|---|
| 93 | (structure) | 255° C.(dec.) |
| 94 | (structure) | 130–133° C. |
| 95 | (structure) | Not prepared |
| 96 | (structure) | Not prepared |
| 97 | (structure) | Not prepared |
| 98 | (structure) | Not prepared |
| 99 | (structure) | Not prepared |

EXAMPLE 100

Preparation of:

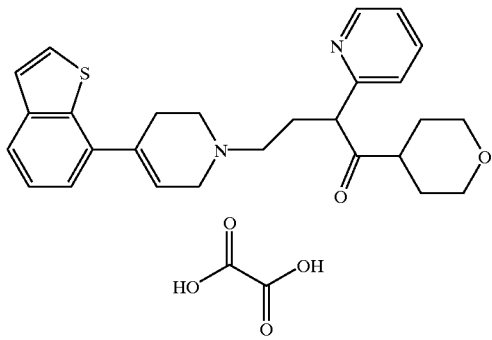

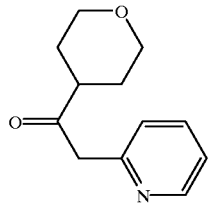

NaCN (2.85 g, 0.058 mol) was suspended in DMSO (22 mL) and heated to 140° C. To the stirring suspension was added 4-chlorotetrahydropyran (5.0 g, 0.041 mol). The reaction mixture was stirred at 135–145° C. for 1.5 hours and then cooled to room temperature. The reaction was diluted with water, extracted with ethyl acetate, dried over anhydrous sodium sulfate, filtered and concentrated under vacuum. The residue was passed through a silica gel plug eluting with hexane/ethyl acetate (1:1) to provide 4-cyanotetrahydropyran (0.65 g).

Picoline (0.58 mL, 5.85 mmol) was dissolved in THF (15 mL) and cooled to −78° C. The solution was treated with n-BuLi (3.84 mL of a 1.6 N solution in THF, 6.14 mmol). The solution was warmed to room temperature for 30 minutes and then recooled to −78° C. 4-cyanotetrahydropyran (0.65 g, 5.85 mmol, prepared above) dissolved in THF (5 mL) was added dropwise to the stirring solution. The reaction mixture was then warmed to room temperature and stirred for about 20 hours. It was then poured into water, stirred for 15 minutes and extracted with ethyl acetate (3×50 mL). The organic extracts were combined, dried over anhydrous sodium sulfate, filtered and concentrated under vacuum. The residue was purified by flash chromatography (silica gel, ethyl acetate) to provide the following ketone (0.78 g):

7-benzo(b)thiophene-1,2,3,6-tetrahydropyridyl (1.39 g, 6.40 mmol, prepared in example 1) was dissolved in methylene chloride (20 mL) and treated with 50% aqueous chloroacetaldehyde (1.64 mL, 12.9 mmol) followed by acetic acid (0.74 mL, 12.9 mmol) and sodium triacetoxyborohydride (2.73 g, 12.9 mmol). The reaction mixture was stirred at room temperature for one hour and then treated with 1N sodium hydroxide. The quenched reaction was extracted with methylene chloride, the organic extracts were dried over anhydrous sodium sulfate, filtered and concentrated under vacuum to provide the following 7-benzo(b)thiophene derivative as a brown oil:

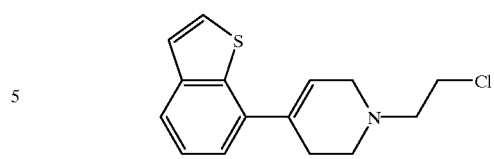

The ketone (1.0 g, 4.88 mmol, prepared above) was dissolved in DMF (20 mL) and cooled to 0° C. It was then treated with sodium hydride (60% dispersion, 0.20 g, 5.12 mmol) and stirred for 30 minutes at 0° C. and then warmed to room temperature. The 7-benzo(b)thiophene derivative (1.42 g, 5.12 mmol, prepared above) was dissolved in DMF (5 mL) and added to the reaction. The reaction mixture was then stirred at room temperature for 3 hours. Potassium iodide (0.1 g) was added and the reaction mixture was heated to 50° C. for 2 hours. The reaction was then quenched with water and extracted with ethyl acetate. The organic extracts were combined, washed with water (10 times), then brine, dried over anhydrous sodium sulfate, filtered and concentrated under vacuum. The residue was purified by flash chromatography (silica gel, 10% methanol/ethyl acetate) to provide the free base of the title compound. The free base was treated with oxalic acid under standard conditions to provide the title compound, mp 128–130° C.

EXAMPLE 101

Preparation of:

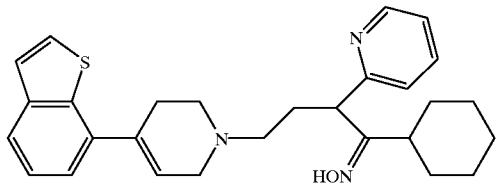

4-(7-benzo(b)thiophene-1,2,3,6-tetrahydropyridyl)-1-cyclohexyl-2-(2-pyridyl)butan-1-one (0.20 g, 0.45 mmol, prepared in example 1), and hydroxylamine hydrochloride (0.31 g, 4.5 mmol) were combined with water (7 mL) and ethanol (30 mL). The reaction mixture was heated at reflux for about 24 hours and then partially concentrated. The reaction mixture was then diluted with ethyl acetate, the organic layer was separated, washed with water, dried over anhydrous sodium sulfate, filtered and concentrated under vacuum. The residue was purified by flash chromatography (silica gel, 5% methanol/ethyl acetate) to provide the title compound (0.119 g), mp 88–92° C.

EXAMPLE 102

Preparation of:

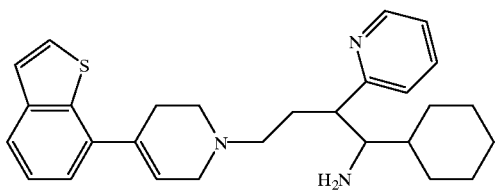

-continued

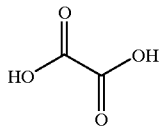

The title compound prepared in example 101 (0.30 g, 0.65 mmol) was dissolved in diethyl ether (50 mL) and treated with lithium aluminum hydride (0.10 g, 2.61 mmol, LAH). The reaction was stirred for about 18 hours and additional LAH (0.1 g, 2.61 mmol) was added. The reaction mixture was then heated at reflux for about 5 hours, then cooled and quenched with saturated potassium sodium tartrate solution (50 mL). The mixture was then extracted with ethyl acetate, the combined organic extracts were dried over anhydrous sodium sulfate, filtered and concentrated under vacuum. The residue was purified by flash chromatography (silica gel, 5% methanol/methylene chloride, 2MNH$_3$) to provide the purified free base (0.09 g). The free base was treated with oxalic acid to provide the title compound, mp 128° C.

EXAMPLE 103

Preparation of:

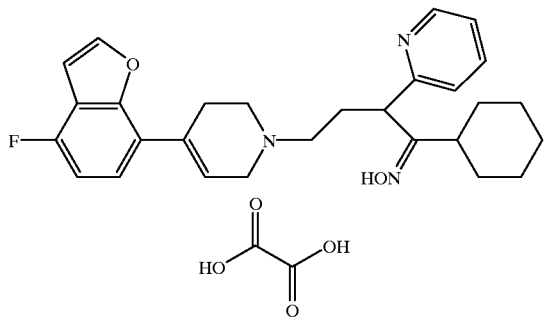

The title compound was prepared from 4-(4-fluoro-7-benzo(b)furan-1,2,3,6-tetrahydropyridyl)-1-cyclohexyl-2-(2-pyridyl)butan-1-one (prepared in example 17) and hydroxylamine hydrochloride in a manner analogous to the procedure described in example 101 above, mp 101–105° C.

EXAMPLE 104

Preparation of:

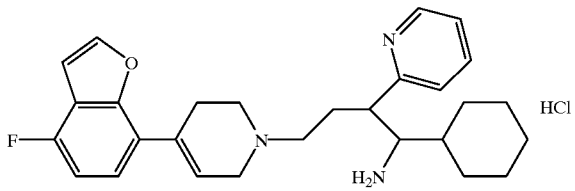

The title compound was prepared in a manner analogous to the procedure described in example 102 from the title compound prepared in example 103, and treatment with HCl rather than oxalic acid to provide the HCl salt.

EXAMPLE 105

Preparation of:

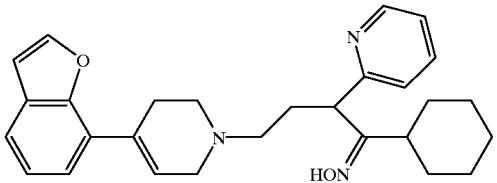

The title compound was prepared from 4-(7-benzo(b)furan-3,4-dehydropiperidinyl)-1-cyclohexyl-2-(2-pyridyl)butan-1-one (prepared in example 5) and hydroxylamine hydrochloride in a manner analogous to the procedure described in example 101 above, (0.38 g), mp 85–90° C.

EXAMPLE 106

Preparation of:

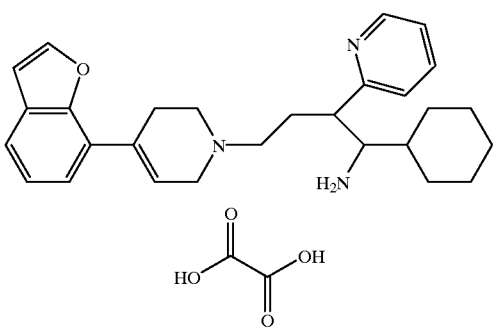

The title compound was prepared from the titel compound prepared in example 105 in a manner analogous to the procedure described in example 102, mp 152° C. (dec).

EXAMPLE 107

Preparation of:

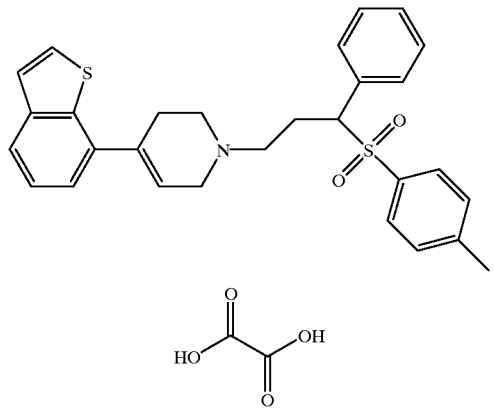

The following aldehyde:

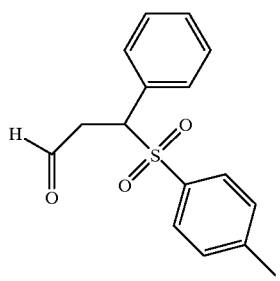

(0.20 g, 0.69 mmol) was combined with 7-benzo(b)thiophene-1,2,3,6-tetrahydropyridyl (0.15 g, 0.76 mmol, prepared in example 1) in methylene chloride (20 mL) and stirred for 20 minutes. The reaction mixture was then treated with acetic acid (0.06 mL, 1.04 mmol) and sodium triacetoxyborohydride (0.19 g, 0.90 mmol) and stirred for 2 hours. The reaction was then quenched with 1N sodium hydroxide and extracted with methylene chloride. The organic extracts were combined, dried over anhydrous sodium sulfate, filtered and concentrated under vacuum. The residue was purified by flash chromatography (silica gel, 50% ethyl acetate/hexane) to provide the free base of the title compound (0.117g). The free base was treated with oxalic acid (17.4 mg) under standard conditions to provide the title compound (0.08g), mp 122–125° C.

EXAMPLE 108

Preparation of

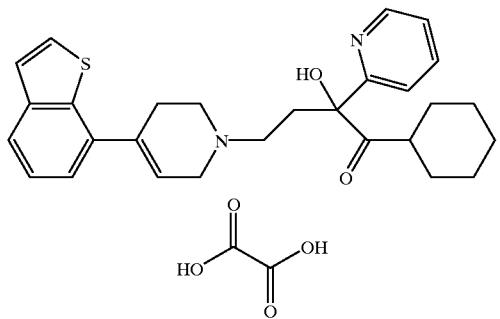

A 50 mL round bottom flask was charged with 4-(7-benzo(b)thiophene-3,4-dehydropiperidinyl)-1-(2-pyridyl)-2-cyclohexyl-butan-1-one (0.50 g, 1.12 mmole, prepared in example 1) and dimethylsulfoxide (10 mL). The solution was treated with potassium hydroxide (0.20 g, 3.56 mmole) dissolved in tetrahydrofuran/water (5 mL/1 mL) at room temperature. The solution was then warmed to 50° C. for 30 minutes. Then, 36% aqueous formaldehyde solution (0.09 g, 1.12 mmole) was added. The reaction mixture was stirred at room temperature for 3 hours. The reaction mixture was diluted with ethyl acetate. The organic layer was separated and dried over anhydrous sodium sulfate, then filtered and concentrated under vacuum. The residue was purified by flash chromatography to provide the free base the title compound (0.03 g). The free base form was dissolved in methanol and treated with oxalic acid (5.9 mg) to obtain the title compound, mp 110° C.

EXAMPLE 109

Preparation of

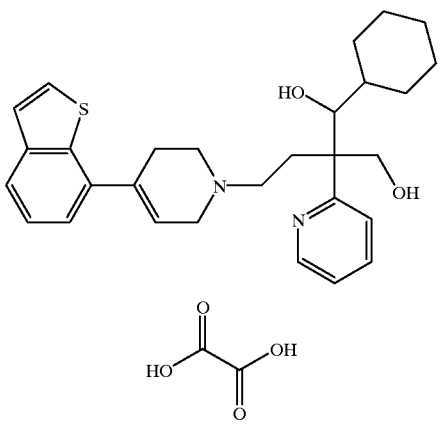

A 50 mL round bottom flask was charged with 4-(7-benzo(b)thiophene-3,4-dehydropiperidinyl)-1-(2-pyridyl)-2-cyclohexyl-butan-1-one (0.50 g, 1.12 mmole, prepared in example 1) and dimethylsulfoxide (10 mL). The solution was treated with potassium hydroxide (0.20 g, 3.56 mmole) dissolved in tetrahydrofuran/water (5 mL/1 mL) at room temperature. The solution was warmed to 50° C. for 30 minutes. Then, 36% aqueous formaldehyde solution (0.09 g, 1.12 mmole) was added. The reaction mixture was stirred at room temperature for 3 hours. The reaction mixture was diluted with ethyl acetate. The organic layer was separated and dried over anhydrous sodium sulfate, then filtered and concentrated under vacuum. The residue was purified by flash chromatography to provide the free base the title compound (0.04 g). The free base form was dissolved in methanol and treated with oxalic acid (7.5 mg) to obtain the title compound, mp 115–120° C. (dec).

EXAMPLE 110

Preparation

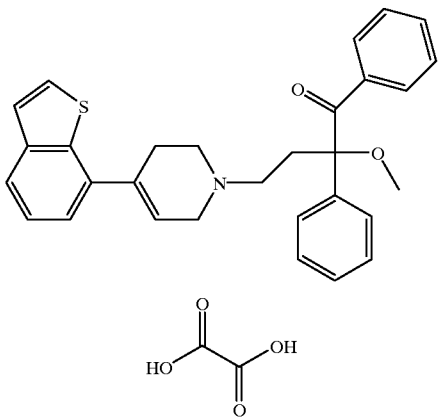

A 50 mL round bottom flask was charged with 2-methoxy-2-phenylacetophenone and N,N-dimethylformamide (10 mL). The solution was cooled to 0° C. and was treated with 60% suspension of sodium hydride in oil (0.18 g, 4.42 mmole). The slurry was warmed slowly to room temperature over 45 minutes. Then 1-[4-(7-benzo(b)thiophene-3,4-dehydropiperidinyl]-2-chloroethane (0.48 g, 1.73 mmole) dissolved in N,N-dimethylformamide (5 mL) was added dropwise. The reaction mixture was stirred at room temperature for 16 hours. The reaction mixture was then diluted with water and extracted with ethyl acetate. The organic layer was washed with water and saturated sodium chloride solution. The organic layer was dried over anhydrous sodium sulfate, filtered and concentrated under vacuum. The residue was purified by flash chromatography to provide the free base of the title compound (0.024 g). The free base was dissolved in methanol, treated with oxalic acid (4.6 mg) and concentrated under vacuum to provide the title compound, mp 100–102° C.

Serotonin-$1_A$ Receptor and Serotonin-$2_A$ Receptor Activity

The compounds of the present invention are active at the serotonin-$1_A$ receptor and at the serotonin-$2_A$ receptor, particularly as antagonists and as partial agonists at that receptor. Previously known compounds with that activity typically have the disadvantage of possessing other non-serotonin related central nervous system activities as well. It is now well understood by pharmacologists and physicians that pharmaceuticals which have a single physiological activity, or which are much more active in the desired activity than in their other activities, are much more desirable for therapy than are compounds which have multiple activities at about the same dose.

The 5-$HT_{1A}$ receptor binding potency and the 5-$HT_{2a}$ receptor binding potency of the present compounds are measured by techniques well known in the art. For example, the 5-$HT_{1A}$ receptor binding potency is measured by a modification of the binding assay described by Taylor, et al. (*J. Pharmacol. Exp. Ther.* 236, 118–125, 1986); and Wong, et al., *Pharm. Biochem. Behav.* 46, 173–77 (1993). Membranes for the binding assay are prepared from male Sprague-Dawley rats (150–250 g). The animals are killed by decapitation, and the brains are rapidly chilled and dissected to obtain the hippocampi. Membranes from the hippocampi are either prepared that day, or the hippocampi are stored frozen (−70°) until the day of preparation. The membranes are prepared by homogenizing the tissue in 40 volumes of ice-cold Tris-HCl buffer (50 mM, pH 7.4 at 22°) using a homogenizer for 15 sec., and the homogenate is centrifuged at 39800×g for 10 min. The resulting pellet is then resuspended in the same buffer, and the centrifugation and resuspension process is repeated three additional times to wash the membranes. Between the second and third washes the resuspended membranes are incubated for 10 min. at 37° to facilitate the removal of endogenous ligands. The final pellet is resuspended in 67 mM Tris-HCl, pH 7.4, to a concentration of 2 mg of tissue original wet weight/200 $\mu$l. This homogenate is stored frozen (−70°) until the day of the binding assay. Each tube for the binding assay has a final volume of 800 $\mu$l and contains the following: Tris-HCl (50 mM), pargyline (10 $\mu$M), CaCl$_2$ (3 mM), [$^3$H]8-OH-DPAT (1.0 nM), appropriate dilutions of the drugs of interest, and membrane resuspension equivalent to 2 mg of original tissue wet weight, for a final pH of 7.4. The assay tubes are incubated for either 10 min. or 15 min. at 37°, and the contents are then rapidly filtered through GF/B filters (pretreated with 0.5% polyethylenimine), followed by four one-ml washes with ice-cold buffer. The radioactivity trapped by the filters is quantitated by liquid scintillation spectrometry, and specific [3H]8-OH-DPAT binding to the 5-HT1A sites is defined as the difference between [3H]8-OH-DPAT bound in the presence and absence of 10 $\mu$M 5-HT.

IC50 values, i.e., the concentration required to inhibit 50% of the binding, are determined from 12-point competition curves using nonlinear regression (SYSTAT, SYSTAT, Inc., Evanston, Ill.). IC50 values are converted to Ki values using the Cheng-Prusoff equation (Biochem. Pharmacol., 22, 3099–3108 (1973).

Additional binding assays of some of the present compounds are carried out by an assay method which uses a cloned cell line which expresses the serotonin-1A receptor, rather than the hippocampal membranes. Such cloned cell lines have been described by Fargin, et al., J.Bio. Chem., 264, 14848–14852 (1989), Aune, et al., J. Immunology, 151, 1175–1183 (1993), and Raymond, et al., Naunyn-Schmiedeberg's Arch. Pharmacol., 346, 127–137 (1992). Results from the cell line assay are substantially in agreement with results from the hippocampal membrane assay.

As was reported by R. L. Weinshank, et al., WO93/14201, the 5-HT1A receptor is functionally coupled to a G-protein as measured by the ability of serotonin and serotonergic drugs to inhibit forskolin stimulated cAMP productionin NIH3T3 cells transfected with the 5-HT1A receptor. Adenylate cyclase activity is determined using standard techniques. A maximal effect is achieved by serotonin. An Emax is determined by dividing the inhibition of a test compound by the maximal effect and determining a percent inhibition. (N. Adham, et al., supra,; R. L. Weinshank, et al., Proceedings of the National Academy of Sciences (USA), 89,3630–3634 (1992)), and the references cited therein.

[$^{35}$S]GTPγS Binding Method

Agonist activation of G protein-coupled receptors results in the release of GDP (guanosine-5'-diphosphate) from the γ-subunit of the G protein and the subsequent binding of GTP (guanosine-5'-triphosphate). The binding of the stable analogue [$^{35}$S]GTPγS (guanosine 5'-O-[3-thiotriphosphate]) can be used as an indicator of this receptor activation (see Wieland, T., Jakobs, K. H., 1994. Measurement of receptor-stimulated guanosine 5'-O-(γ-thio)triphosphate binding by G proteins. *Methods Enzymol.* 237, 3–13.). EC$_{50}$ and efficacy (E$_{max}$) values can be determined. Similarly, antagonists will inhibit agonist-stimulated [$^{35}$S]GTPγS binding. From these experiments, IC$_{50}$ values, converted to a dissociation constant, e.g. K$_i$, and efficacy (E$_{max}$) values can be determined by one of ordinary skill in the art.

Measurement of cAMP Formation

Transfected NIH3T3 cells (estimated Bmax from one point competition studies=488 fmol/mg of protein) are incubated in DMEM, 5 mM theophylline, 10 mM HEPES (4-[2-hydroxyethyl]-1-piperazineethanesulfonic acid) and 10 $\mu$M pargyline for 20 minutes at 37° C., 5% carbon dioxide. Drug dose-effect curves are then conducted by adding 6 different final concentrations of drug, followed immediately by the addition of forskolin (10 mM). Subsequently, the cells are incubated for an additional 10 minutes at 37° C., 5% carbon dioxide. The medium is aspirated and the reaction is stopped by the addition of 100 mM hydrochloric acid. To demonstrate competitive antagonism, a dose-response curve for 5-HT is measured in parallel, using a fixed dose of methiothepin (0.32 mM). The plates are stored at 4° C. for 15 minutes and then centrifuged for 5 minutes at 500×g to pellet cellular debris, and the supernatant is aliquoted and stored at −20° C. before assessment of cAMP formation by radioimmunoassay (cAMP radioimmunoassay kit; Advanced Magnetics, Cambridge, Mass.). Radioactivity is quantified using a Packard COBRA Auto Gamma counter, equipped with data reduction software. Representative compounds are tested for 5-HT$_{1A}$ receptor antagonist activity in the cAMP assay.

5HT$_{1a}$ Antagonist, In Vivo Tests a) 5HT$_{1a}$ Antagonism Subcutaneous Test

Compounds ware tested over a range of subcutaneous doses for activity in blocking the B-OH-DPAT induced behaviors and hypothermia. Lower lip retraction (LLR) and flat body posture (FBP) are recorded in male Sprague Dawley rats (~250 grams from Harlan Sprague Dawley). Both LLR and FBP are measured on a scale of 0–3 (Wolff et al, 1997). In the LLR behavioral assay, "0" indicates normal lip position; "1" indicates a slight separation of the lips; "2" indicates that the lips are open with some teeth visible; "3" indicates that the lips are fully open with all the front teeth exposed. In the FBP assay, a score of "0" indicates normal body posture; "1" indicates that the stomach is on the floor with the back in its normal rounded position; "2" indicates that the stomach is on the floor with the back straightened and rising from the shoulders to the hips; "3" indicates that the stomach is pressed into the floor and the back is flattened with the shoulders and hips even. Core body temperature is recorded by rectal probe inserted 5.0 cm immediately after the behavioral measures. Rats are injected subcutaneous with compound (at 0, 0.3, 1.0 and 3.0 mg/kg) 35 minutes before scoring and the 8-OH-DPAT (0.1 mg/kg subcutaneous) is injected 20 minutes before scoring.

b) $5HT_{1a}$ Agonist Subcutaneous Test

The compounds are also tested at a high dose of 10 mg/kg subcutaneous alone to see if they induced $5HT_{1a}$ agonist-like hypothermia.

The efficacy of the compounds of the invention to inhibit the reuptake of serotonin is determined by a paroxetine binding assay, the usefulness of which is set out by Wong, et al., *Neuropschopharmacology*, 8, 23–33 (1993). Synaptosomal preparations from rat cerebral cortex are made from the brains of 100–150 g Sprague-Dawley rats which are killed by decapitation. The cerebral cortex is homogenized in 9 volumes of a medium containing 0.32 M sucrose and 20 $\mu$M glucose. The preparations are resuspended after centrifugation by homogenizing in 50 volumes of cold reaction medium (50 $\mu$M sodium chloride, 50 $\mu$M potassium chloride, pH 7.4) and centrifuging at 50,000 g for 10 minutes. The process is repeated two times with a 10-minute incubation at 37° C. between the second and third washes. The resulting pellet is stored at −70° C. until use. Binding of $^3$H-paroxetine to 5-HT uptake sites is carried out in 2 ml reaction medium containing the appropriate drug concentration, 0.1 nM $^3$H-paroxetine, and the cerebral cortical membrane (50 $\mu$g protein/tube). Samples are incubated at 37° C. for 30 minutes; those containing 1 $\mu$M fluoxetine are used to determine nonspecific binding of $^3$H-paroxetine. After incubation, the tubes are filtered through Whatman GF/B filters, which are soaked in 0.05% polyethylenimine for 1 hour before use, using a cell harvester by adding about 4 ml cold Tris buffer (pH 7.4), aspirating, and rinsing the tubes three additional times. Filters are then placed in scintillation vials containing 10 ml scintillation fluid, and the radioactivity is measured by liquid scintillation spectrophotometry.

The pharmacological activities which have been described immediately above provide the mechanistic basis for the pharmaceutical utility of the compounds described in this document. A number of pharmaceutical utilities will be described below.

Throughout this document, the person or animal to be treated will be described as the "subject", and it will be understood that the most preferred subject is a human. However, it must be noted that the study of adverse conditions of the central nervous system in non-human animals is only now beginning, and that some instances of such treatments are coming into use. For example, fluoxetine, and perhaps other serotonin reuptake inhibitors, are being used in companion animals such as dogs for the treatment of behavioral problems and the like. Accordingly, use of the present compounds in non-human animals is contemplated.

It will be understood that the dosage ranges for other animals will necessarily be quite different from the doses administered to humans, and accordingly that the dosage ranges described below in the section on tobacco withdrawal must be recalculated. For example, a small dog may be only 1/10th of a typical human's size, and it will therefore be necessary for a much smaller dose to be used. The determination of an effective amount for a certain non-human animal is carried out in the same manner described below in the case of humans, and veterinarians are well accustomed to such determinations.

The activity of the compounds at the serotonin-1A receptor provides a method of affecting the serotonin-1 A receptor which comprises administering to a subject in need of such treatment an effective amount of a compound of formula I. Reasons for the necessity of affecting the serotonin-1A receptor will be described in detail below, but in all cases the effect on the serotonin-1A receptor is brought about through the compounds' potency as antagonists or partial agonists at that receptor. A subject in need of a modification of the effects of the $5-HT_{1A}$ receptor is one having one or more of the specific conditions and problems to be further described, or a condition or problem not yet recognized as created by an imbalance or malfunction of the $5-HT_{1A}$ receptor, since research on the central nervous system is presently ongoing in many fields and newly discovered relationships between receptors and therapeutic needs are continually being discovered.

An effective amount of a compound for affecting the serotonin-1A receptor is the amount, or dose, of the compound which provides the desired effect in the subject under diagnosis or treatment. The effective amount of compound to be administered, in general, is from about 1 to about 200 mg/day; as usual, the daily dose may be administered in a single bolus, or in divided doses, depending on the judgment of the physician in charge of the case. A more preferred range of doses is from about 5 to about 100 mg/day; other dosage ranges which may be preferred in certain circumstances are from about 10 to about 50 mg/day; from about 5 to about 50 mg/day; from about 10 to about 25 mg/day; and a particularly preferred range is from about 20 to about 25 mg/day.

The amount is an individualized determination, and physicians are well accustomed to adjusting effective amounts of pharmaceuticals based on observations of the subject. The effective amount of the present compounds is discussed in some detail below, in the discussion about the treatment of tobacco withdrawal symptoms, and that discussion is applicable, in an analogous manner to the determination of the effective amount in all treatment methods.

In a manner analogous to the above, the activity of the compounds at the serotonin-2A receptor provides a method of affecting the serotonin-2A receptor which comprises administering to a subject in need of such treatment an effective amount of a compound of formula I.

Further, the activity of compounds of formula I in the inhibition of the reuptake of serotonin provides a method of inhibiting the reuptake of serotonin comprising administering to a subject in need of such treatment an effective amount of a compound of that formula. An effective amount of a compound for inhibiting the reuptake of serotonin is the amount, or dose, of the compound which provides the desired effect in the subject under diagnosis or treatment. The amount is an individualized determination, and physicians are well accustomed to adjusting effective amounts of pharmaceuticals based on observations of the subject. It is now known that numerous physiological and therapeutic benefits are obtained through the administration of drugs which inhibit the reuptake of serotonin. The treatment of depression with drugs of the class of which fluoxetine is the leader has become perhaps the greatest medical breakthrough of the past decade. Numerous other treatment methods carried out by the administration of the compounds of formula I will be set out in detail below. Again, the effective amount of a compound for the inhibition of serotonin reuptake, or for a specific therapeutic method which depends on the inhibition of reuptake, is determined in the manner analogous to that described below under the heading of smoking withdrawal.

The unique combination of $5-HT_{1A}$ receptor activity, $5-HT_{2A}$ receptor activity, and serotonin reuptake inhibition possessed by the compounds of the invention afford a method of providing to a subject both physiological activities with a single administration of a compound of that formula. It is believed that the present compounds are advantageous in that they provide all three physiological effects in a single drug. It is presently believed that the result of administration of a compound of formula I is to provide physiological and therapeutic treatment methods which are typical of those provided by presently known serotonin reuptake inhibitors, but with enhanced efficacy, quicker onset of action and reduced side effects.

The activities of compounds of formula I at the $5-HT_{1A}$ receptor, the $5-HT_{2A}$ receptor, and in reuptake inhibition are of comparable potencies, so a single effective amount as defined hereinabove for affecting the serotonin-1A receptor, the serotonin-2A receptor, or for inhibiting the reuptake of serotonin, is effective for affecting the serotonin-1A receptor, the serotonin-2A receptor, and for inhibiting the reuptake of serotonin in a subject.

Further discussion of specific therapeutic methods provided by the activity compounds of formula I, and the diseases and conditions advantageously treated therewith, are provided below.

Tobacco or Nicotine Withdrawal

It is well known that the chronic administration of nicotine results in tolerance and, eventually, dependence. The use of tobacco has become extremely widespread in all countries, despite the well known adverse effects of the use of tobacco in all its forms. Thus, it is clear that tobacco use is extremely habit-forming, if not addictive, and that its use provides sensations to the user which are pleasant and welcome, even though the user may be fully aware of the drastic long term ill effects of its use.

Rather recently, vigorous campaigns against the use of tobacco have taken place, and it is now common knowledge that the cessation of smoking brings with it numerous unpleasant withdrawal symptoms, which include irritability, anxiety, restlessness, lack of concentration, lightheadedness, insomnia, tremor, increased hunger and weight gain, and, of course, a craving for tobacco.

At the present time, probably the most widely used therapy to assist the cessation of tobacco use is nicotine replacement, by the use of nicotine chewing gum or nicotine-providing transdermal patches. It is widely known, however, that nicotine replacement is less effective without habit-modifying psychological treatment and training.

Thus, the present method of preventing or alleviating the symptoms caused by withdrawal or partial withdrawal from the use of tobacco or of nicotine comprises the previously discussed method of affecting the serotonin-1A receptor, in that the treatment method comprises the administration of an effective amount of one of the serotonin-1A receptor-active compounds of formula I to the subject. The method of the present invention is broadly useful in assisting persons who want to cease or reduce their use of tobacco or nicotine. Most commonly, the form of tobacco use is smoking, most commonly the smoking of cigarettes. The present invention is also helpful, however, in assisting in breaking the habit of all types of tobacco smoking, as well as the use of snuff, chewing tobacco, etc. The present method is also helpful to those who have replaced, or partially replaced, their use of tobacco with the use of nicotine replacement therapy. Thus, such subjects can be assisted to reduce and even eliminate entirely their dependence on nicotine in all forms.

A particular benefit of therapy with the present compounds is the elimination or reduction of the weight gain which very often results from reducing or withdrawing from use of tobacco or nicotine.

It will be understood that the present invention is useful for preventing or alleviating the withdrawal symptoms which afflict subjects who are trying to eliminate or reduce their use of tobacco or nicotine. The common withdrawal symptoms of such people include, at least, irritability, anxiety, restlessness, lack of concentration, insomnia, nervous tremor, increased hunger and weight gain, lightheadedness, and the craving for tobacco or nicotine. The prevention or alleviation of such symptoms, when they are caused by or occur in conjunction with ceasing or reducing the subject's use of tobacco or nicotine is a desired result of the present invention and an important aspect of it.

The invention is carried out by administering an effective amount of a compound of formula I to a subject who is in need of or carrying out a reduction or cessation of tobacco or nicotine use.

It will be understood that the effective amount for a given subject is always to be set by the judgment of the attending physician, and that the dose is subject to modification based on the size of the subject, the lean or fat nature of the subject, the characteristics of the particular compound chosen, the intensity of the subjects tobacco habit, the intensity of the subjects withdrawal symptoms, and psychological factors which may affect the subject's physiological responses. Thus, the effective amount is the amount required to prevent or alleviate the symptoms of withdrawal or partial withdrawal in the subject under treatment.

In effecting treatment of a subject as described herein, a compound of formula I can be administered in any form or mode which makes the compound bioavailable in effective amounts, including oral and parenteral routes. For example, compounds of formula I can be admininstered orally, subcutaneously, intramuscularly, intravenously, transdermally, intranasally, rectally, and the like. Oral administration is the preferred route for compounds of formula I.

The effect of compounds in alleviating the symptoms of nicotine withdrawal is evaluated in rats by an auditory startle test, which is carried out as follows.

Procedures for Nicotine Withdrawal Studies

Animals: Male Long Evans rats are individually housed in a controlled environment on a 12 hour light-dark cycle and are given free access to food (Purina Rodent Chow) and water. All treatment groups contain 8–10 rats.

Chronic Nicotine Treatment: Rats are anesthetized with halothane and Alzet osmotic minipumps (Alza Corporation, Palo Alto, Calif., Model 2ML2) are implanted subcutaneously. Nicotine ditartrate is dissolved in physiological saline. Pumps are filled with either nicotine ditartrate (6 mg/kg base/day) or physiological saline. Twelve days following implantation of pumps, rats are anesthetized with halothane and the pumps are removed.

Auditory Startle Response: The sensory motor reactions [auditory startle response (peak amplitude Vmax)] of individual rats is recorded using San Diego Instruments startle chambers (San Diego, Calif.). Startle sessions consist of a 5-minute adaptation period at a background noise level of 70±3 dBA immediately followed by 25 presentations of auditory stimuli (120±2 dBA noise, 50 ms duration) presented at 8-second intervals. Peak startle amplitudes are then averaged for all 25 presentations of stimuli for each session. Auditory startle responding is evaluated daily at 24 hour intervals on days 1–4 following nicotine withdrawal.

Combination With Reuptake Inhibitors

A further application of the compounds of formula I is their use in combination with a serotonin reuptake inhibitor to potentiate the action of those drugs by increasing the availability of serotonin, as well as norepinephrine and dopamine, in the brain of patients to whom the drug combination is administered. Typical and appropriate reuptake inhibitors (SRI) are fluoxetine, duloxetine, venlafaxine, milnacipran, citalopram, fluvoxamine and paroxetine. Accordingly, the present invention provides a method for potentiating the action of a serotonin reuptake inhibitor, particularly one of the group consisting of fluoxetine, duloxetine, venlafaxine, milnacipran, citalopram, fluvoxamine and paroxetine, in increasing the availability of serotonin, norepinephrine and dopamine in the brain, comprising administering said serotonin reuptake inhibitor in combination with a compound of formula I. The invention also provides pharmaceutical compositions which comprise a serotonin reuptake inhibitor in combination with a compound of formula I, and a method of treating a pathological condition which is created by or is dependent upon decreased availability of serotonin, dopamine or norepinephrine, which method comprises administering the same adjunctive therapy to a patient in need of such treatment.

It will be understood that, while the compounds of formula I individually provide the benefit of the combination of serotonin reuptake inhibitors and serotonin-1A antagonists and serotonin-2A antagonists, it is entirely possible to administer a compound of formula I in combination with a conventional serotonin reuptake inhibitor in order to obtain still further enhanced results in potentiating serotonin reuptake inhibition. Examples of representative serotonin reuptake inhibitors include but are not limited to the following:

Fluoxetine, N-methyl-3-(p-trifluoromethylphenoxy)-3-phenylpropylamine, is marketed in the hydrochloride salt form, and as the racemic mixture of its two enantiomers. U.S. Pat. No. 4,314,081 is an early reference on the compound. Robertson, et al., *J. Med. Chem.* 31, 1412 (1988), taught the separation of the R and S enantiomers of fluoxetine and showed that their activity as serotonin uptake inhibitors is similar to each other. In this document, the word "fluoxetine" will be used to mean any acid addition salt or the free base, and to include either the racemic mixture or either of the R and S enantiomers.

Duloxetine, N-methyl-3-(1-naphthalenyloxy)-3-(2-thienyl)propanamine, is usually administered as the hydrochloride salt and as the (+) enantiomer. It was first taught by U.S. Pat. No. 4,956,388, which shows its high potency. The word "duloxetine" will be used here to refer to any acid addition salt or the free base of the molecule.

Venlafaxine is known in the literature, and its method of synthesis and its activity as an inhibitor of serotonin and norepinephrine uptake are taught by U.S. Pat. No. 4,761,501. Venlafaxine is identified as compound A in that patent.

Milnacipran (N,N-diethyl-2-aminomethyl-1-phenylcyclopropanecarboxamide) is taught by U.S. Pat. No. 4,478,836, which prepared milnacipran as its Example 4. The patent describes its compounds as antidepressants. Moret, et al., *Neuropharmacology* 24, 1211–19(1985), describe its pharmacological activities.

Citalopram, 1-[3-(dimethylamino)propyl]-1-(4-fluorophenyl)-1,3-dihydro-5-isobenzofurancarbonitrile, is disclosed in U.S. Pat. No. 4,136,193 as a serotonin reuptake inhibitor. Its pharmacology was disclosed by Christensen, et al., *Eur. J. Pharmacol.* 41, 153 (1977), and reports of its clinical effectiveness in depression may be found in Dufour, et al., *Int. Clin. Psychopharmacol.* 2, 225 (1987), and Timmerman, et al., ibid., 239.

Fluvoxamine, 5-methoxy-1-[4-(trifluoromethyl)phenyl]-1-pentanone 0-(2-aminoethyl)oxime, is taught by U.S. Pat. No. 4,085,225. Scientific articles about the drug have been published by Claassen, et al., *Brit. J. Pharmacol.* 60, 505 (1977); and De Wilde, et al., *J. Affective Disord.* 4, 249 (1982); and Benfield, et al., *Drugs* 32, 313 (1986).

Sertraline, 1-(3,4-dichlorophenyl)-4-methylaminotetralin, is disclosed in U.S. Pat. No. 4,536,518.

Paroxetine, trans-(−)-3-[(1,3-benzodioxol-5-yloxy) methyl]-4-(4-fluorophenyl)piperidine, may be found in U.S. Pat. Nos. 3,912,743 and 4,007,196. Reports of the drug's activity are in Lassen, *Eur. J. Pharmacol.* 47, 351 (1978); Hassan, et al., *Brit. J. Clin. Pharmacol.* 19, 705 (1985); Laursen, et al., *Acta Psychiat. Scand.* 71, 249 (1985); and Battegay, et al., *Neuropsychobiology* 13, 31 (1985).

All of the U.S. patents which have been mentioned above in connection with compounds used in the present invention are incorporated herein by reference.

Fluoxetine or duloxetine are the preferred SRI's in pharmaceutical compositions combining a compound of formula I and an SRI, and the corresponding methods of treatment.

It will be understood by the skilled reader that all of the compounds used in the present invention are capable of forming salts, and that the salt forms of pharmaceuticals are commonly used, often because they are more readily crystallized and purified than are the free bases. In all cases, the use of the pharmaceuticals described above as salts is contemplated in the description herein and often is preferred, and the pharmaceutically acceptable salts of all of the compounds are included in the names of them.

The dosages of the drugs used in the present combination must, in the final analysis, be set by the physician in charge of the case, using knowledge of the drugs, the properties of the drugs in combination as determined in clinical trials, and the characteristics of the subject, including diseases other than that for which the physician is treating the subject. General outlines of the dosages, and some preferred human dosages, can and will be provided here. Dosage guidelines for some of the drugs will first be given separately; in order to create a guideline for any desired combination, one would choose the guidelines for each of the component drugs.

Fluoxetine: from about 1 to about 80 mg, once/day; preferred, from about 10 to about 40 mg once/day; preferred for bulimia and obsessive-compulsive disease, from about 20 to about 80 mg once/day;

Duloxetine: from about 1 to about 30 mg once/day; preferred, from about 5 to about 20 mg once/day;

Venlafaxine: from about 10 to about 150 mg once-thrice/day; preferred, from about 25 to about 125 mg thrice/day;

Milnacipran: from about 10 to about 100 mg once-twice/day; preferred, from about 25 to about 50 mg twice/day;

Citalopram: from about 5 to about 50 mg once/day; preferred, from about 10 to about 30 mg once/day;

Fluvoxamine: from about 20 to about 500 mg once/day; preferred, from about 50 to about 300 mg once/day;

Paroxetine: from about 5 to about 100 mg once/day; preferred, from about 50 to about 300 mg once/day.

In more general terms, one would create a combination of the present invention by choosing a dosage of SRI according to the spirit of the above guideline, and choosing a dosage of the compound of formula I in the ranges taught above.

The adjunctive therapy of the present invention is carried out by administering a SRI together with a compound of formula I in any manner which provides effective levels of the two compounds in the body at the same time. All of the compounds concerned are orally available and are normally administered orally, and so oral administration of the adjunctive combination is preferred. They may be administered together, in a single dosage form, or may be administered separately.

However, oral administration is not the only route or even the only preferred route. For example, transdermal administration may be very desirable for patients who are forgetful or petulant about taking oral medicine. One of the drugs may be administered by one route, such as oral, and the other may be administered by the trans-dermal, percutaneous, intravenous, intramuscular, intranasal or intrarectal route, in particular circumstances. The route of administration may be varied in any way, limited by the physical properties of the drugs and the convenience of the patient and the caregiver.

It is particularly preferred, however, for the adjunctive combination to be administered as a single pharmaceutical composition, and so pharmaceutical compositions incorporating both a SRI and a compound of formula I are important embodiments of the present invention. Such compositions may take any physical form which is pharmaceutically acceptable, but orally usable pharmaceutical compositions are particularly preferred. Such adjunctive pharmaceutical compositions contain an effective amount of each of the compounds, which effective amount is related to the daily dose of the compounds to be administered. Each adjunctive dosage unit may contain the daily doses of both compounds, or may contain a fraction of the daily doses, such as one-third of the doses. Alternatively, each dosage unit may contain the entire dose of one of the compounds, and a fraction of the dose of the other compound. In such case, the patient would daily take one of the combination dosage units, and one or more units containing only the other compound. The amounts of each drug to be contained in each dosage unit depends on the identity of the drugs chosen for the therapy, and other factors such as the indication for which the adjunctive therapy is being given.

As stated above, the benefit of the adjunctive therapy is its ability to augment the increase in availability of serotonin, norepinephrine and dopamine caused by the SRI compounds, resulting in improved activity in treating the various conditions described below in detail. The increase in availability of serotonin is particularly important and is a preferred aspect of the invention. Further, the invention provides a more rapid onset of action than is usually provided by treatment with the SRI alone.

Preferred pathological conditions to be treated by the methods disclosed herein include depression, bulimia, obsessive-compulsive disease and obesity. Another preferred condition more specific to combinations including preferably duloxetine but also venlafaxine and milnacipran is urinary incontinence.

Depression in its many variations has recently become much more visible to the general public than it has previously been. It is now recognized as an extremely damaging disorder, and one that afflicts a surprisingly large fraction of the human population. Suicide is the most extreme symptom of depression, but millions of people, not quite so drastically afflicted, live in misery and partial or complete uselessness, and afflict their families as well by their affliction. The introduction of fluoxetine was a breakthrough in the treatment of depression, and depressives are now much more likely to be diagnosed and treated than they were only a decade ago. Duloxetine is in clinical trials for the treatment of depression and is likely to become a marketed drug for the purpose.

Depression is often associated with other diseases and conditions, or caused by such other conditions. For example, it is associated with Parkinson's disease; with HIV; with Alzheimer's disease; and with abuse of anabolic steroids. Depression may also be associated with abuse of any substance, or may be associated with behavioral problems resulting from or occurring in combination with head injuries, mental retardation or stroke. Depression in all its variations is a preferred target of treatment with the present adjunctive therapy method and compositions.

Obsessive-compulsive disease appears in a great variety of degrees and symptoms, generally linked by the victim's uncontrollable urge to perform needless, ritualistic acts. Acts of acquiring, ordering, cleansing and the like, beyond any rational need or rationale, are the outward characteristic of the disease. A badly afflicted subject may be unable to do anything but carry out the rituals required by the disease. Fluoxetine is approved in the United States and other countries for the treatment of obsessive-compulsive disease and has been found to be effective.

Obesity is a frequent condition in the American population. It has been found that fluoxetine will enable an obese subject to lose weight, with the resulting benefit to the circulation and heart condition, as well as general well being and energy.

Urinary incontinence is classified generally as stress or urge incontinence, depending on whether its root cause is the inability of the sphincter muscles to keep control, or the overactivity of the bladder muscles. Duloxetine controls both types of incontinence, or both types at once, and so is important to the many who suffer from this embarrassing and disabling disorder.

The present treatment methods are useful for treating many other diseases, disorders and conditions as well, as set out below. In many cases, the diseases to be mentioned here are classified in the International Classification of Diseases, 9th Edition (ICD), or in the Diagnostic and Statistical Manual of Mental Disorders, 3rd Version Revised, published by the American Psychiatric Association (DSM). In such cases, the ICD or DSM code numbers are supplied below for the convenience of the reader.

depression, ICD 296.2 & 296.3, DSM 296, 294.80, 293.81, 293.82, 293.83, 310.10, 318.00, 317.00 migraine pain, particularly neuropathic pain bulimia, ICD 307.51, DSM 307.51 premenstrual syndrome or late luteal phase syndrome, DSM 307.90 alcoholism, ICD 305.0, DSM 305.00 & 303.90 tobacco abuse, ICD 305.1, DSM 305.10 & 292.00 panic disorder, ICD 300.01, DSM 300.01 & 300.21 anxiety, ICD 300.02, DSM 300.00 post-traumatic syndrome, DSM 309.89 memory loss, DSM 294.00 dementia of aging, ICD 290 social phobia, ICD 300.23, DSM 300.23 attention deficit hyperactivity disorder, ICD 314.0 disruptive behavior disorders, ICD 312 impulse control disorders, ICD 312, DSM 312.39 & 312.34 borderline personality disorder, ICD 301.83, DSM 301.83 chronic fatigue syndrome premature ejaculation, DSM 302.75 erectile difficulty, DSM 302.72 anorexia nervosa, ICD 307.1, DSM 307.10 disorders of sleep, ICD 307.4 autism mutism trichotillomania

Further, the compounds of formula I are useful for alleviating the symptoms of smoking cessation or nicotine withdrawal when administered alone or in combination with a serotonin reuptake inhibitor. The SRI's to be used in this treatment method, and the administration methods and formulations, are as described above. The use of the present compounds with SRI's in subjects striving to stop use of tobacco or nicotine provides alleviation of the usual painful and damaging symptoms of such subjects, including nervousness, irritability, craving, excessive appetite, anxiety, depression in many forms, inability to concentrate, and the like. The control or elimination of weight gain in the subject undergoing withdrawal from or reduction of tobacco or nicotine use is a particularly valuable and preferred benefit of the use of a present compound in combination with an SRI.

Therapeutic Applications The compounds of formula I are useful for other important therapeutic purposes, as well as in combination with SRIs and in nicotine withdrawal or smoking cessation cases. In particular, the compounds are valuable for binding, blocking or modulating the serotonin-1A receptor, for binding, blocking or modulating the serotonin-2A receptor, and for the treatment or prophylaxis of conditions caused by or influenced by defective function of these receptors. In particular, the compounds are useful for antagonism at the serotonin-1A receptor and the serotonin-2A receptor, and accordingly are used for the treatment or prevention of conditions caused by or affected by excessive activity of these receptors.

More particularly, the compounds of formula I are useful in the treatment of anxiety, depression, hypertension, cognitive disorders, psychosis, sleep disorders, gastric motility disorders, sexual dysfunction, brain trauma, memory loss, appetite disorders and obesity, substance abuse, obsessive-compulsive disease, panic disorder and migraine.

Anxiety and its frequent concomitant, panic disorder, may be particularly mentioned in connection with the present compounds. The subject is carefully explained by the Diagnostic and Statistical Manual of Mental Disorders, published by the American Psychiatric Association, which classifies anxiety under its category 300.02. It is understood that the following specific disorders are also included within the method of the present invention; "generalized anxiety disorder", "panic disorder", "social phobia", "social anxiety", "post traumatic stress disorder", "acute stress disorder", "anxiety due to general medical condition", "substance induced anxiety disorder", and "anxiety disorder not otherwise specified". A further particularly noted disorder is depression and the group of depression-related disorders, which are discussed above in the discussion of adjunctive therapy with SRIs. Further included within the scope of the term anxiety is "social functioning" as appreciated by one of ordinary skill in the art.

The unique combination of pharmacological properties possessed by the compounds of formula I permit those compounds to be used in a method of simultaneously treating anxiety and depression. The anxiety portion of the combined syndrome is believed to be attacked by the 5HT-$1_A$ receptor-affecting property of the compounds, and the depression portion of the condition is believed to be addressed by the reuptake inhibition property. Thus, administration of an effective amount, which is determined in an analogous manner as discussed hereinabove, of a compound of formula I, will provide a method of simultaneously treating anxiety and depression.

Pharmaceutical Compositions

It is customary to formulate pharmaceuticals for administration, to provide control of the dosage and stability of the product in shipment and storage, and the usual methods of formulation are entirely applicable to the compounds of formula I. Such compositions, comprising at least one pharmaceutically acceptable carrier, are valuable and novel because of the presence of the compounds of formula I therein. Although pharmaceutical chemists are well aware of many effective ways to formulate pharmaceuticals, which technology is applicable to the present compounds, some discussion of the subject will be given here for the convenience of the reader.

The usual methods of formulation used in pharmaceutical science and the usual types of compositions may be used according to the present invention, including tablets, chewable tablets, capsules, solutions, parenteral solutions, intranasal sprays or powders, troches, suppositories, transdermal patches and suspensions. In general, compositions contain from about 0.5% to about 50% of the compound in total, depending on the desired dose and the type of composition to be used. The amount of the compound, however, is best defined as the effective amount, that is, the amount of each compound which provides the desired dose to the subject in need of such treatment. The activity of the compounds do not depend on the nature of the composition, so the compositions are chosen and formulated solely for convenience and economy. Any compound may be formulated in any desired form of composition. Some discussion of different compositions will be provided, followed by some typical formulations.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acidic contents of the stomach. Such formulations are created by coating a solid dosage form with a film of a polymer which is insoluble in acidic environments, and soluble in basic environments. Exemplary films are cellulose acetate phthalate, polyvinyl acetate phthalate, hydroxypropyl methylcellulose phthalate and hydroxypropyl methylcellulose acetate succinate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established practice. Instantly dissolving tablet-like formulations are also now frequently used to assure that the subject consumes the dosage form, and to avoid the difficulty in swallowing solid objects that bothers some subjects.

When it is desired to administer the combination as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with pores through which the drugs are pumped by osmotic action.

The following typical formulae are provided for the interest and information of the pharmaceutical scientist.

Formulation 1
Hard gelatin capsules are prepared using the following ingredients:

| | Quantity (mg/capsule) |
|---|---|
| Example #1 | 20 mg |
| Starch dried | 200 mg |
| Magnesium stearate | 10 mg |
| Total | 230 mg |

Formulation 2
Composition of 40 mg Capsules - Total (net) 230 mg

| Ingredient | Amount mg/ capsule | Composition % by weight |
|---|---|---|
| 4-(7-benzo(b)thiophene-1,2,3,6-tetrahydropyridyl)-1-cyclohexyl-2-(2-pyridyl)butan-1-one | 40.00 | 17.55 |
| Sodium Lauryl Sulfate | 1.84 | 0.80 |
| Magnesium Stearate Vegetable | 1.15 | 0.50 |
| Starch Flowable Powder | 187.01 | 81.15 |

Add the 4-(7-benzo(b)thiophene-1,2,3,6-tetrahydropyridyl)-1-cyclohexyl-2-(2-pyridyl)butan-1-one, sodium lauryl sulfate and starch flowable powder (50% of total amount) through a #20 security screen into a stainless steel container. Mix the components in an appropriate powder mixer, such as a Twin Shell blender. Then pass the components through a 0.610 screen using a mill, such as a Quadro Comil, and chase the balance of the starch through the mill into the stainless steel container. Move the entire mixture to the powder mixer and mix for 30 minutes. Then add the magnesium stearate through a #40 screen into the powder mixer and mix for 10 minutes. Then fill the appropriate amount into gelatin capsules No. 3 using a capsule filling machine.

As with any group of structurally related compounds which possess a particular generic utility, certain groups and configurations are preferred for compounds of formula I.

With respect to X, compounds of formula I wherein X is O or S are preferred. With respect to Y, compounds of formula I wherein Y is —C(=O)— or —CH(OH)— are preferred. With respect to $R_{1a}$, $R_{1b}$ and $R_{1c}$, compounds of formula I wherein $R_{1a}$, $R_{1b}$ and $R_{1c}$ are H, F, Cl, Br, OH, $C_1$–$C_4$ alkyl or $C_1$–$C_4$ alkoxy are preferred. With respect to $R_2$, compounds of formula I wherein $R_2$ is H, $C_1$–$C_4$ alkyl and —C(=O)$NR_7R_8$ are preferred. With respect to $R_3$, compounds of formula I wherein $R_3$ is H or methyl are preferred. With respect to $R_4$, compounds of formula I wherein $R_4$ is phenyl, naphthyl, cyclopentyl, cyclohexyl, 2-pyridyl, 3-pyridyl or 4-pyridyl are preferred. With respect to $R_5$, compounds of formula I wherein $R_5$ is phenyl, naphthyl, cyclopentyl, cyclohexyl, 2-pyridyl, 3-pyridyl or 4 pyridyl are preferred. With respect to the piperidine ring on formula I, the following substitutions for $R_{6a}$ and $R_{6b}$ are preferred:

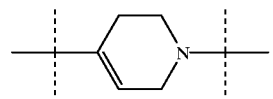

(a)

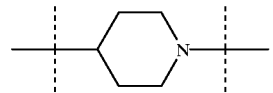

(b)

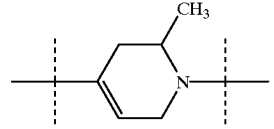

(c)

-continued

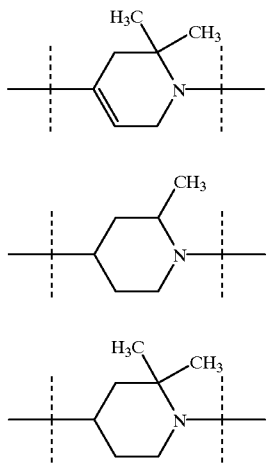

(d)

(e)

(f)

We claim:
1. A compound of the formula:

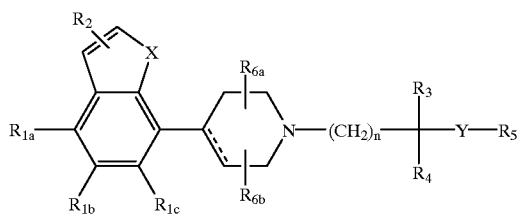

wherein:
X is O, S, NR, S(=O), or S(=O)$_2$;
Y is —C(=O)—, —CH(OH)—, —CH$_2$—, —C(=NOR), CHNR$_7$R, S, SO, or SO$_2$;
------- represents a single or a double bond;
n is 1, 2, 3 or 4;
R is H or C$_1$–C$_6$ alkyl;
R$_{1a}$, R$_{1b}$, R$_{1c}$ and R$_2$ are each independently H, F, Cl, Br, I, OH, C$_1$–C$_6$ alkyl, C$_1$–C$_6$ alkoxy, halo(C$_1$–C$_6$)alkyl, (C$_1$–C$_6$)alkylthio, phenyl, NO$_2$, —NR$_7$R$_8$, —C(=O)NR$_7$R$_8$, —NR$_7$C(=O)R$_8$, CN or phenyl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, (C$_1$–C$_6$)alkylthio, phenyl, NO$_2$, NH$_2$, or CN;
R$_3$ is H, OH, hydroxy(C$_1$–C$_6$)alkyl, C$_1$–C$_6$ alkyl, C$_1$–C$_6$ alkoxy, or (C$_1$–C$_6$)alkylthio;
R$_4$ is aryl, pyridyl, C$_3$–C$_8$ cycloalkyl, aryl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, (C$_1$–C$_6$)alkylthio, phenyl, NO$_2$, NH$_2$, or CN; or pyridyl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, (C$_1$–C$_6$)alkylthio, phenyl, NO$_2$, NH$_2$, or CN;
R$_5$ is aryl, pyridyl, C$_3$–C$_8$ cycloalkyl, aryl substituted with from 1 to 3 substituents selected from the group consisting of F, Cl, Br, I, OH, C$_1$–C$_6$ alkyl, C$_1$–C$_6$ alkoxy, hydroxy(C$_1$–C$_6$)alkyl, halo(C$_1$–C$_6$)alkyl, (C$_1$–C$_6$)alkylthio, phenyl, NO$_2$, NH$_2$, or CN; or pyridyl substituted with from 1 to 3 substituents selected from the group consisting of F, Cl, Br, I, OH, C$_1$–C$_6$ alkyl, C$_1$–C$_6$ alkoxy, hydroxy(C$_1$–C$_6$)alkyl, halo(C$_1$–C$_6$) alkyl, (C$_1$–C$_6$)alkylthio, phenyl, NO$_2$, NH$_2$, or CN;
R$_{6a}$ and R$_{6b}$ are each independently H or C$_1$–C$_3$ alkyl;
R$_7$ and R$_8$ are each independently H, C$_1$–C$_6$ alkyl, aryl or aryl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, (C$_1$–C$_6$) alkylthio, phenyl, NO$_2$, NH$_2$, or CN;
and the pharmaceutically acceptable salts thereof.

2. A compound according to claim 1 wherein X is O.

3. A compound according to claim 1 wherein X is S.

4. A compound according to claim 2 wherein R$_2$ is H.

5. A compound according to claim 3 wherein R$_2$ is H.

6. A compound according to claim 4 wherein n is 2.

7. A compound according to claim 5 wherein n is 2.

8. A compound according to claim 6 wherein R$_3$ is H.

9. A compound according to claim 7 wherein R$_3$ is H.

10. A compound according to claim 8 wherein R$_4$ is 2-pyridyl.

11. A compound according to claim 9 wherein R$_4$ is 2-pyridyl.

12. A compound according to claim 10 wherein ----- a double bond.

13. A compound according to claim 11 wherein ----- is a double bond.

14. A compound according to claim 12 wherein Y is —C(=O)—.

15. A compound according to claim 13 wherein Y is —C(=O)—.

16. A compound according to claim 2 wherein R$_3$ is methyl.

17. A compound according to claim 3 wherein R$_3$ is methyl.

18. A compound which is 4-(7-benzo(b)thiophene-1,2,3, 6-tetrahydropyridyl)-1-cyclohexyl-2-(2-pyridyl)butan-1-one and the pharmaceutically acceptable salts thereof.

19. A compound which is 4-(7-benzo(b)thiophene-1,2,3, 6-tetrahydropyridyl)-1-cyclohexyl-2-(2-pyridyl)butan-1-one.

20. A compound of the formula:

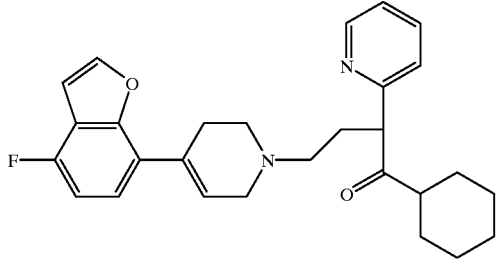

and the pharmaceutically acceptable salts thereof.

21. A compound of the formula:

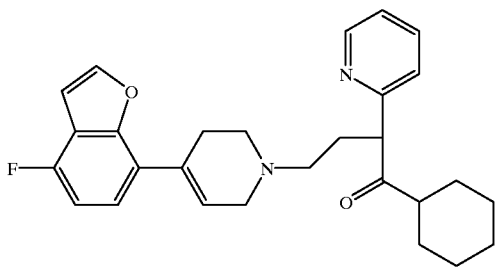

22. A pharmaceutical composition comprising an effective amount of a compound according to claim 1 in combination with a pharmaceutically acceptable carrier, diluent or excipient.

23. A method of inhibiting the reuptake of serotonin and antagonizing the 5-HT$_{1A}$ receptor which comprises administering to a subject in need of such treatment an effective amount of a compound of the formula

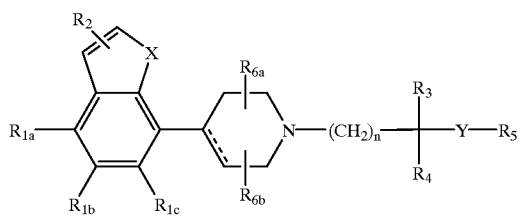

wherein:
X is O, S, NR, S(=O), or S(=O)$_2$;
Y is —C(=O)—, —CH(OH)—, —CH$_2$—, —C(=NOR), CHNR$_7$R, S, SO, or SO$_2$;
------ represents a single or a double bond;
n is 1, 2, 3 or 4;
R is H or C$_1$–C$_6$ alkyl;
R$_{1a}$, R$_{1b}$, R$_{1c}$ and R$_2$ are each independently H, F, Cl, Br, I, OH, C$_1$–C$_6$ alkyl, C$_1$–C$_6$ alkoxy, halo(C$_1$–C$_6$)alkyl, (C$_1$–C$_6$)alkylthio, phenyl, NO$_2$, —NR$_7$R$_8$, —C(=O)NR$_7$R$_8$, —NR$_7$C(=O)R$_8$, CN or phenyl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, (C$_1$–C$_6$)alkylthio, phenyl, NO$_2$, NH$_2$, or CN;
R$_3$ is H, OH, hydroxy(C$_1$–C$_6$)alkyl, C$_1$–C$_6$ alkyl, C$_1$–C$_6$ alkoxy, or (C$_1$–C$_6$)alkylthio;
R$_4$ is aryl, pyridyl, C$_3$–C$_8$ cycloalkyl, aryl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, (C$_1$–C$_6$)alkylthio, phenyl, NO$_2$, NH$_2$, or CN; or pyridyl substituted with from 1 to 3 substituents selected from the group consisting of F, Cl, Br, I, OH, C$_1$–C$_6$ alkyl, C$_1$–C$_6$ alkoxy, halo(C$_1$–C$_6$) alkyl, (C$_1$–C$_6$)alkylthio, phenyl, NO$_2$, NH$_2$, or CN;
R$_5$ is aryl, pyridyl, C$_3$–C$_8$ cycloalkyl, aryl substituted with from 1 to 3 substituents selected from the group consisting of F, Cl, Br, I, OH, C$_1$–C$_6$ alkyl, C$_1$–C$_6$ alkoxy, hydroxy(C$_1$–C$_6$)alkyl, halo(C$_1$–C$_6$)alkyl, (C$_1$–C$_6$) alkylthio, phenyl, NO$_2$, NH$_2$, or CN; or pyridyl substituted with from 1 to 3 substituents selected from the group consisting of F, Cl, Br, I, OH, C$_1$–C$_6$ alkyl, C$_1$–C$_6$ alkoxy, hydroxy(C$_1$–C$_6$)alkyl, halo(C$_1$–C$_6$) alkyl, (C$_1$–C$_6$)alkylthio, phenyl, NO$_2$, NH$_2$, or CN;
R$_{6a}$, and R$_{6b}$ are each independently H or C$_1$–C$_3$ alkyl;
R$_7$ and R$_8$ are each independently H, C$_1$–C$_6$ alkyl, aryl or aryl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, (C$_1$–C$_6$) alkylthio, phenyl, NO$_2$, NH$_2$, or CN;
and the pharmaceutically acceptable salts thereof.

24. A method of potentiating the action of a serotonin reuptake inhibitor comprising administering to a subject in of such treatment a compound formula

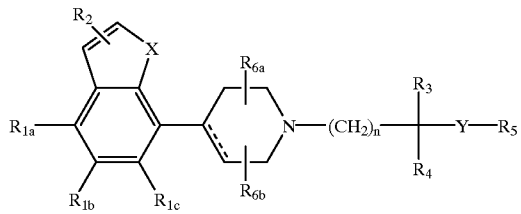

wherein:
X is O, S, NR, S(=O), or S(=O)$_2$;
Y is —C(=O)—, —CH(OH)—, —CH$_2$—, —C(=NOR), CHNR$_7$R, S, SO, or SO$_2$;
------ represents a single or a double bond;
n is 1, 2, 3 or 4;
R is H or C$_1$–C$_6$ alkyl;
R$_{1a}$, R$_{1b}$, R$_{1c}$ and R$_2$ are each independently H, F, Cl, Br, I, OH, C$_1$–C$_6$ alkyl, C$_1$–C$_6$ alkoxy, halo(C$_1$–C$_6$)alkyl, (C$_1$–C$_6$)alkylthio, phenyl, NO$_2$, —NR$_7$R$_8$, —C(=O)NR$_7$R$_8$, —NR$_7$C(=O)R$_8$, CN or phenyl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, (C$_1$–C$_6$)alkylthio, phenyl, NO$_2$, NH$_2$, or CN;
R$_3$ is H, OH, hydroxy(C$_1$–C$_6$)alkyl, C$_1$–C$_6$ alkyl, C$_1$–C$_6$ alkoxy, or (C$_1$–C$_6$)alkylthio;
R$_4$ is aryl, pyridyl, C$_3$–C$_8$ cycloalkyl, aryl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, (C$_1$–C$_6$)alkylthio, phenyl, NO$_2$, NH$_2$, or CN; or pyridyl substituted with from 1 to 3 substituents selected from the group consisting of F, Cl, Br, I, OH, C$_1$–C$_6$ alkyl, C$_1$–C$_6$ alkoxy, halo(C$_1$–C$_6$) alkyl, (C$_1$–C$_6$)alkylthio, phenyl, NO$_2$, NH$_2$, or CN;
R$_5$ is aryl, pyridyl, C$_3$–C$_8$ cycloalkyl, aryl substituted with from 1 to 3 substituents selected from the group consisting of F, Cl, Br, I, OH, C$_1$–C$_6$ alkyl, C$_1$–C$_6$ alkoxy, hydroxy(C$_1$–C$_6$)alkyl, halo(C$_1$–C$_6$)alkyl, (C$_1$–C$_6$) alkylthio, phenyl, NO$_2$, NH$_2$, or CN; or pyridyl substituted with from 1 to 3 substituents selected from the group consisting of F, Cl, Br, I, OH, C$_1$–C$_6$ alkyl, C$_1$–C$_6$ alkoxy, hydroxy(C$_1$–C$_6$)alkyl, halo(C$_1$–C$_6$) alkyl, (C$_1$–C$_6$)alkylthio, phenyl, NO$_2$, NH$_2$, or CN;
R$_{6a}$ and R$_{6b}$ are each independently H or C$_1$–C$_3$ alkyl;
R$_7$ and R$_8$ are each independently H, C$_1$–C$_6$ alkyl, aryl or aryl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, (C$_1$–C$_6$) alkylthio, phenyl, NO$_2$, NH$_2$, or CN;
and the pharmaceutically acceptable salts thereof.

25. A method of treating depression comprising administering to a subject in need thereof an effective amount of a compound of formula:

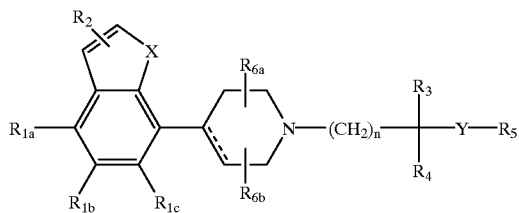

wherein:

X is O, S, NR, S(=O), or S(=O)$_2$;

Y is —C(=O)—, —CH(OH)—, —CH—, —C(=NOR), CHNR$_7$R, S, SO, or SO$_2$;

------ represents a single or a double bond;

n is 1, 2, 3 or 4;

R is H or C$_1$–C$_6$ alkyl;

R$_{1a}$, R$_{1b}$, R$_{1c}$ and R$_2$ are each independently H, F, Cl, Br, I, OH, C$_1$–C$_6$ alkyl, C$_1$–C$_6$ alkoxy, halo(C$_1$–C$_6$)alkyl, (C$_1$–C$_6$)alkylthio, phenyl, NO$_2$, —NR$_7$R$_8$, —C(=O)NR$_7$R$_8$, —NR$_7$C(=O)R$_8$, CN or phenyl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, (C$_1$–C$_6$)alkylthio, phenyl, NO$_2$, NH$_2$, or CN;

R$_3$ is H, OH, hydroxy(C$_1$–C$_6$)alkyl, C$_1$–C$_6$ alkyl, C$_1$–C$_6$ alkoxy, or (C$_1$–C$_6$)alkylthio;

R$_4$ is aryl, pyridyl, C$_3$–C$_8$ cycloalkyl, aryl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, (C$_1$–C$_6$)alkylthio, phenyl, NO$_2$, NH$_2$, or CN; or pyridyl substituted with from 1 to 3 substituents selected from the group consisting of F, Cl, Br, I, OH, C$_1$–C$_6$ alkyl, C$_1$–C$_6$ alkoxy, halo(C$_1$–C$_6$) alkyl, (C$_1$–C$_6$)alkylthio, phenyl, NO$_2$, NH$_2$, or CN;

R$_5$ is aryl, pyridyl, C$_3$–C$_8$ cycloalkyl, aryl substituted with from 1 to 3 substituents selected from the group consisting of F, Cl, Br, I, OH, C$_1$–C$_6$ alkyl, C$_1$–C$_6$ alkoxy, hydroxy(C$_1$–C$_6$)alkyl, halo(C$_1$–C$_6$)alkyl, (C$_1$–C$_6$) alkylthio, phenyl, NO$_2$, NH$_2$, or CN; or pyridyl substituted with from 1 to 3 substituents selected from the group consisting of F, Cl, Br, I, OH, C$_1$–C$_6$ alkyl, C$_1$–C$_6$ alkoxy, hydroxy(C$_1$–C$_6$)alkyl, halo(C$_1$–C$_6$) alkyl, (C$_1$–C$_6$)alkylthio, phenyl, NO$_2$, NH$_2$, or CN;

R$_{6a}$ and R$_{6b}$ are each independently H or C$_1$–C$_3$ alkyl;

R$_7$ and R$_8$ are each independently H, C$_1$–C$_6$ alkyl, aryl or aryl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, (C$_1$–C$_6$) alkylthio, phenyl, NO$_2$, NH$_2$, or CN;

and the pharmaceutically acceptable salts thereof.

\* \* \* \* \*